(12) United States Patent
Hunter

(10) Patent No.: US 11,911,141 B2
(45) Date of Patent: Feb. 27, 2024

(54) DEVICES, SYSTEMS AND METHODS FOR USING AND MONITORING TUBES IN BODY PASSAGEWAYS

(71) Applicant: CANARY MEDICAL INC., Vancouver (CA)

(72) Inventor: William L. Hunter, Vancouver (CA)

(73) Assignee: Canary Medical Switzerland AG, Baar (CH)

( * ) Notice: Subject to any disclaimer, the term of this patent is extended or adjusted under 35 U.S.C. 154(b) by 308 days.

(21) Appl. No.: 17/547,067

(22) Filed: Dec. 9, 2021

(65) Prior Publication Data
US 2022/0167867 A1  Jun. 2, 2022

Related U.S. Application Data

(63) Continuation of application No. 16/671,811, filed on Nov. 1, 2019, now Pat. No. 11,389,079, which is a (Continued)

(51) Int. Cl.
*A61F 2/82* (2013.01)
*A61B 5/00* (2006.01)
(Continued)

(52) U.S. Cl.
CPC ............ *A61B 5/065* (2013.01); *A61B 5/0031* (2013.01); *A61B 5/02055* (2013.01); *A61B 5/6847* (2013.01); *A61B 5/6885* (2013.01); *A61F 2/82* (2013.01); *A61F 2/954* (2013.01); *A61F 2/958* (2013.01); *A61B 5/026* (2013.01); *A61B 5/02007* (2013.01); *A61B 5/0215* (2013.01); *A61B 5/067* (2013.01); *A61B 5/1473* (2013.01); *A61B 5/20* (2013.01); *A61B 2560/0266* (2013.01); *A61B 2562/12* (2013.01); *A61F 2/856* (2013.01); *A61F 2/90* (2013.01); *A61F 2250/0096* (2013.01); *A61M 2025/09183* (2013.01)

(58) Field of Classification Search
CPC ... A61B 5/065; A61B 5/0031; A61B 5/02055; A61B 5/6847; A61B 5/6885; A61F 2/82; A61F 2/954; A61F 2/958; A61F 2/856
See application file for complete search history.

(56) References Cited

U.S. PATENT DOCUMENTS

| 5,383,874 A | * | 1/1995 | Jackson ............ A61B 18/1206 606/1 |
| 5,591,227 A | | 1/1997 | Dinh et al. |

(Continued)

FOREIGN PATENT DOCUMENTS

| CN | 1709210 A | 12/2005 |
| CN | 1899222 A | 1/2007 |

(Continued)

OTHER PUBLICATIONS

Extended European Search Report for European Application No. 15842678.3, dated Feb. 5, 2019, 13 Pages.
(Continued)

*Primary Examiner* — Suzette J Gherbi

(57) ABSTRACT

Tubes (e.g., catheters, endotracheal or chest tubes and bypass grafts) are provided, comprising a catheter and a plurality of sensors.

10 Claims, 19 Drawing Sheets

Related U.S. Application Data continuation of application No. 15/320,275, filed as application No. PCT/US2015/037823 on Jun. 25, 2015, now Pat. No. 10,524,694.

(60) Provisional application No. 62/017,086, filed on Jun. 25, 2014.

(51) Int. Cl.

| | | |
|---|---|---|
| *A61B 5/06* | (2006.01) | |
| *A61F 2/958* | (2013.01) | |
| *A61F 2/954* | (2013.01) | |
| *A61B 5/0205* | (2006.01) | |
| *A61F 2/856* | (2013.01) | |
| *A61B 5/02* | (2006.01) | |
| *A61B 5/0215* | (2006.01) | |
| *A61B 5/026* | (2006.01) | |
| *A61B 5/1473* | (2006.01) | |
| *A61B 5/20* | (2006.01) | |
| *A61F 2/90* | (2013.01) | |
| *A61M 25/09* | (2006.01) | |

(56) References Cited

U.S. PATENT DOCUMENTS

| | | | |
|---|---|---|---|
| 5,651,780 A * | 7/1997 | Jackson | A61B 18/1206 606/1 |
| 5,672,954 A | 9/1997 | Watanabe | |
| 5,716,981 A | 2/1998 | Hunter et al. | |
| 5,749,824 A | 5/1998 | Guth | |
| 5,779,729 A | 7/1998 | Severini | |
| 5,833,603 A | 11/1998 | Kovacs et al. | |
| 6,053,873 A | 4/2000 | Govari et al. | |
| 6,123,722 A | 9/2000 | Fogarty et al. | |
| 6,172,778 B1 | 1/2001 | Reinhorn et al. | |
| 6,206,835 B1 | 3/2001 | Spillman, Jr. et al. | |
| 6,331,163 B1 | 12/2001 | Kaplan | |
| 6,387,124 B1 | 5/2002 | Buscemi et al. | |
| 6,447,448 B1 | 9/2002 | Ishikawa et al. | |
| 6,610,101 B2 | 8/2003 | Herr et al. | |
| 6,706,071 B1 | 3/2004 | Wolter | |
| 6,712,778 B1 | 3/2004 | Jeffcoat et al. | |
| 6,852,153 B2 | 2/2005 | Uhlir-Tsang et al. | |
| 6,869,443 B2 | 3/2005 | Buscemi et al. | |
| 7,009,511 B2 | 3/2006 | Mazar et al. | |
| 7,011,678 B2 | 3/2006 | Tenerz et al. | |
| 7,025,734 B1 * | 4/2006 | Ellis | A61B 5/1459 600/585 |
| 7,025,778 B2 | 4/2006 | Hayashi et al. | |
| 7,044,981 B2 | 5/2006 | Liu et al. | |
| 7,127,300 B2 | 10/2006 | Mazar et al. | |
| 7,130,695 B2 | 10/2006 | Czygan et al. | |
| 7,179,289 B2 | 2/2007 | Shanley | |
| 7,208,010 B2 | 4/2007 | Shanley et al. | |
| 7,294,145 B2 | 11/2007 | Ward | |
| 7,377,937 B2 | 5/2008 | Dolan | |
| 7,383,071 B1 | 6/2008 | Russell et al. | |
| 7,416,530 B2 | 8/2008 | Turner et al. | |
| 7,452,334 B2 | 11/2008 | Gianchandani et al. | |
| 7,491,188 B2 | 2/2009 | Holman et al. | |
| 7,553,923 B2 | 6/2009 | Williams et al. | |
| 7,691,141 B2 | 4/2010 | Lewis et al. | |
| 7,806,917 B2 | 10/2010 | Xiao | |
| 7,813,808 B1 | 10/2010 | Doron et al. | |
| 7,879,082 B2 | 2/2011 | Brown | |
| 7,914,568 B2 | 3/2011 | Cully et al. | |
| 7,942,923 B2 | 5/2011 | Gregorich | |
| 8,001,925 B2 | 8/2011 | Kantor | |
| 8,003,157 B2 | 8/2011 | Andreacchi et al. | |
| 8,080,051 B2 | 12/2011 | Lewis et al. | |
| 8,100,960 B2 | 1/2012 | Bruszewski | |
| 8,123,799 B1 | 2/2012 | Malik et al. | |
| 8,167,810 B2 * | 5/2012 | Maschke | A61B 8/12 600/478 |
| 8,277,833 B2 | 10/2012 | Atanasoska et al. | |
| 8,277,867 B2 | 10/2012 | Fredrickson et al. | |
| 8,283,793 B2 | 10/2012 | Pless | |
| 8,287,588 B2 | 10/2012 | Leynov et al. | |
| 8,308,794 B2 | 11/2012 | Martinson et al. | |
| 8,311,632 B2 | 11/2012 | Pless et al. | |
| 8,480,612 B2 * | 7/2013 | Kassem | A61B 5/031 604/9 |
| 8,536,667 B2 * | 9/2013 | de Graff | A61B 5/28 257/419 |
| 8,556,888 B2 | 10/2013 | Nields et al. | |
| 8,764,728 B2 * | 7/2014 | Ciavarella | A61B 5/287 600/374 |
| 8,876,739 B2 | 11/2014 | Salarian et al. | |
| 8,996,892 B1 | 3/2015 | Chu et al. | |
| 9,019,098 B2 | 4/2015 | Okano | |
| 9,307,932 B2 | 4/2016 | Mariani et al. | |
| 9,445,930 B2 | 9/2016 | Chen et al. | |
| 9,456,915 B2 | 10/2016 | Chen et al. | |
| 9,726,629 B2 * | 8/2017 | Bhatia | G01N 27/07 |
| 9,949,692 B2 * | 4/2018 | Hunter | A61B 5/0031 |
| 9,986,917 B2 | 6/2018 | Haverkost et al. | |
| 10,499,855 B2 * | 12/2019 | Hunter | A61F 2/07 |
| 10,524,694 B2 * | 1/2020 | Hunter | A61F 2/82 |
| 10,542,931 B2 * | 1/2020 | Kuraguntla | A61B 5/0215 |
| 2002/0010279 A1 | 1/2002 | Satcher et al. | |
| 2002/0024450 A1 | 2/2002 | Townsend et al. | |
| 2002/0128546 A1 | 9/2002 | Silver | |
| 2002/0151816 A1 * | 10/2002 | Rich | A61B 5/02028 600/547 |
| 2003/0050640 A1 | 3/2003 | Lee et al. | |
| 2003/0069644 A1 | 4/2003 | Kovacevic et al. | |
| 2003/0104030 A1 | 6/2003 | Igaki et al. | |
| 2003/0204245 A1 | 10/2003 | Brightbill | |
| 2003/0204267 A1 | 10/2003 | Hazebrouck et al. | |
| 2003/0229388 A1 | 12/2003 | Hayashi et al. | |
| 2004/0019382 A1 | 1/2004 | Amirouche et al. | |
| 2004/0019384 A1 | 1/2004 | Kirking et al. | |
| 2004/0034344 A1 * | 2/2004 | Ryba | A61B 18/02 606/23 |
| 2004/0116822 A1 | 6/2004 | Lindsey | |
| 2004/0193021 A1 * | 9/2004 | Zdeblick | A61B 5/036 977/932 |
| 2004/0199241 A1 | 10/2004 | Gravett et al. | |
| 2004/0204766 A1 | 10/2004 | Siebel | |
| 2004/0211580 A1 | 10/2004 | Wang et al. | |
| 2005/0021126 A1 | 1/2005 | Machan et al. | |
| 2005/0051871 A1 | 3/2005 | Lowther et al. | |
| 2005/0065592 A1 | 3/2005 | Holzer | |
| 2005/0149170 A1 | 7/2005 | Tassel et al. | |
| 2005/0149173 A1 | 7/2005 | Hunter et al. | |
| 2005/0152945 A1 | 7/2005 | Hunter et al. | |
| 2005/0165317 A1 | 7/2005 | Turner et al. | |
| 2005/0171594 A1 | 8/2005 | Machan et al. | |
| 2005/0177103 A1 | 8/2005 | Hunter et al. | |
| 2005/0181004 A1 | 8/2005 | Hunter et al. | |
| 2005/0181005 A1 | 8/2005 | Hunter et al. | |
| 2005/0181009 A1 | 8/2005 | Hunter et al. | |
| 2005/0181011 A1 | 8/2005 | Hunter et al. | |
| 2005/0186242 A1 | 8/2005 | Hunter et al. | |
| 2005/0187639 A1 | 8/2005 | Hunter et al. | |
| 2005/0242666 A1 | 11/2005 | Huscher et al. | |
| 2005/0267569 A1 | 12/2005 | Barrett et al. | |
| 2006/0009856 A1 | 1/2006 | Sherman et al. | |
| 2006/0030771 A1 | 2/2006 | Levine et al. | |
| 2006/0030945 A1 | 2/2006 | Wright | |
| 2006/0047283 A1 | 3/2006 | Evans, III et al. | |
| 2006/0055088 A1 | 3/2006 | Nakahashiki et al. | |
| 2006/0069403 A1 | 3/2006 | Shalon et al. | |
| 2006/0079740 A1 * | 4/2006 | Silver | A61B 5/6882 600/353 |
| 2006/0079836 A1 | 4/2006 | Holman et al. | |
| 2006/0111777 A1 | 5/2006 | Chen | |
| 2006/0122522 A1 | 6/2006 | Chavan et al. | |
| 2006/0129050 A1 | 6/2006 | Martinson et al. | |
| 2006/0142670 A1 | 6/2006 | DiSilvestro et al. | |
| 2006/0155358 A1 | 7/2006 | LaDuca et al. | |
| 2006/0192214 A1 | 8/2006 | Ogihara et al. | |
| 2006/0224088 A1 | 10/2006 | Roche | |

(56) References Cited

U.S. PATENT DOCUMENTS

| | | |
|---|---|---|
| 2006/0226575 A1 | 10/2006 | Maghribi et al. |
| 2006/0229730 A1 | 10/2006 | Railey et al. |
| 2006/0271112 A1 | 11/2006 | Martinson et al. |
| 2006/0271199 A1 | 11/2006 | Johnson |
| 2007/0004994 A1 | 1/2007 | Sherman |
| 2007/0005141 A1 | 1/2007 | Sherman |
| 2007/0089518 A1 | 4/2007 | Ericson et al. |
| 2007/0233065 A1 | 10/2007 | Donofrio et al. |
| 2007/0234819 A1 | 10/2007 | Amirouche et al. |
| 2007/0238984 A1 | 10/2007 | Maschke et al. |
| 2007/0239282 A1 | 10/2007 | Caylor, III et al. |
| 2007/0270940 A1 | 11/2007 | Doty |
| 2007/0276477 A1 | 11/2007 | Lee et al. |
| 2008/0004689 A1* | 1/2008 | Jahnke ............... A61F 2/958 623/1.34 |
| 2008/0020012 A1 | 1/2008 | Ju et al. |
| 2008/0021307 A1 | 1/2008 | Freeman et al. |
| 2008/0027679 A1 | 1/2008 | Shklarski |
| 2008/0033527 A1* | 2/2008 | Nunez ............... A61F 2/07 623/1.13 |
| 2008/0065225 A1 | 3/2008 | Wasielewski et al. |
| 2008/0076972 A1 | 3/2008 | Dorogusker et al. |
| 2008/0088436 A1 | 4/2008 | Reeves et al. |
| 2008/0176271 A1* | 7/2008 | Silver ............... A61B 5/413 422/68.1 |
| 2008/0215609 A1 | 9/2008 | Cleveland et al. |
| 2008/0275350 A1 | 11/2008 | Liao et al. |
| 2008/0300597 A1 | 12/2008 | Morgan et al. |
| 2008/0300659 A1 | 12/2008 | Matos |
| 2008/0306325 A1 | 12/2008 | Burnett et al. |
| 2008/0312543 A1* | 12/2008 | Laufer ............... A61B 8/06 600/486 |
| 2009/0012372 A1 | 1/2009 | Burnett et al. |
| 2009/0043352 A1* | 2/2009 | Brooke ............... A61N 1/36185 607/28 |
| 2009/0048524 A1 | 2/2009 | Wildau et al. |
| 2009/0088756 A1 | 4/2009 | Anderson |
| 2009/0119222 A1 | 5/2009 | O'Neil |
| 2009/0131767 A1 | 5/2009 | Arne et al. |
| 2009/0157146 A1 | 6/2009 | Linder et al. |
| 2009/0192588 A1 | 7/2009 | Shin et al. |
| 2009/0242425 A1* | 10/2009 | Kamath ............... A61B 5/1495 205/792 |
| 2009/0248126 A1 | 10/2009 | Nippoldt et al. |
| 2009/0253587 A1 | 10/2009 | Fernandez |
| 2009/0254063 A1 | 10/2009 | Oepen et al. |
| 2009/0264894 A1 | 10/2009 | Wasielewski |
| 2009/0281412 A1 | 11/2009 | Boyden et al. |
| 2009/0292195 A1* | 11/2009 | Boyden ............... A61B 5/02007 600/407 |
| 2010/0023108 A1 | 1/2010 | Toner et al. |
| 2010/0042121 A1 | 2/2010 | Schneider et al. |
| 2010/0087782 A1* | 4/2010 | Ghaffari ............... A61B 5/02007 623/1.11 |
| 2010/0100011 A1 | 4/2010 | Roche |
| 2010/0100038 A1 | 4/2010 | Walker et al. |
| 2010/0152621 A1 | 6/2010 | Janna et al. |
| 2010/0191100 A1 | 7/2010 | Anderson et al. |
| 2010/0204551 A1 | 8/2010 | Roche |
| 2010/0217136 A1 | 8/2010 | Turner et al. |
| 2010/0285082 A1 | 11/2010 | Fernandez |
| 2011/0019595 A1 | 1/2011 | Magar et al. |
| 2011/0046452 A1 | 2/2011 | Najafi et al. |
| 2011/0054272 A1 | 3/2011 | Derchak |
| 2011/0063094 A1 | 3/2011 | Meiertoberens et al. |
| 2011/0076332 A1 | 3/2011 | Yu et al. |
| 2011/0087306 A1 | 4/2011 | Goossen |
| 2011/0092948 A1 | 4/2011 | Shachar et al. |
| 2011/0200052 A1 | 8/2011 | Mungo et al. |
| 2011/0210258 A1* | 9/2011 | Black ............... A61N 5/1048 250/336.1 |
| 2011/0257504 A1 | 10/2011 | Hendricks et al. |
| 2011/0288436 A1 | 11/2011 | Stone |
| 2011/0288805 A1 | 11/2011 | Dejnabadi et al. |
| 2011/0319755 A1 | 12/2011 | Stein et al. |
| 2012/0123185 A1 | 5/2012 | Isham |
| 2012/0123498 A1 | 5/2012 | Gross |
| 2012/0123716 A1 | 5/2012 | Clark |
| 2012/0130687 A1 | 5/2012 | Otto et al. |
| 2012/0165597 A1 | 6/2012 | Proulx et al. |
| 2012/0190976 A1* | 7/2012 | Kleinstreuer ......... A61B 34/70 604/247 |
| 2012/0226360 A1 | 9/2012 | Stein et al. |
| 2012/0271200 A1* | 10/2012 | Martinson ............... A61B 5/07 600/587 |
| 2012/0302861 A1 | 11/2012 | Marshall et al. |
| 2013/0030262 A1* | 1/2013 | Burnett ............... A61B 5/14539 600/484 |
| 2013/0041454 A1 | 2/2013 | Dobson et al. |
| 2013/0058556 A1 | 3/2013 | Ohishi et al. |
| 2013/0079675 A1 | 3/2013 | Stein et al. |
| 2013/0109998 A1 | 5/2013 | Swoboda et al. |
| 2013/0123684 A1 | 5/2013 | Giuffrida et al. |
| 2013/0144379 A1 | 6/2013 | Najafi et al. |
| 2013/0213140 A1 | 8/2013 | Eichhorn et al. |
| 2013/0226285 A1* | 8/2013 | Strommer ............ A61B 1/00154 623/1.23 |
| 2013/0245412 A1* | 9/2013 | Rong ............... A61B 5/14532 600/347 |
| 2013/0252610 A1 | 9/2013 | Kim et al. |
| 2013/0281839 A1 | 10/2013 | Yan et al. |
| 2014/0031063 A1 | 1/2014 | Park et al. |
| 2014/0081154 A1 | 3/2014 | Toth |
| 2014/0085102 A1 | 3/2014 | McCormick |
| 2014/0088391 A1* | 3/2014 | Leach ............... C12Q 1/001 600/347 |
| 2014/0135589 A1 | 5/2014 | Osorio |
| 2014/0144070 A1 | 5/2014 | Waterson et al. |
| 2014/0214149 A1* | 7/2014 | Kuraguntla ......... A61B 5/02055 623/1.15 |
| 2014/0256324 A1 | 9/2014 | Mohanty et al. |
| 2014/0257047 A1 | 9/2014 | Sillay et al. |
| 2014/0275849 A1 | 9/2014 | Acquista |
| 2014/0275861 A1 | 9/2014 | Kroh et al. |
| 2014/0328253 A1 | 11/2014 | Lee et al. |
| 2015/0112188 A1* | 4/2015 | Stigall ............... A61B 17/064 600/424 |
| 2015/0238304 A1 | 8/2015 | Lamraoui |
| 2015/0335290 A1* | 11/2015 | Hunter ............... A61B 5/076 623/1.13 |
| 2016/0029952 A1 | 2/2016 | Hunter |
| 2016/0038087 A1* | 2/2016 | Hunter ............... A61B 5/0205 623/1.1 |
| 2016/0101281 A1 | 4/2016 | Chen |
| 2016/0192878 A1 | 7/2016 | Hunter |
| 2016/0310077 A1* | 10/2016 | Hunter ............... A61B 5/6862 |
| 2016/0340177 A1 | 11/2016 | Takada |
| 2017/0035593 A1 | 2/2017 | Chen et al. |
| 2017/0119566 A1 | 5/2017 | Chen et al. |
| 2017/0138986 A1 | 5/2017 | Kern |
| 2017/0181825 A1 | 6/2017 | Hunter |
| 2017/0189553 A1 | 7/2017 | Hunter |
| 2017/0196478 A1 | 7/2017 | Hunter |
| 2017/0196499 A1 | 7/2017 | Hunter |
| 2017/0196508 A1 | 7/2017 | Hunter |
| 2017/0196509 A1* | 7/2017 | Hunter ............... A61B 5/6869 |
| 2017/0328931 A1 | 11/2017 | Zhang et al. |
| 2018/0064335 A1* | 3/2018 | Rutschman .......... H04N 23/661 |
| 2018/0235546 A1 | 8/2018 | Hunter |
| 2019/0076033 A1 | 3/2019 | Sweeney et al. |
| 2020/0054215 A1 | 2/2020 | Roche |
| 2020/0245895 A1* | 8/2020 | Hunter ............... A61B 5/065 |
| 2020/0289060 A1* | 9/2020 | Hunter ............... A61B 5/0031 |
| 2021/0077241 A1 | 3/2021 | Hunter |

FOREIGN PATENT DOCUMENTS

| | | |
|---|---|---|
| CN | 101043859 A | 9/2007 |
| CN | 101094622 A | 12/2007 |
| CN | 101188984 A | 5/2008 |
| CN | 101257860 A | 9/2008 |
| CN | 101484070 A | 7/2009 |

(56) References Cited

FOREIGN PATENT DOCUMENTS

| | | |
|---|---|---|
| CN | 101495025 A | 7/2009 |
| CN | 101557777 A | 10/2009 |
| CN | 101773387 A | 7/2010 |
| CN | 202036215 U | 11/2011 |
| CN | 102740803 A | 10/2012 |
| CN | 102885626 A | 1/2013 |
| CN | 103313661 A | 9/2013 |
| CN | 103458830 A | 12/2013 |
| CN | 103735303 A | 4/2014 |
| CN | 103957992 A | 7/2014 |
| DE | 4322619 C1 | 9/1994 |
| GB | 2379882 A | 3/2003 |
| JP | 2004532051 A | 10/2004 |
| JP | 2007083019 A | 4/2007 |
| JP | 2007515195 A | 6/2007 |
| JP | 2008237642 A | 10/2008 |
| JP | 2009542421 A | 12/2009 |
| JP | 2022128381 A | 9/2022 |
| WO | 9836709 A1 | 8/1998 |
| WO | 2002064019 A2 | 8/2002 |
| WO | 2005046467 A1 | 5/2005 |
| WO | 2006029364 A2 | 3/2006 |
| WO | 2006108065 A2 | 10/2006 |
| WO | 2006055443 A3 | 5/2007 |
| WO | 2007057739 | 5/2007 |
| WO | 2008006003 A2 | 1/2008 |
| WO | 2008032316 A2 | 3/2008 |
| WO | 2008088867 A1 | 7/2008 |
| WO | 2012061825 A2 | 5/2012 |
| WO | 2012095784 A1 | 7/2012 |
| WO | 2012170837 | 12/2012 |
| WO | 2013012717 A2 | 1/2013 |
| WO | 2013044160 A2 | 3/2013 |
| WO | 2014144107 | 3/2014 |
| WO | 2014100795 A1 | 6/2014 |
| WO | 2014144070 A1 | 9/2014 |
| WO | 2014209916 A1 | 12/2014 |
| WO | 2015021807 A1 | 2/2015 |
| WO | 2015200704 A1 | 12/2015 |
| WO | 2015200707 A1 | 12/2015 |
| WO | 2015200718 A1 | 12/2015 |
| WO | 2015200720 A2 | 12/2015 |
| WO | 2015200722 A2 | 12/2015 |
| WO | 2015200723 A1 | 12/2015 |

OTHER PUBLICATIONS

Extended European Search Report for European Application No. 21200224.0, dated Mar. 23, 2022, 08 Pages.

International Preliminary Report on Patentability for International Application No. PCT/US2013/077356, dated Jul. 2, 2015, 10 Pages.

International Preliminary Report on Patentability for International Application No. PCT/US2014/028323, dated Sep. 24, 2015, 13 Pages.

International Preliminary Report on Patentability for International Application No. PCT/US2015/037823, dated Jan. 5, 2017, 08 Pages.

International Preliminary Report on Patentability for International Application No. PCT/US2015/037828, dated Jan. 5, 2017, 08 Pages.

International Preliminary Report on Patentability for International Application No. PCT/US2015/050789, dated Mar. 30, 2017, 07 Pages.

Partial Supplementary European Search Report for European Application No. 15842678.3, dated Oct. 16, 2018, 15 Pages.

Xiang X., et al., "A Review of the Implantable Electronic Devices in Biology and Medicine," China Academic Journal Electronic Publishing House, vol. 32 (3), Mar. 3, 2004, pp. 462-467.

Yiming L., et al., "Application of Wireless Sensor Networks in Healthcare," Chinese Journal of Medical Instrumentation, vol. 37, No. 5, Dec. 31, 2013, pp. 351-354 and Figure 1.

PCT International Search Report and Written Opinion dated May 9, 2014, for PCT/US2013/077356.

PCT International Search Report and Written Opinion dated Jul. 8, 2014, for PCT/US2014/028323.

PCT International Search Report and Written Opinion dated Sep. 29, 2015, for PCT/US2015/037823.

PCT International Search Report and Written Opinion dated Sep. 30, 2015, for PCT/US2015/037828.

PCT International Search Report and Written Opinion dated Feb. 1, 2016, for PCT/US2015/050789.

European Partial Search Report dated Oct. 24, 2016, for 14762269.0.

Bonsignore, Craig S., "Open Stent Design: Design and analysis of self expanding cardiovascular stents", CreateSpace Independent Publishing Platform, Nov. 2012.

Chandrakasan et al., "Next Generation Micro-Power Systems", 2008 Symposium on VLSI Circuits Digest of Technical Papers, pp. 1-5.

Kroft, Steve, "The Data Brokers: Selling your Personal Information" pp. 1-8, extracted from Google on Sep. 4, 2014 is a script from "The Data Brokers" aired on Mar. 9, 2014 on 60 Minutes CBS.

Loh, N.C. et al., "Sub-10 cm3 Intererometric Accelerometer with Nano-g Resolution", J. Microelectromechanical Sys., 11:3, Jun. 2002, pp. 182-187.

Polla, D.L. et al., "Microdevices in Medicine", Ann. Rev. Biomed. Eng., 2000, 02:551-576.

Singh, U.K. et al., "Piezoelectric Power Scavenging of Mechanical Vibration Energy", Australian Mining Technology Conference, October 204, 2007, pp. 111-118.

Yeh, R. et al., "Single Mask, Large Force, and Large Displacement Electrostatic Linear Inchworm Motors", J. Microelectromechanical Sys,. 11:4, Aug. 2002, pp. 330-336.

Yun, K.S. et al., "A Surface-Tension Driven Micropump for Low-voltage and Low-power Operations", J. Microelectromechanical Sys., 11:5, Oct. 2002, pp. 454-461.

* cited by examiner

☐ Contact Sensor
△ Pressure Sensor
○ Position Sensor/Location Marker
☆ Chemical Sensor
◇ Air Flow/Motion Sensor

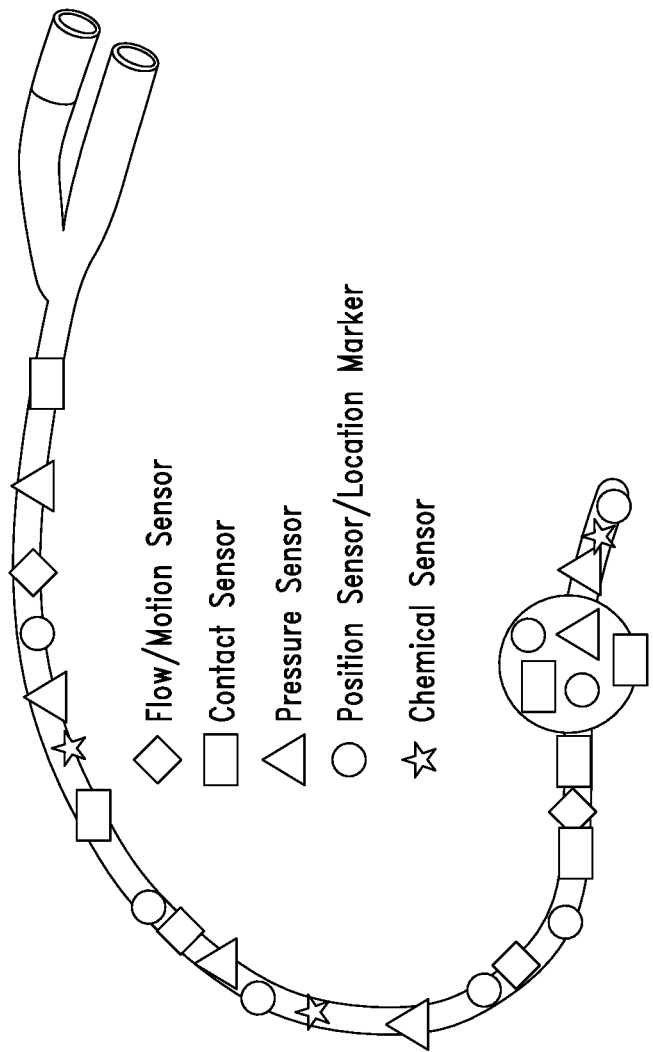
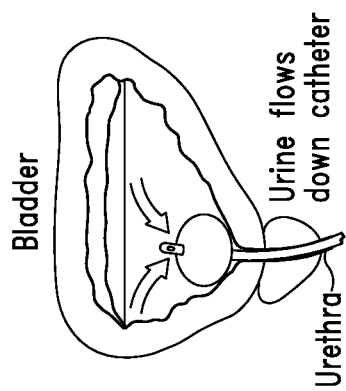
FIG. 16A
FIG. 16B

DEVICES, SYSTEMS AND METHODS FOR USING AND MONITORING TUBES IN BODY PASSAGEWAYS

CROSS-REFERENCE TO RELATED APPLICATION

This application is a Continuation of U.S. application Ser. No. 16/671811, filed Nov. 1, 2019, which is a Continuation of U.S. application Ser. No. 15/320,275, filed Jun. 25, 2015, which is a national phase under 35 U.S.C. § 371 of International Application No. PCT/US2015/037823, filed Jun. 25, 2014, and claims the benefit under 35 U.S.C. § 119(e) of U.S. Provisional Patent Application No. 62/017,086, filed Jun. 25, 2014, each application is incorporated herein by reference in its entirety.

FIELD OF THE INVENTION

The present invention relates generally to medical and surgical tubes that may be implanted in body passageways, and more specifically, to devices and methods for monitoring the placement, efficacy, and performance of a wide variety of tubes (e.g. catheters, chest tubes, drains, endotracheal tubes, urinary catheters, central lines, hemodialysis and bypass grafts).

BACKGROUND

A wide variety of tubes or 'tube-like' devices are utilized in common medical procedures. For example, tubes can be utilized to: 1) bypass an obstruction (e.g., in the case of Coronary Artery Bypass Grafts, or "CABG" or peripheral bypass grafts) or open up an obstruction (balloon dilation catheters, angioplasty balloons); 2) to relieve pressure or obstructions (e.g., shunts, drainage tubes and drainage catheters); 3) to restore or support anatomical structures (e.g., endotracheal tubes, tracheostomy tubes, urinary catheters and feeding tubes); and 4) for vascular access (e.g., CVC catheters and hemodialysis catheters). However, such tubes are susceptible to a wide variety of complications, including for example, infection and blockage.

One example of commonly used medical tubes are catheters. Catheters are thin tubes that are commonly used for a wide variety of medical conditions, and in a wide variety of medical procedures. Typically, they are inserted into a body cavity, lumen, duct, or vessel, which may be naturally occurring (e.g., a blood vessel, urinary tract, gastrointestinal tract, etc.), or artificially created (e.g., by way of an accident, disease, infection, or surgical procedure). Catheters are often inserted into the body by first advancing a flexible, metallic guidewire into the desired anatomical location; the catheter is then placed over the guidewire and maneuvered into its final position. In this manner they can, depending on the indication or procedure, allow for drainage (bile, urine, pus, serous fluids, etc.), administration of fluids (e.g., saline solutions, drugs, etc.), provide access for medical and surgical procedures (peritoneal dialysis, hemodialysis, etc.), provide access for various medical or surgical instruments, and/or of themselves be utilized to perform a wide variety of surgical procedures.

Catheters can be composed of a wide variety of materials (including for example metal such as nitinol), although most are made from polymers. Typical polymers that are used in the construction of catheters include silicone, nylon, polyurethane, and polyethylene terephthalate. Catheters may be composed of bio-degradable or erodible polymers, non-biodegradable polymers, or some combination of these. Guidewires can be composed of a variety of materials but are typically made of metals such as stainless steel, nitinol, titanium or some combination of these.

Representative examples of common catheters are provided in FIG. 1. FIG. 1A illustrates a variety of representative Foley catheters, which are used to allow drainage of the urinary bladder. FIG. 1B depicts several representative balloon catheters of different sizes that show expansion of the balloon portion of the catheter. FIG. 1C illustrates a variety of different balloon catheters. FIG. 1D illustrates a ureteral catheter.

Unfortunately, when a guidewire and/or a catheter is inserted, various complications may arise during the procedure (whether surgical, or non-surgical procedures such as the placement of a urinary catheter) or after the catheter has been implanted. For example, during a surgical procedure, the surgeon may wish to confirm correct anatomical placement and alignment of the guidewire and then the correct anatomical placement and alignment of the catheter and/or any motion/movement between the catheter and the surrounding tissue so that adjustments can be made during the procedure. In addition, to the extent the catheter is utilized in a surgical procedure to deliver another medical device, a physician may wish to confirm the correct placement and/or deployment of a device (such as a stent), or the delivery a desired medical device to its desired anatomical location. Post-procedure, the patient may experience inflammation and pain if there is slight movement of the catheter, the catheter can potentially migrate from the placement site and cease to be effective, the lumen of the catheter can become obstructed by blood clots, "stones" (urinary or biliary), foreign bodies or other tissue debris, and in some cases become infected or covered in biofilm.

The present invention discloses novel tubes (e.g., catheters, endotracheal or chest tubes, bypass grafts, balloon catheters, urinary catheters, central lines and dialysis catheters), as well as related delivery devices (e.g., guidewires) which overcome many of the difficulties of previous tube-like devices, methods for constructing and monitoring these novel devices, and further provides other related advantages.

SUMMARY

Briefly stated, a wide variety of tubes (e.g., catheters, endotracheal or chest tubes, bypass grafts, balloon catheters, urinary catheters, central lines and dialysis catheters), as well as related delivery devices (e.g., guidewires) are provided with a number of sensors to monitor the integrity, patency and efficaciousness of the device.

Within one embodiment, the medical tube or device is a bypass graft, endotracheal or chest tube, balloon catheter, central line, dialysis catheter, urinary catheter or a catheter, along with optionally, a guidewire. The sensors may be positioned on the inside of the bypass graft, endotracheal or chest tube, balloon catheter, central line, dialysis catheter, urinary catheter or guidewire or catheter, within the body of the device, on the outer surface (or surfaces) of the device, between the device, (e.g., guidewire and catheter) and any device it might carry (e.g., a stent) or be associated with (e.g., another medical device). In addition, in the case of multi-lumen or multi-channel catheters, one or more sensors may be placed between the various channels of the catheter over time. When the phrase "placed in a medical tube" or "placed in a device" (or medical device) (whether that tube or device is, for example, a catheter, catheter and guidewire, chest or endotracheal tube, or bypass graft, balloon catheter, central line, dialysis catheter, urinary catheter) is utilized, it should be understood to refer to any of the above embodiments, unless the context of the usage implies otherwise. Within certain embodiments, the sensors are of the type that are passive and thus do not require their own power supply.

A wide variety of sensors can be utilized within the present invention, including for example, fluid pressure sensors, contact sensors, position sensors, accelerometers, vibration sensors, pulse pressure sensors, liquid (e.g., blood) volume sensors, liquid (e.g., blood) flow sensors, liquid (e.g., blood, urine) chemistry sensors, liquid (e.g., blood, urine) metabolic sensors, mechanical stress sensors, and temperature sensors. Within one embodiment the sensor can be connected with other medical devices that can be utilized to delivery one or more drugs. Within other embodiments the one or more sensors can be a wireless sensor, and/or a sensor that is connected to a wireless microprocessor.

Within particularly preferred embodiments a plurality of sensors are positioned on the device (e.g., catheter and/or guidewire, bypass graft, endotracheal or chest tube, balloon catheter, central line, dialysis catheter, urinary catheter), and within yet other embodiments more than one type of sensor is positioned on the device. Within other related embodiments the plurality of sensors are positioned on or within the device at a density of greater than 1, 2, 3, 4, 5, 6, 7, 8, 9, 10 or 20 sensors per square centimeter. Within other embodiments the plurality of sensors are positioned on or within the device at a density of greater than 1, 2, 3, 4, 5, 6, 7, 8, 9. 10 or 20 sensors per cubic centimeter. Within either of these embodiments there can be less than 50, 75, 100, or 200 sensors per square centimeter, or per cubic centimeter.

Within other embodiments of the invention each assembly has a unique device identification number. Within further embodiments one or more (or each) of the sensors have a unique sensor identification number. Within yet other embodiments one or more (or each) of the sensors is uniquely defined within a specific position on or within the device.

According to various embodiments, sensors are placed at different locations in a tube (e.g., catheter (and/or guidewire), bypass graft, endotracheal or chest tube, balloon catheter, central line, dialysis catheter, urinary catheter) in order to monitor the operation, movement, medical imaging (both catheter, guidewire and surrounding tissues), function, wear, flow, patency, performance, potential side effects, medical status of the patient and the medical status of the catheter (and/or guidewire) and its interface with the live tissue of the patient. Live, continuous, in situ, monitoring of patient activity, patient function, device activity, device function, device patency, performance, placement, surface characteristics (flow and chemical content of fluids moving over or through a surface of the device); presence of inflammatory tissues, bacteria or biofilm on the surface etc.), device forces and mechanical stresses, device and surrounding tissue anatomy (imaging), mechanical and physical integrity of the catheter, and potential side effects is provided. In addition, information is available on many aspects of the device and its interaction with the patient's own body tissues, including clinically important measurements not currently available through physical examination, medical imaging and diagnostic medical studies.

According to one embodiment, the sensors provide evaluation data of any motion, movement and/or migration of the medical device during and after placement. Motion sensors and accelerometers can be used to accurately determine the movement of the medical device during physical examination and during normal daily activities between visits. Motion sensors and accelerometers can also be used to accurately determine the movement of the medical device during placement by the physician.

According to another embodiment, contact sensors are provided between the medical device) and the surrounding tissue. In other embodiments, vibration sensors are provided to detect the vibration between the medical device and the surrounding tissue. In other embodiments, strain gauges are provided to detect the strain between a catheter (and/or guidewire) and the surrounding tissue. Sudden increases in strain may indicate that too much stress is being placed on the catheter (and/or guidewire), which may increase damage to the surrounding body tissues or even result in perforation of the body lumen that is being instrumented.

According to other embodiments, accelerometers are provided which detect vibration, shock, tilt and rotation. According to other embodiments, sensors for measuring surface wear, such as contact or pressure sensors, may be embedded at different depths within the medical device in order to monitor contact of the catheter with vessel walls, or degradation of the medical device over time (e.g., in the context of a biodegradable vascular or ureteral catheter). In other embodiments, position sensors, as well as other types of sensors, are provided which indicate movement or migration of the medical device in actual use over a period of time.

According to other embodiments, fluid pressure sensors, pulse pressure sensors, liquid (e.g., blood, urine) volume sensors, liquid (e.g., blood, urine) flow sensors, liquid (e.g., blood, urine) chemistry sensors, liquid (e.g., blood, urine) metabolic sensors, contact sensors, and temperature sensors are provided which can monitor the surface environment of the catheter/tube in situ (both the luminal and adluminal surface sensors). Important changes to the luminal surface such as clotting, obstruction (biliary and urinary "stones", inflammatory tissue, fibrous tissue), infection (bacteria, fungus, pus, white blood cells, biofilm, etc.), narrowing (stenosis, restenosis), increased pressure and changes in flow rates through the catheter/tube can be identified in this manner. Also of great value in the continuous monitoring of patient function, status and health are changes in the content (for example: protein, albumin and enzymes; white cells, red cells, hematocrit, cellular casts, bacteria) and/or chemistry (for example: glucose, protein, calcium, nitrite, electrolytes, phosphate, hCG, hemoglobin, ketones, bilirubin, urobiligen, creatinine, urea nitrogen, catecholamines, dopamine, cortisol, specific gravity, osmolality, pH, crystals, liver enzymes, cardiac enzymes, blood lipids, oxygen levels, illicit drug levels, etc) of the fluids (blood, urine, bile, GI contents, drainage fluids, etc.) flowing through the catheter/tube. In some instances, adluminal surface sensors (fluid pressure sensors, pressure sensors, liquid volume sensors, liquid flow sensors, liquid chemistry sensors, liquid metabolic sensors, contact sensors) are critical for monitoring changes to the outer catheter/tube surface in order to identify abnormalities due to increased pressure (from the presence of a clot, mass, or abscess; leakage; kinking; inadvertent placement or migration into an artery), improper flow (fluids "bypassing" or circumventing the medical tube (e.g., leakage of a catheter), unwanted movement/position/contact (migration into non-target tissues), changes in the chemistry of the fluids around the medical tube (bleeding, leakage, formation of a fibrin sheath, biofilm or infection) and/or changes in the contact between the medical tube and the surrounding tissues (incorrect placement, formation of scar tissue, encapsulation by inflammatory tissue or biofilm, abscess formation).

Within further embodiments, the medical tube or device can contain sensors at specified densities in specific locations. For example, the medical tube or device can have a density of sensors of greater than one, two, three, four, five, six, seven, eight, nine, or ten sensors (e.g., accelerometers (acceleration, tilt, vibration, shock and rotation sensors), pressure sensors, contact sensors, position sensors, chemical sensors, tissue metabolic sensors, mechanical stress sensors and temperature sensors, or any combination of these) per square centimeter of the device. Within other embodiments, the medical tube or device can have a density of sensors of greater than one, two, three, four, five, six, seven, eight, nine, or ten sensors [e.g., accelerometers (acceleration, tilt, vibration, shock and rotation sensors)], pressure sensors, contact sensors, position sensors, chemical sensors, tissue metabolic sensors, mechanical stress sensors and temperature sensors, or any combination of these) per cubic centimeter of the device.

Within certain embodiments of the invention, the medical tube or device is provided with a specific unique identifying number, and within further embodiments, each of the sensors on, in or around the medical tube or device each have either a specific unique identification number, or a group identification number (e.g., an identification number that identifies the sensor as accelerometers (acceleration, tilt, vibration, shock and rotation sensors), pressure sensors, contact sensors, position sensors, chemical sensors, tissue metabolic sensors, mechanical stress sensors and temperature sensors). Within yet further embodiments, the specific unique identification number or group identification number is specifically associated with a position on, in or around the medical tube or device.

Within other aspects of the invention methods are provided for monitoring an implanted medical tube or device comprising the steps of transmitting a wireless electrical signal from a location outside the body to a location inside the body; receiving the signal at a sensor positioned on, in or around an medical tube or device (and/or guidewire) located inside the body; powering the sensor using the received signal; sensing data at the sensor; and outputting the sensed data from the sensor to a receiving unit located outside of the body.

Within other aspects of the invention methods are provided for imaging a medical tube or device as provided herein, comprising the steps of (a) detecting the location of one or more sensors in a medical tube or device, associated medical device (e.g., a stent, guidewire and/or associated medical instrument); and (b) visually displaying the location of said one or more sensors, such that an image of the medical tube or device is created. Within various embodiments, the step of detecting may be done over time, and the visual display may thus show positional movement over time. Within certain preferred embodiments the image which is displayed is a three-dimensional image. Within preferred embodiments the various images may be collected and displayed in a time-sequence (e.g., as a moving 2D or 3D image or 'movie-like' image).

The imaging techniques provided herein may be utilized for a wide variety of purposes. For example, within one aspect, the imaging techniques may be utilized during a surgical procedure in order to ensure proper placement and working of the medical tube or device (and/or guidewire). Within other embodiment, the imaging techniques may be utilized post-operatively in order to examine the medical tube or device, and/or to compare operation and/or movement of the device over time.

The integrity of the medical tube or device can be wirelessly interrogated and the results reported on a regular basis. This permits the health of the patient to be checked on a regular basis or at any time as desired by the patient and/or physician. Furthermore, the medical tube or device can be wirelessly interrogated when signaled by the patient to do so (via an external signaling/triggering device) as part of "event recording"—i.e. when the patient experiences a particular event (e.g. pain, injury, increased or reduced drainage, etc.) she/he signals/triggers the device to obtain a simultaneous reading in order to allow the comparison of subjective/symptomatic data to objective/sensor data. Matching event recording data with sensor data can be used as part of an effort to better understand the underlying cause or specific triggers of a patient's particular symptoms. Hence, within various embodiments of the invention methods are provided for detecting and/or recording an event in a subject with one of the medical tube or devices provided herein, comprising interrogating the medical tube or device at a desired point in time. Within one aspect of the invention methods are provided for detecting and/or recording an event in a subject with a medical tube or device as provided herein, comprising the step of interrogating at a desired point in time the activity of one or more sensors within the medical tube or device, and recording said activity. Within various embodiments, they may be accomplished by the subject and/or by a health care professional. Within related embodiments, the step of recording may be performed with one or more wired devices, or, wireless devices that can be carried, or worn (e.g., a cellphone, watch or wristband, and/or glasses).

Within further embodiments, each of the sensors contains a signal-receiving circuit and a signal output circuit. The signal-receiving circuit receives an interrogation signal that includes both power and data collection request components. Using the power from the interrogation signal, the sensor powers up the parts of the circuitry needed to conduct the sensing, carries out the sensing, and then outputs the data to the interrogation module. The interrogation module acts under control of a control unit which contains the appropriate I/O circuitry, memory, a controller in the form of a microprocessor, and other circuitry in order to drive the interrogation module. Within yet other embodiments the sensor (e.g., accelerometers (acceleration, tilt, vibration, shock and rotation sensors), pressure sensors, contact sensors, position sensors, chemical sensors, tissue/fluid metabolic sensors, mechanical stress sensors and temperature sensors) are constructed such that they may readily be incorporated into or otherwise mechanically attached to the medical tube or device (e.g., by way of a an opening or other appendage that provides permanent attachment of the sensor to the medical tube or device) and/or readily incorporated into body of the medical tube or device.

Within yet other aspects of the invention methods devices are provided suitable for transmitting a wireless electrical signal from a location outside the body to a location inside the body; receiving the signal at one of the aforementioned sensors positioned on, in or around a medical tube or device located inside the body; powering the sensor using the received signal; sensing data at the sensor; and outputting the sensed data from the sensor to a receiving unit located outside of the body. Within certain embodiments the receiving unit can provide an analysis of the signal provided by the sensor.

The data collected by the sensors can be stored in a memory located within the medical tube or device, or on an associated device (e.g., an associated medical device, or an external device such as a cellphone, watch, wristband, and/or glasses). During a visit to the physician, the data can be downloaded via a wireless sensor, and the doctor is able to obtain data representative of real-time performance of the medical tube or device, and any associated medical device.

The advantages obtained include more accurate monitoring of the medical tube or device and permitting medical reporting of accurate, in situ, data that will contribute to the health of the patient. The details of one or more embodiments are set forth in the description below. Other features, objects and advantages will be apparent from the description, the drawings, and the claims. In addition, the disclosures of all patents and patent applications referenced herein are incorporated by reference in their entirety.

BRIEF DESCRIPTION OF THE DRAWINGS

FIG. 16A illustrates placement of a Foley catheter in the bladder. FIG. 16B illustrates one embodiment wherein a variety of sensors are placed on and/or within a Foley catheter.

DETAILED DESCRIPTION OF THE INVENTION

Figure 1A:
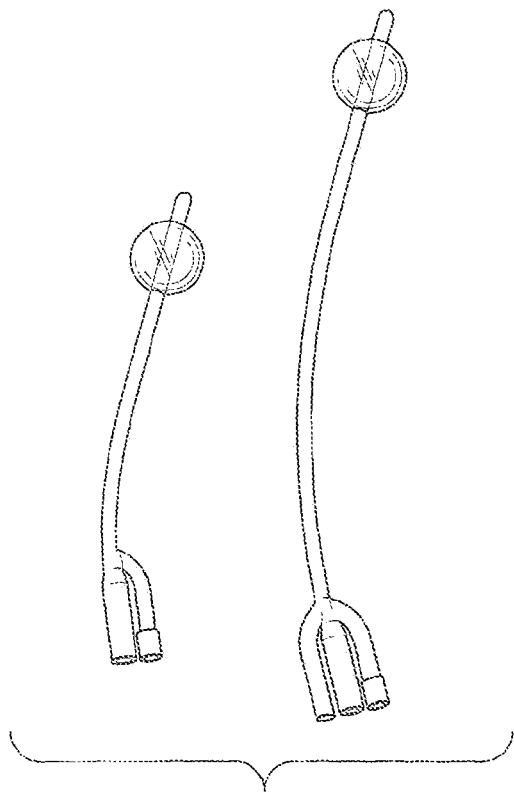
FIG. 1A illustrates a variety of representative Foley catheters, which are used to allow drainage of the bladder.

Briefly stated the present invention provides a variety of catheters and medical tubes that can be utilized to monitor the placement, performance, integrity and/or efficaciousness of the catheter or medical tube, and any associated medical device (e.g., stent, guidewire, and/or other associated medical instrument). Prior to setting forth the invention however, it may be helpful to an understanding thereof to first set forth definitions of certain terms that are used hereinafter.

Medical "tube" refers to a generally cylindrical body, and as utilized herein, can be used in a wide variety of medical procedures (e.g., the tubes are generally sterile, non-pyrogenic, and/or suitable for use and/or implantation into humans). For example, tubes can be utilized to: 1) bypass an obstruction (e.g., in the case of Coronary Artery Bypass Grafts, or "CABG" and peripheral bypass grafts) or open up an obstruction (balloon dilation catheters, angioplasty balloons); 2) to relieve pressure (e.g., shunts, drainage tubes and drainage catheters, urinary catheters); 3) to restore or support anatomical structures (e.g., endotracheal tubes, tracheostomy tubes, and feeding tubes); and 4) for access (e.g., CVC catheters, peritoneal and hemodialysis catheters). Representative examples of tubes include catheters (as discussed in more detail below), auditory or Eustachian tubes, drainage tubes, tracheotomy tubes (e.g., Durham's tube), endobronchial tubes, endotracheal tubes, esophageal tubes, feeding tubes (e.g., nasogastric or NG tubes), stomach tubes, rectal tubes, colostomy tubes, and a wide variety of grafts (e.g., bypass grafts).

Tubes may be composed of synthetic materials (e.g., silicone, polyurethane and rubber), composed of non-synthetic components (e.g., harvested vein and artery grafts for bypass), or some combination of these [e.g., artificial blood vessels having a synthetic polymer scaffold, and naturally occurring cells (e.g., fibroblasts) which produce matrix materials for the vessel (e.g., collagen)].

"Catheter" as that term is utilized herein, refers to a thin tube that is commonly used for a wide variety of medical conditions, and in a wide variety of medical procedures. Typically, they are inserted into a body cavity, lumen, duct, or vessel. Catheters are often inserted into the body by first advancing a flexible, metallic guidewire to the desired anatomical location; the catheter is then placed over the guidewire and maneuvered into position and the guidewire is then removed. In this manner they can, depending on the indication or procedure, allow for drainage, administration of fluids (e.g., saline solutions, drugs, etc.), provide access for various medical or surgical instruments, and/or of themselves be utilized to perform a wide variety of surgical procedures (such as balloon catheters used to dilate an obstructed body passageway). Catheters may be used either temporarily, or for extended periods of time (even permanently), and may have one, two, three, or more lumens or channels.

Catheters may be composed of a wide variety of materials (including for example metals such as nitinol), although most are made from polymers. Catheters may be made of either biodegradable or non-biodegradable polymers (or combinations of these). Typical polymers that are used in the construction of catheters include silicone, nylon, polyurethane, and polyethylene terephthalate. As will be readily evident given the disclosure provided herein, the catheter can be designed suitable to the intended use, and may be designed in a wide variety of forms and shapes (see e.g., FIG. 1 for both non-balloon and balloon based catheters).

Catheters can be utilized for a wide variety of indications and procedures, including for example, for 1) draining fluids or eliminating obstructions through the placement of catheters via natural body orifices, such as: draining the urinary tract (e.g., the bladder or kidney) via the urethra with Foley catheters, intermittent (Robinson) catheters and ureteric catheters; accessing the GI tract through anal catheters, and suction catheters; reaching the respiratory system through the nose and mouth with pulmonary catheters; entering the reproductive system via the vagina (female) or urethra (male); 2) draining bodily fluids or relieving an obstruction through a surgically created access into an anatomical space or cavity; e.g., peritoneal catheters (placed in the abdominal cavity for ascites, dialysis), chest tubes (placed in the pleural space for pneumothorax, pleural effusion, chylothorax, infection), pericardial drainage tubes (in the heart), CNS drainage catheters or shunts (placed in the cerebrospinal fluid for hydrocephalus, infection, inflammation, obstruction); 3) drainage catheters which are surgically placed percutaneously or intraoperatively to drain collections of sterile fluid or abscesses elsewhere [can be placed virtually anywhere, including the thorax (heart, lungs), abdomen (liver, biliary drainage catheters), knees, hips, urinary tract (ureters, kidneys, prostate, bladder), reproductive tract (uterus, fallopian tubes), GI tract (anal fistulas, other fistulas, abcesses, stomas, colostomies), soft tissues (abscesses, seromas, compartment syndromes) to name a few]; 4) intervenous [e.g. peripheral i.v.'s, central venous catheters (CVCs), peripherally-inserted central venous catheters (PICCs), arterial (e.g. hemodialysis access grafts and catheters, arterial catheters), and peritoneal (e.g. peritoneal dialysis catheters, peritoneal catheters) catheters that are placed for the administration of fluids (e.g., intravenous administration of fluids, medication, direct administration of a desired substance (e.g., a drug) to a desired location), access, dialysis or nutrition (nasogastric tubes, feeding tubes, total parental nutrition tubes, gastric tubes); 5) catheters placed for the implementation of a medical or surgical procedure or device [e.g., coronary angioplasty, peripheral angioplasty, angiography, dilation of an artery and/or placement of a stent, balloon septostomy, balloon sinuplasty, catheter-based ablation, balloon dilation catheters (esophageal, biliary, tracheal, bronchial, urethral, etc.)]; and 6) catheters placed for the direct measurement of a biological function or value (e.g., arterial or venous blood pressure, cardiac function, and intracranial pressure).

Commonly available catheters include Foley-catheters for the drainage of urine, ureteral catheters, central venous catheters (CVCs, PICCs, ports) for the administration of drugs and fluids, and Swan-Ganz catheters utilized principally for diagnostic purposes in the pulmonary artery. Representative examples of catheters are described in U.S. Pat. Nos. 8,491,569, 8,469,989, 8,460,333, 8,359,082, 8,246,568, 8,285,362, 8,257,420, 8,317,713, 8,328,829, 8,262,653, 6,966,914, 5,989,213, 5,509,897, 4,772,268, and U.S. Publication Nos. 2012/0310158, 2012/0283641, 2012/0239032, 2012/0253276, all of which are incorporated by reference in their entirety. Within one limited embodiment of the invention a balloon catheter which is utilized to deploy a stent or at stent graft can be optionally excluded, to the extent said exclusion is specifically stated or claimed.

Representative examples of intravascular catheters and balloon dilation catheters (including drug delivery catheters and balloon catheters are described in U.S. Pat. Nos. 5,180,366; 5,171,217; 5,049,132; 5,021,044; 6,592,568; 5,304,121; 5,295,962; 5,286,254; 5,254,089; 5,112,305, 5,318,531, 5,336,178, 5,279,565, 5,364,356, 5,772,629, 5,810,767, 5,941,868, 5,362,309, 5,318,014, 5,315,998, 5,304,120, 5,282,785, 5,267,985, 5,087,244, 5,860,954, 5,843,033, 5,254,089, 5,681,281, 5,746,716, 6,544,221, 6,527,739, 6,605,056, 6,190,356, 5,279,546, 5,236,424, 5,226,888; 5,181,911, 4,824,436, 4,636,195, 5,087,244, 6,623,452, 5,397,307, 4,636,195, 4,994,033, 5,362,309 and 6,623,444; U.S. patent application Publication Nos. 2002/0138036, 2002/0068869, 2005/0186243; and PCT Publication Nos. WO 01/15771; WO 93/08866, WO 92/11890, WO 92/11895, WO 94/05361; WO 96/04955 and WO 96/22111, all of which are incorporated by reference in their entirety.

"Guidewire" refers to a medical device which is utilized to position another medical device (e.g., an intravenous catheter, endotracheal tube, central venous line, balloon catheter, or gastric feeding tube), or to localize a tumor (e.g., during a breast biopsy). Representative examples of guidewires are described in U.S. Pat. Nos. 4,787,884, 5,911,734, 5,910,154, 6,676,682, 6,936,065, 6,964,673, and 7,691,123 and U.S. Publication Nos. 2006/0100694, and 2007/0027522, all of which are incorporated by reference in their entirety.

"Stent" refers to a medical device that can be utilized to hold open body structures and/or passages, and can be utilized to treat and/or prevent a wide variety of diseases and/or conditions resulting from lumen narrowing or obstruction; whether due to an injury or external compression of the vessel wall (a benign or malignant tumor, abscess, cyst), a disease process occurring within the vessel wall (e.g., cancer, atherosclerosis, inflammation, scarring or stenosis), and/or a disease processes occurring on the surface (or in the lumen) of the vessel wall (thrombus, atherosclerosis, restenosis, tumor growth, inflammation and scarring, biliary and urinary "stones", mucous impaction, infection, etc.), and/or an operation or other medical intervention. Stents containing sensors are described in more detail in U.S. Provisional 61/787,861, entitled "Stent Monitoring Assembly and Method of Use Thereof", which is incorporated by reference in its entirety.

The medical devices (e.g., catheter and/or guidewire, bypass graft, endotracheal or chest tube, balloon catheter, central line, dialysis catheter, and urinary catheter) provided herein are preferably sterile, non-pyrogenic, and/or suitable for use and/or implantation into humans. However, within certain embodiments of the invention these medical devices can be made in a non-sterilized environment (or even customized or "printed" for an individual subject), and sterilized at a later point in time.

"Sensor" refers to a device that can be utilized to measure one or more different aspects of a body, of a medical tube or device inserted within a body, and/or the integrity, patency, impact, efficaciousness or effect of the medical tube or device inserted within a body. Representative examples of sensors suitable for use within the present invention include, for example, fluid pressure sensors, contact sensors, position sensors, pulse pressure sensors, liquid (e.g., blood) volume sensors, liquid (e.g., blood, urine) flow sensors, chemistry sensors (e.g., for blood, urine and/or other fluids), metabolic sensors (e.g., for blood, urine and/or other fluids), accelerometers, mechanical stress sensors and temperature sensors. Within certain embodiments the sensor can be a wireless sensor, or, within other embodiments, a sensor connected to a wireless microprocessor. Within further embodiments one or more (including all) of the sensors can have a Unique Sensor Identification number ("USI") which specifically identifies the sensor.

A wide variety of sensors (also referred to as Microelectromechanical Systems or "MEMS", or Nanoelectromechanical Systems or "NEMS", and BioMEMS or BioNEMS, see generally https://en.wikipedia.org/wiki/MEMS) can be utilized within the present invention. Representative patents and patent applications include U.S. Pat. Nos. 7,383,071 and 8,634,928, and U.S. Publication Nos. 2010/0285082, and 2013/0215979. Representative publications include "Introduction to BioMEMS" by Albert Foch, CRC Press, 2013; "From MEMS to Bio-MEMS and Bio-NEMS: Manufacturing Techniques and Applications by Marc J. Madou, CRC Press 2011; "Bio-MEMS: Science and Engineering Perspectives, by Simona Badilescu, CRC Press 2011; "Fundamentals of BioMEMS and Medical Microdevices" by Steven S. Saliterman, SPIE—The International Society of Optical Engineering, 2006; "Bio-MEMS: Technologies and Applications", edited by Wanjun Wang and Steven A. Soper, CRC Press, 2012; and "Inertial MEMS: Principles and Practice" by Volker Kempe, Cambridge University Press, 2011; Polla, D. L., et al., "Microdevices in Medicine," Ann. Rev. Biomed. Eng. 2000, 02:551-576; Yun, K. S., et al., "A Surface-Tension Driven Micropump for Low-voltage and Low-Power Operations," *J. Microelectromechanical Sys.*, 11:5, October 2002, 454-461; Yeh, R., et al., "Single Mask, Large Force, and Large Displacement Electrostatic Linear Inchworm Motors," *J. Microelectromechanical Sys.*, 11:4, August 2002, 330-336; and Loh, N. C., et al., "Sub-10 cm$^3$ Interferometric Accelerometer with Nano-g Resolution," *J. Microelectromechanical Sys.*, 11:3, June 2002, 182-187; all of the above of which are incorporated by reference in their entirety.

Within various embodiments of the invention the sensors described herein may be placed at a variety of locations and in a variety of configurations, on the inside of the medical tube or device, within the body of the medical tube or device, or on the outer surface (or surfaces) of the medical tube or device, between the medical tube or device and any device it might carry (e.g., a stent carried by a delivery catheter or a balloon catheter) or be associated with (e.g., a guidewire, or other medical device). In addition, in the case of multi-lumen devices (such as multi-channel catheters), one or more sensors may be placed between the various channels of the device.

The sensors may be placed in the medical tube or device alone, or in the context of associated medical devices (e.g., a guidewire and/or stent), or in the context of a kit (e.g., a kit for coronary artery catheterization), within a catheter, stent and/or guidewire. For example, within certain embodiments, the medical tube or device, associated medical device (e.g., guidewire or delivery instrument), or kit comprises sensors at a density of greater than 1, 2, 3, 4, 5, 6, 7, 8, 9, 10 or greater than 10 sensors per square centimeter. Within other aspects, the medical tube or device, associated medical device (e.g., guidewire or delivery instrument) or kit comprises sensors at a density of greater than 1, 2, 3, 4, 5, 6, 7, 8, 9, 10 or greater than 10 sensors per cubic centimeter. Within either of these embodiments, there can be less than 50, 75, 100, or 100 sensors per square centimeter, or per cubic centimeter. Within various embodiments, at least one or more of the sensors may be placed randomly, or at one or more specific locations within the catheter, medical device, or kit as described herein.

In various embodiments, the sensors may be placed within specific locations and/or randomly throughout the medical tube or device, associated medical device (e.g., guidewire or delivery instrument) or kit. In addition, the sensors may be placed in specific patterns (e.g., they may be arranged in the pattern of an X, as ovals or concentric rings around the medical tube or device, associated medical device (e.g., guidewire or delivery instrument) or kit.

Representative Embodiments of Catheters and Medical Uses of Sensor Containing Tubes In order to further understand the various aspects of the invention provided herein, the following sections are provided below: A. Medical Tubes and their Use; B. Use of Medical Tubes to Deliver Therapeutic Agent(s); C. Use of a Tube having Sensors to Measure Flow and Flow Obstruction; D. Methods for Monitoring Infection in Medical Tubes; E. Further Uses of Sensor-containing Medical Tubes in Healthcare; F. Generation of Power from Medical Tubes; G. Medical Imaging and Self-Diagnosis of Assemblies Comprising Medical Tubes, Predictive Analysis and Predictive Maintenance; H. Methods of Monitoring Assemblies Comprising Medical Tubes; and I. Collection, Transmission, Analysis, and Distribution of Data from Assemblies Comprising Medical Tubes.

A. Medical Tubes and their Use

A1. Catheters and their Use

A1.1 Balloon Catheters and their Use

Figure 1B:
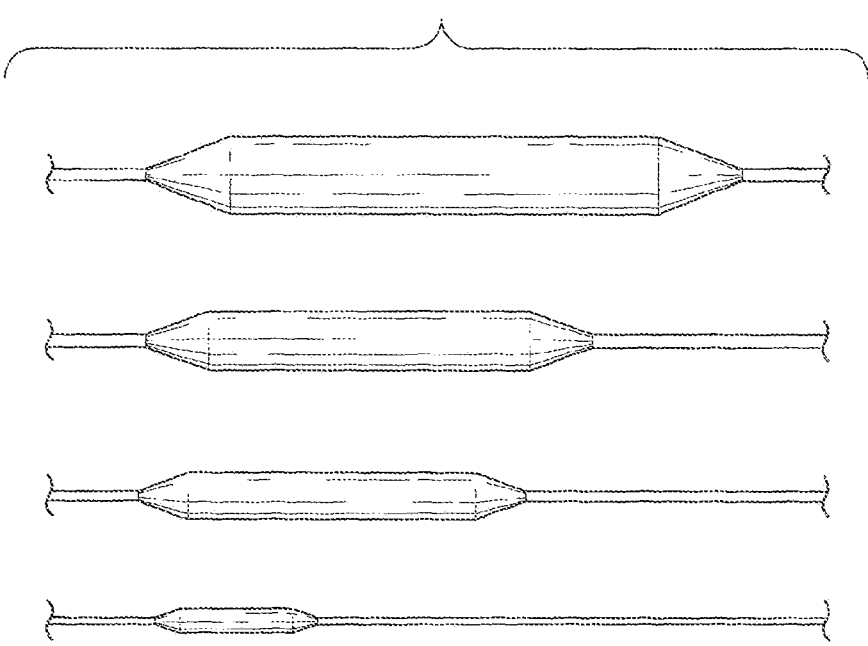
FIG. 1B depicts several representative balloon catheters (such as angioplasty balloon catheters) that shows expansion of the balloon portion of the catheter.
Figure 1C:
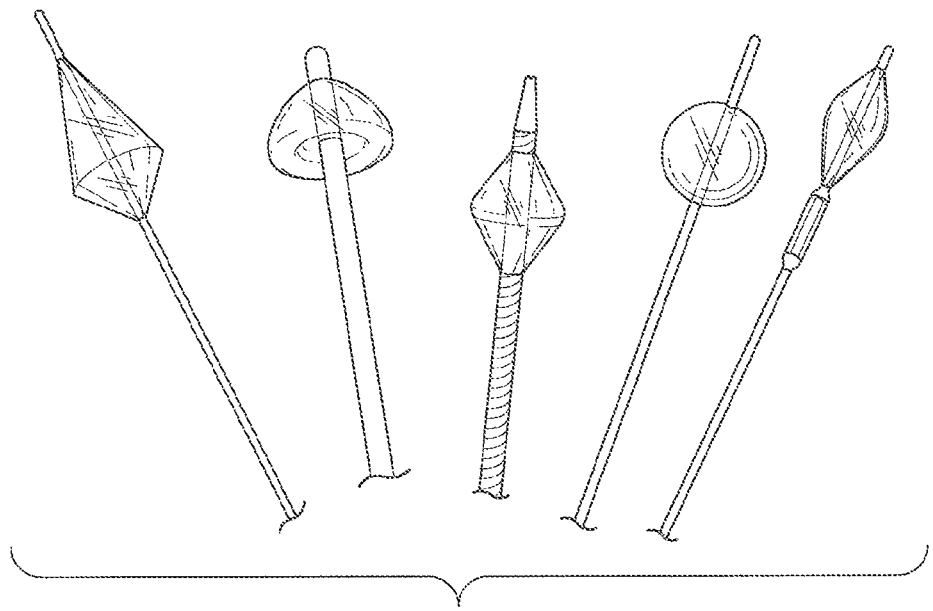
FIG. 1C illustrates a variety of different balloon catheters.
Figure 1D:
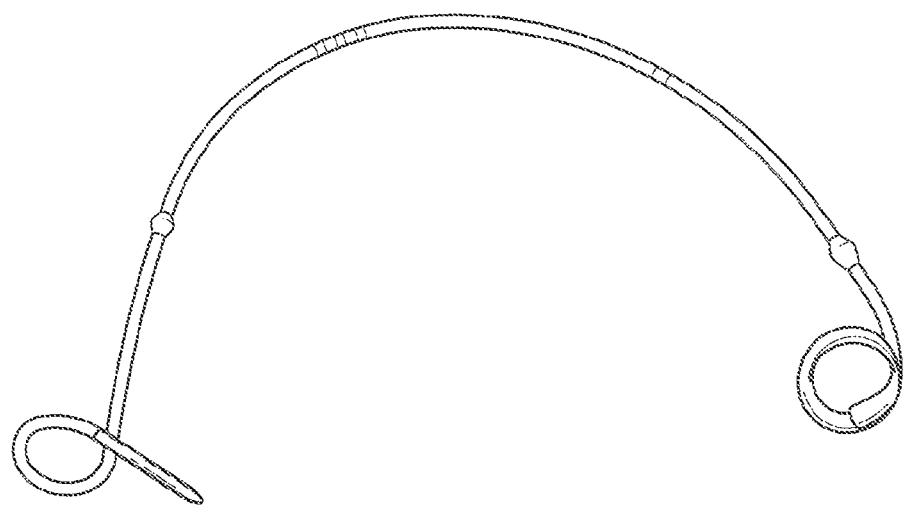
FIG. 1D illustrates a ureteral catheter.
Figure 3:
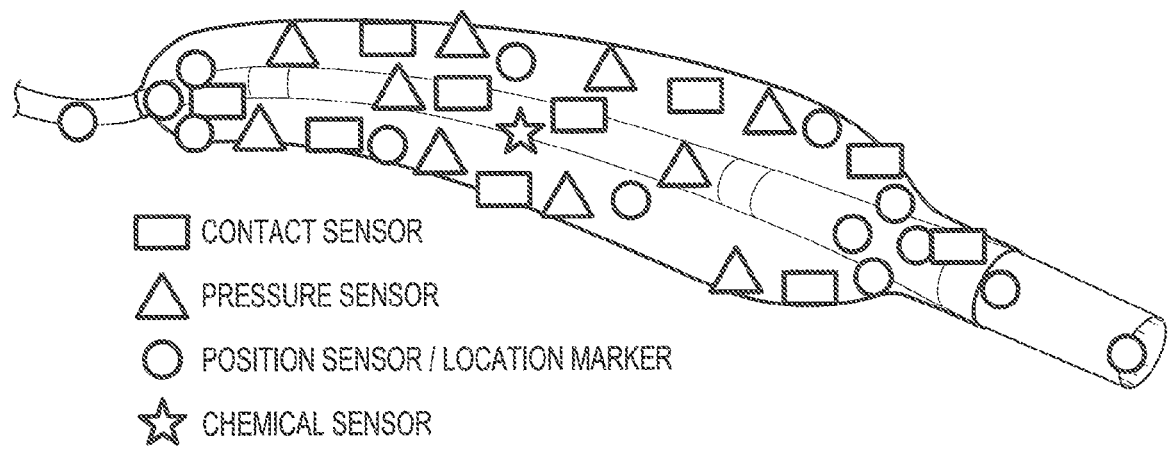
FIG. 3 illustrates one embodiment wherein sensors of various types are deployed throughout a balloon catheter.

As noted above, within various embodiments of the invention balloon catheters, such as those shown in FIGS. 1B and 1C (and their associated medical devices, e.g., stents and/or guidewires), are provided with a variety of the sensors described herein. For example, FIG. 3 illustrates a balloon catheter having one or more sensors positioned in or on the catheter and/or guidewire in order to monitor, in situ, the real-time operation of the catheter, levels of patient function and activity, and the catheter performance acutely and over time. The sensors may be positioned inside the balloon catheter, within the walls of the balloon catheter, or on the outer surface of the balloon catheter. While in certain embodiments contact sensors, pressure sensors, and positions sensors can be utilized as shown in FIG. 3, a wide variety of other sensors can also be placed in, on, or within the catheter, including for example, fluid pressure sensors, accelerometers, vibration sensors, pulse sensors, liquid (e.g., blood) volume sensors, liquid (e.g., blood) flow sensors, liquid (e.g., blood) chemistry sensors, liquid (e.g., blood) metabolic sensors, mechanical stress sensors, and temperature sensors.

Figure 2A:
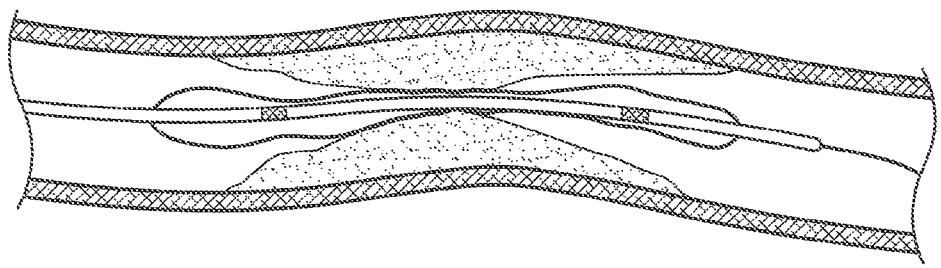
FIG. 2 depicts one representative use of a balloon catheter in a partially blocked vessel, including insertion of the balloon catheter in the blocked vessels (FIG. 2A), expansion of the balloon to dilate the vessel (FIG. 2B), and free movement of fluid through the vessel after removal of the balloon catheter (FIG. 2C).
Figure 2B:
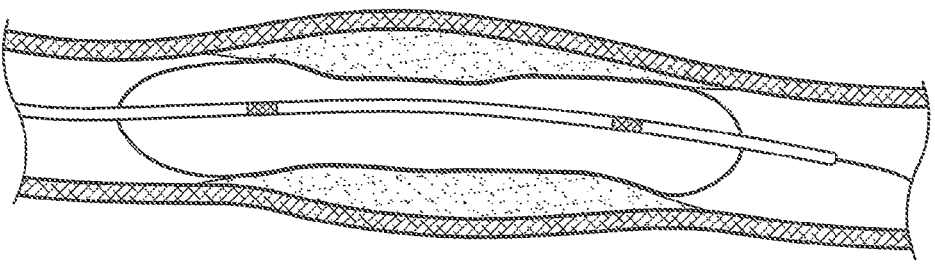
Figure 2C:
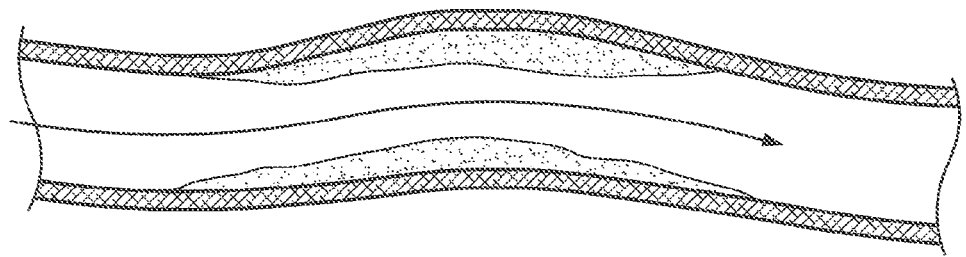

For example, in FIG. 2A, a balloon catheter is inserted via a guidewire into a stenosed artery (such as a coronary artery or peripheral artery). Contact sensors on the balloon can be utilized to monitor contact with the vessel wall during inflation, deployment and deflation. In FIG. 2B, the balloon is expanded, thereby expanding the artery (coronary artery or peripheral artery). Pressure sensors on the balloon can monitor pressure in the balloon, and the pressure which is exerted against the vascular wall. Within preferred embodiments the pressure is monitored and, if needed adjusted in order to prevent injury to the vascular wall due to excessive pressure. The drop in pressure during balloon deflation of the balloon can also be monitored to confirm that it is safe to withdraw the balloon catheter from the treated vascular lesion. Similarly, contact sensors can monitor contact of the balloon with the vessel wall during balloon deflation to confirm that it is safe to withdraw the balloon catheter from the treated vascular lesion. Position sensors can also be utilized in balloon catheters and guidewires, as shown in FIGS. 2A and 2B, in order to assist in placement of the balloon catheter, (and placement of a stent, if desired), and for medical imaging. Position sensors can be utilized to provide an image of vascular anatomy, pre- and post-inflation anatomy, confirmation of full balloon inflation and deflation, confirmation of stent placement and full deployment. FIG. 2C illustrates improved vascular flow due to use of the balloon catheter.

Figure 4A:
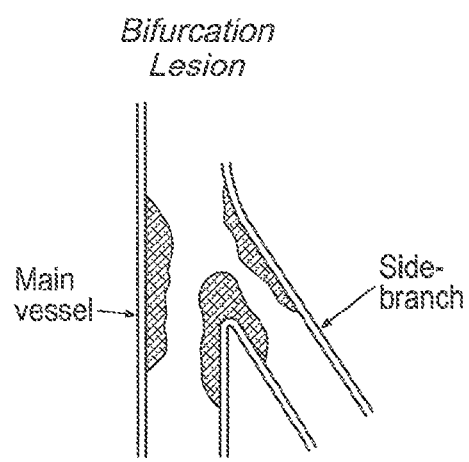
FIGS. 4A and 4B illustrate one embodiment wherein sensors are utilized to assist in deployment of stents during the treatment of a bifurcated lesion in the vasculature.
Figure 4B:
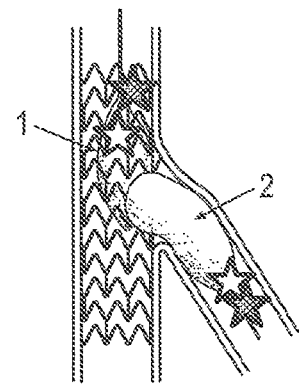

FIGS. 4A and 4B illustrate another embodiment of the invention wherein sensors are utilized to assist the placement of a stent utilizing a balloon catheter. Briefly, FIG. 4A illustrates a site of bifurcation with stenosis occurring at multiple points in the vessel. FIG. 4B illustrates a stent with PTCA. In this case, (potentially "matched" or complimentary) contact sensors can be used to confirm accurate assembly; accelerometers can be used to confirm anatomical location and conformation; position sensors can monitor movement; flow sensors can confirm vascular patency; and pressure/vessel wall sensors can confirm full deployment and accurate vessel sizing. Taken collectively, this sensing information can create a 3-dimensional image of the vascular and stent anatomy and greatly improve the data available from angiography alone. This dramatically increases the chances of accurate, safe and effective deployment of multiple stents in complicated vascular lesions.

It should be readily evident given the disclosure provided herein that the above balloon catheters and associated medical devices containing sensors can be utilized in the management of non-vascular disease. Balloon catheters are used to open up obstructed body passageways and lumens in many other tissues, such as, but not restricted to, the sinuses, respiratory tract, gastrointestinal tract, biliary tract, urinary tract and reproductive tract. While the size, shape and purpose of the balloon catheter (and associated devices) may vary, the type, placement and role of various sensors is analogous to that described above for the vascular system. In summary, a wide variety of sensors may be placed on and/or within balloon catheters and associated devices (such as guidewires) described herein, in order to provide "real time" information and feedback to a health care provider (or a surgeon during a surgical procedure utilizing a balloon to open up an obstructed body passageway), to detect proper placement, anatomy, effective dilation (and elimination of the obstruction), forces exerted on surrounding tissues, balloon inflation and deflation, and to detect the strain encountered in an balloon procedure. For example, the balloon catheters and associated devices (such as guidewires) provided herein can have one or more contact sensors, strain gauge sensors, pressure sensors, fluid pressure sensors, position sensors, accelerometers, shock sensors, rotation sensors, vibration sensors, tilt sensors, pressure sensors, tissue chemistry sensors, tissue metabolic sensors, mechanical stress sensors and temperature sensors. Sensors can be placed at a density of greater than 1, 2, 3, 4, 5, 6, 7, 8, 9, 10 or greater than 10 sensors per square centimeter or at a density of greater than 1, 2, 3, 4, 5, 6, 7, 8, 9, 10 or greater than 10 sensors per cubic centimeter. Within either of these embodiments there can be less than 50, 75, 100, or 100 sensors per square centimeter, or per cubic centimeter.

The above sensors may be continuously monitored in order to provide a 'real-time' data, imaging, and changes in function over the course of the procedure, and to better understand the conditions which balloon catheters are exposed to in the real world.

A1.2 Central Venous Catheters and their Use

Figures 13A, 13B:
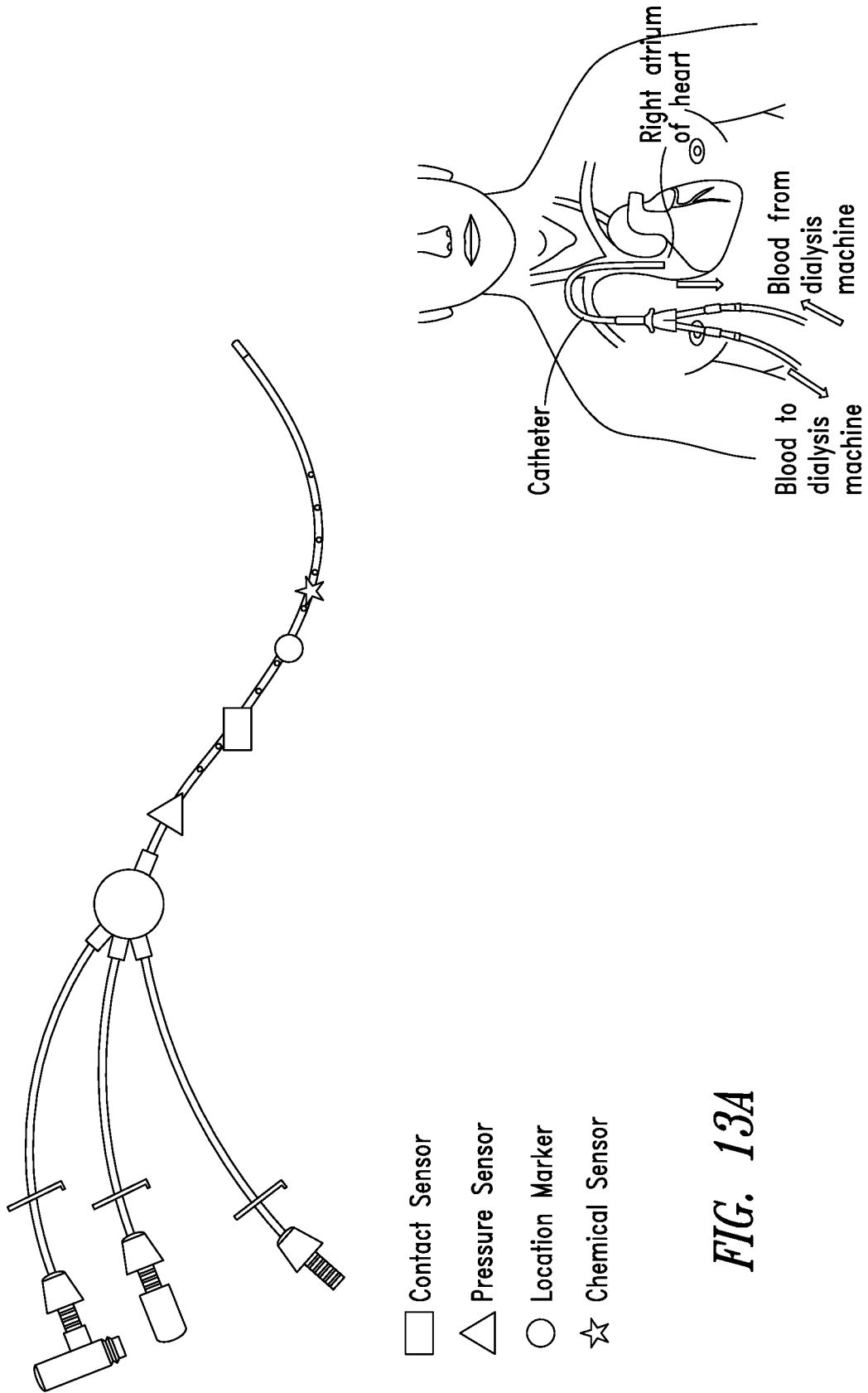
FIG. 13A illustrates one embodiment of sensors on a central venous catheter.
FIG. 13B illustrates one embodiment wherein a central venous catheter is placed into a subject.

Within other embodiments of the invention central venous catheters are provided having a variety of sensors placed thereon (see, e.g., FIG. 13A). Briefly, central venous catheters (also referred to as "central lines", "CVC"s) are catheters that are most typically placed into the great veins of the body [usually the superior vena cava (SVC), or the inferior vena cava (IVC)] via access through the large vein of the neck [e.g., the internal jugular vein), the chest (e.g., the subclavian vein or axillary vein), or the groin (e.g., the femoral vein)] when reliable, longer term vascular access is required. However, CVCs can also be inserted peripherally (e.g., placed into the peripheral vasculature system such as the veins of the arm and then advanced through the venous system until the tip reaches the SVC), and in this instance are commonly referred to as "Peripherally Inserted Central Catheters" or "PICC"s. CVCs are utilized to delivery medication and/or fluids to a subject, to obtain blood for testing, and for measuring pressure (typically at the distal tip of the catheter).

CVCs can be 'non-tunneled' (i.e., fixed at the site of insertion), and 'tunneled' (i.e., passed under the skin from the insertion site, to a separate exit site). One type of catheter similar to a 'tunneled' catheter is a "port", which is similar to a tunneled catheter, but left entirely under the skin. In this case, medicine can be injected directly through the skin into the port, or, if for some types of ports, into a reservoir of the port. The term "Central Venous Catheter" or "CVC" used herein should be interpreted to include PICCs, Ports, Tunneled CVCs and Non-tunneled CVCs.

Common complications of central lines include pneumothorax, central line associated bloodstream infections, thrombosis, hemorrhage, and the formation of hematomas or seromas at the insertion site.

Hence, central venous catheters of the present invention can be utilized which have one or more of the sensors described herein (see e.g., FIG. 13). For example, within one embodiment, central venous catheters of the present invention can have one or more fluid flow sensors. Such sensors can, within various embodiments be located on the inner (luminal) surfaces of the catheter the outer (adluminal or blood contacting) surfaces of the catheter, throughout the catheter, and/or concentrated at the ends (tips) of the catheter. They can be utilized to measure fluid flow through the catheter lumen. By comparing the readings of sensors throughout the catheter, a determination of blockage (and the extent of a blockage; for example from the formation of a fibrin sheath, catheter stenosis, catheter thrombosis, or catheter kinking) can be determined (e.g., there would be decreased luminal fluid flow prior to a narrowing and increased luminal fluid flow following an narrowing; there would be no fluid flow before or after a complete obstruction). The ability to monitor flow rates would be valuable in normal operation and during/after procedural attempts to "reopen" obstructed catheters.

Within other embodiments, pressure sensors can be incorporated into a central venous catheter on the inner (luminal)

wall, outer (abluminal) wall, and/or within the body of the catheter itself. Such sensors are able to measure pressure within or exerted against the catheter wall. Increased pressures can be suggestive of stenosis, thrombosis or kinking upstream from a narrowing or obstructing event, whereas decreased pressures would be seen downstream from a narrowing and (little or) no pressure would be seen downstream from an obstruction. Having the ability to measure pressure throughout the catheter allows for functional monitoring of the central venous catheter (in normal operation and during/after attempts to "reopen" obstructed catheters), and the capability of detection events prior to a complication developing.

Within yet other embodiments, contact sensors can be placed on and throughout the central venous catheter in order to measure contact between the luminal and adluminal surfaces and the surrounding environment. Sustained foreign body contact on either surface could be indicative of the formation of a fibrin sheath, thrombosis, biofilm formation or infection; sustained contact at the tip could indicate that the catheter has become pushed up against the vascular wall and needs to be repositioned. In yet another embodiment, chemical sensors can be placed primarily on the adluminal (blood contacting) surface and also throughout the central venous catheter in order to measure a wide variety of metabolic parameters, including for example: Blood Oxygen content; Blood $CO_2$ content; Blood pH; Blood cholesterol; Blood lipids (HDL, LDL); Blood Glucose; Cardiac enzymes; Hepatic Enzymes; and Kidney Function (BUN, Creatinine, etc.).

Within other embodiments, position sensors can be placed throughout the catheter (e.g., on both the luminal and adluminal surfaces, and within the catheter material itself) in order to allow imaging of the catheter, and detection of changes and/or movement over time. Position sensors are useful during placement of the catheter to ensure advancement into the SVC, but not the right atria of the heart; post-placement, they can be used to determine if the catheter has migrated proximally or distally (into the right atrium) with time.

Within yet other embodiments, chemical and temperature sensors can be utilized to monitor changes in temperature, and/or the presence of an infection or a developing infection.

In summary, a wide variety of sensors may be placed on and/or within the central venous catheters described herein, in order to provide "real time" information and feedback to a health care provider (during a placement, repositioning or "reopening" procedures), to detect proper placement, anatomy, alignment, forces exerted on surrounding tissues, and to detect the strain encountered during placement and subsequent manipulation or repositioning procedures. For example, the central venous catheters (CVCs, PICCs, Ports) provided herein can have one or more contact sensors, strain gauge sensors, pressure sensors, fluid pressure sensors, position sensors, accelerometers, shock sensors, rotation sensors, vibration sensors, tilt sensors, pressure sensors, blood chemistry sensors, blood metabolic sensors, mechanical stress sensors and temperature sensors. Sensors can be placed at a density of greater than 1, 2, 3, 4, 5, 6, 7, 8, 9, 10 or greater than 10 sensors per square centimeter or at a density of greater than 1, 2, 3, 4, 5, 6, 7, 8, 9, 10 or greater than 10 sensors per cubic centimeter. Within either of these embodiments there can be less than 50, 75, 100, or 100 sensors per square centimeter, or per cubic centimeter. The above sensors may be continuously monitored in order to provide a 'real-world' activity, patency, and changes in function over time, to evaluate patient physiology, and to better manage the central line patient.

A1.3 Dialysis Catheters and their Use

Within other embodiments, specialized central venous catheters can be utilized in hemodialysis procedures (typically when dialysis is only needed for a short period of time or as a bridge to permanent dialysis procedures—see later). Briefly, a hemodialysis catheter (or alternatively—"acute dialysis catheter") is a specialized CVC placed into the central circulation that is used for exchanging blood to and from a hemodialysis machine. Typically, the catheter has two lumens, one for venous flow and the other for arterial flow. The arterial lumen withdraws blood from the patient and carries it to the hemodialysis machine, and the venous lumen returns blood to the patient (after the blood has been treated by the dialysis machine). Typically, flow rates of dialysis catheters range from between 200 and 500 milliliters per minute. If patient requires long term dialysis therapy, a 'chronic' dialysis catheter can be utilized, which typically includes a cuff that is buried beneath the skin (and which is believed to aid as a barrier to infection. Common complications of hemodialysis catheters include fibrin sheath formation, clotting, biofilm formation, infection and kinking. Hence, hemodialysis catheters of the present invention can be utilized which have one or more of the sensors described herein (such as our seen in FIG. 13). For example, within one embodiment hemodialysis catheters of the present invention can have one or more blood flow sensors. Such sensors can, within various embodiments be located on the inner (luminal) surfaces of the catheter, the outer (adluminal) surface of the catheter, throughout (i.e., within) the walls of the catheter, and/or concentrated at the various locations (e.g., the ends of the catheter). They can be utilized to measure fluid flow through the catheter. By comparing the readings of sensors throughout the hemodialysis catheter, a determination of blockage (and the extent of a blockage; for example from the formation of a fibrin sheath, catheter stenosis, catheter thrombosis, or catheter kinking) can be determined (e.g., there would be decreased fluid/blood flow prior to a narrowing and increased fluid/blood flow following an narrowing; there would be no fluid/blood flow before or after a complete obstruction). The ability to monitor flow rates would be valuable in normal operation and during/after procedural attempts to "reopen" obstructed catheters. Within other embodiments, pressure sensors can be incorporated into a hemodialysis catheter on the inner (luminal) wall, outer (adluminal) wall, and/or within the body of the catheter itself. Such sensors are able to measure pressure within or exerted against the catheter wall. Increased pressures can be suggestive of stenosis, thrombosis or kinking upstream from a narrowing or obstructing event, whereas decreased pressures would be seen downstream from a narrowing and (little or) no pressure would be seen downstream from an obstruction. Having the ability to measure pressure throughout the catheter allows for functional monitoring of the hemodialysis catheter (in normal operation and during/after attempts to "reopen" obstructed catheters), and the capability of detecting events prior to a complication developing.

Within yet other embodiments, contact sensors can be placed on and throughout the hemodialysis catheter in order to measure contact between the luminal and adluminal surfaces and the surrounding environment. Sustained foreign body contact on either surface could be indicative of the formation of a fibrin sheath, thrombosis, biofilm formation or infection; sustained contact at the tip could indicate that the catheter has become pushed up against the vascular wall and needs to be repositioned.

In yet another embodiment, chemical sensors can be placed primarily on the adluminal (blood contacting) surface and also throughout the central venous catheter in order to measure a wide variety of metabolic parameters, including for example: Blood Oxygen content; Blood $CO_2$ content; Blood pH; Blood cholesterol; Blood lipids (HDL, LDL); Blood Glucose; Cardiac enzymes; Hepatic Enzymes; and Kidney Function (BUN, Creatinine, etc.). Many of these parameters are important in the monitoring the need, effectiveness, timing and frequency of dialysis treatments and would be a great assistance to the clinician managing a renal patient; similarly comparing values in the arterial arm of the catheter, the venous arm of the catheter and the systemic circulation would also provide useful clinical data.

Within other embodiments, position sensors can be placed throughout the hemodialysis catheter (e.g., on both the luminal and adluminal surfaces, and within the catheter material itself) in order to allow imaging of the catheter, and detection of changes and/or movement over time. Position sensors are useful during placement of the catheter to ensure advancement into the proper anatomical location; post-placement, they can be used to determine if the catheter has migrated proximally or distally with time.

Within yet other embodiments chemical and temperature sensors can be utilized to monitor changes in temperature, and/or the presence of an infection, biofilm formation or a developing infection. In summary, a wide variety of sensors may be placed on and/or within the hemodialysis catheters described herein, in order to provide "real time" information and feedback to a health care provider (or during placement or subsequent manipulation or "reopening" procedures), to detect proper placement, anatomy, alignment, forces exerted on surrounding tissues, and to detect the strain encountered during placement and subsequent manipulation or repositioning procedures. For example, the hemodialysis catheters (acute and chronic) provided herein can have one or more contact sensors, strain gauge sensors, pressure sensors, fluid pressure sensors, position sensors, accelerometers, shock sensors, rotation sensors, vibration sensors, tilt sensors, pressure sensors, blood chemistry sensors, blood metabolic sensors, mechanical stress sensors and temperature sensors. Sensors can be placed at a density of greater than 1, 2, 3, 4, 5, 6, 7, 8, 9, 10 or greater than 10 sensors per square centimeter or at a density of greater than 1, 2, 3, 4, 5, 6, 7, 8, 9, 10 or greater than 10 sensors per cubic centimeter. Within either of these embodiments there can be less than 50, 75, 100, or 100 sensors per square centimeter, or per cubic centimeter. The above sensors may be continuously monitored in order to provide a 'real-world' activity, patency, and changes in function over time, to evaluate patient physiology, and to better manage the dialysis patient.

A1.4 Drainage Catheters and their Use

Within other embodiments of the invention, drainage catheters are provided having a variety of sensors placed thereon (see, e.g., FIG. 16B). Briefly, drainage catheters are typically placed in order to drain fluid (e.g., surgical fluids, blood, peritoneal fluids, CSF, biliary fluids, joint fluids, intestinal fluids, pus, an abscess, pleural fluids, or urine to name a few) from a body structure. In the context of urinary drainage, Foley catheters, which are designed to drain urine from the bladder (see, e.g., FIGS. 1A, 16A and 16B), and ureteral catheters (see, e.g. FIG. 1D) which are designed to allow flow of urine from the kidneys), are commonly utilized in a wide variety of medical procedures. Drainage catheters are typically made of polymers such as silicon or rubber, but other materials (including biodegradable polymers) can also be utilized. In the case of a Foley catheter, the catheter typically has two separated lumens, one of which allows urine to drain (typically to a collection bag), and the other has a valve which allows inflation of a balloon at the distal end of the catheter (e.g., a balloon—see FIG. 16A) which is inflated within the bladder after insertion in order to ensure that the catheter doesn't inadvertently fall out.

Common complications of drainage catheters include infections, kinking of the catheter, biofilm build-up (resulting in potential obstruction and infection), breaking of the balloon (as well as overinflating or failing to inflate the balloon) and the accumulation of obstructing foreign bodies (urinary stones, biliary stones, blood/clot, inflammatory tissue, fibrotic tissue, infectious tissue) on the luminal surface.

Hence, drainage catheters of the present invention can be utilized which have one or more of the sensors described herein (see e.g., FIG. 16B). For example, within one embodiment drainage catheters of the present invention can have one or more flow sensors. Such sensors can, within various embodiments be located on the inner (luminal) surfaces, adluminal surfaces of the catheter, throughout the catheter, and/or concentrated at the ends of the catheter. They can be utilized to measure fluid flow through the catheter. By comparing the readings of sensors throughout the drainage catheter, a determination of blockage (and the extent of a blockage; for example from the formation of a clot, stone, or catheter kinking) can be determined (e.g., there would be decreased fluid flow prior to a narrowing and increased fluid flow following an narrowing; there would be no fluid flow before or after a complete obstruction). The ability to monitor flow rates would be valuable in normal operation and during/after procedural attempts to "reopen" obstructed drainage catheters.

Within other embodiments, pressure sensors can be incorporated into a drainage catheter on the inner (luminal) wall, outer (adluminal) wall, and/or within the body of the catheter itself. Such sensors are able to measure pressure within or exerted against the catheter wall. Increased pressures can be suggestive of narrowing, thrombosis, foreign bodies, or kinking upstream from a narrowing or obstructing event, whereas decreased pressures would be seen downstream from a narrowing and (little or) no pressure would be seen downstream from an obstruction. Having the ability to measure pressure throughout the drainage catheter allows for functional monitoring of the catheter (in normal operation and during/after attempts to "reopen" obstructed catheters), and the capability of detecting events prior to a complication developing.

Within yet other embodiments, contact sensors can be placed on and throughout the drainage catheter in order to measure contact between the luminal and adluminal surfaces and the surrounding environment. Sustained foreign body contact on either surface could be indicative of the formation of a fibrin sheath, thrombosis, stone formation, biofilm formation or infection; sustained contact at the tip could indicate that the catheter has become pushed up against the luminal wall and needs to be repositioned.

Within other embodiments, chemical sensors can be utilized to measure a wide variety of physiological parameters, including for example: 1) urinary function (e.g., measurement of nitrate, sodium, potassium, calcium and phosphate); 2) presence of cells (e.g., white cells which may suggest a urinary tract infection, and/or red cells which may indicate trauma, stones, infections, and/or a malignancy); 3) protein/proteinuria (indicative of diabetes, kidney or liver disease, hyperthyroidism, etc.); 4) glucose (to measure diabetes); and various other chemicals (e.g., ketones, bilirubin, urobilinogen, hemoglobin, creatinine, catecholamines, dopamine, cortisol, phenylalanine) and characteristics of the urine (e.g., specific gravity, osmolality, pH, presence of bacteria, and hcG).

Taken collectively, a wide variety of sensors as described herein can be utilized to detect, measure and assess a number of factors relevant to the function of the kidneys (and/or bladder).

Within other embodiments, position sensors can be placed throughout the drainage catheter (e.g., on both the luminal and adluminal surfaces, and within the catheter material itself) in order to allow imaging of the catheter, and detection of changes and/or movement over time. Position sensors are useful during placement of the catheter to ensure advancement into the proper anatomical location (prior to balloon inflation, if present, such as in Foley catheters); post-placement, they can be used to determine if the catheter has migrated proximally or distally with time.

Within yet other embodiments chemical and temperature sensors can be utilized to monitor changes in temperature, and/or the presence of an infection, biofilm formation, or a developing infection.

In summary, a wide variety of sensors may be placed on and/or within the drainage catheters described herein, in order to provide "real time" information and feedback to a health care provider (or during placement or subsequent manipulation or "reopening" procedures), to detect proper placement, anatomy, alignment, forces exerted on surrounding tissues, and to detect the strain encountered during placement and subsequent manipulation or repositioning procedures. For example, the drainage catheters provided herein can have one or more contact sensors, strain gauge sensors, pressure sensors, fluid pressure sensors, position sensors, accelerometers, shock sensors, rotation sensors, vibration sensors, tilt sensors, pressure sensors, chemistry sensors, metabolic sensors, mechanical stress sensors and temperature sensors. Sensors can be placed at a density of greater than 1, 2, 3, 4, 5, 6, 7, 8, 9, 10 or greater than 10 sensors per square centimeter or at a density of greater than 1, 2, 3, 4, 5, 6, 7, 8, 9, 10 or greater than 10 sensors per cubic centimeter. Within either of these embodiments there can be less than 50, 75, 100, or 100 sensors per square centimeter, or per cubic centimeter. The above sensors may be continuously monitored in order to provide a 'real-world' activity, patency, and changes in function over time, to evaluate patient physiology, and to better manage the drainage catheter patient.

A2. Vascular Grafts and their Use

Within other embodiments of the invention, sensors can be placed on a variety of grafts. Briefly, medical grafts are hollow tubes or cylinders that are utilized to allow fluids to flow from one place to another. Medical grafts may be obtained from natural materials (e.g., saphenous vein or mammary artery grafts), constructed from natural and/or artificial materials (e.g., bioengineered grafts or blood vessels), or constructed from entirely synthetic materials (e.g., vascular grafts comprised of polymers such as polytetrafluoroethylene or "PTFE" or dacron). Representative examples of medical grafts are disclosed in U.S. Pat. Nos. 5,556,426, 5,628,786, 5,641,373, 6,863,686, and 8,062,354.

Figure 5:
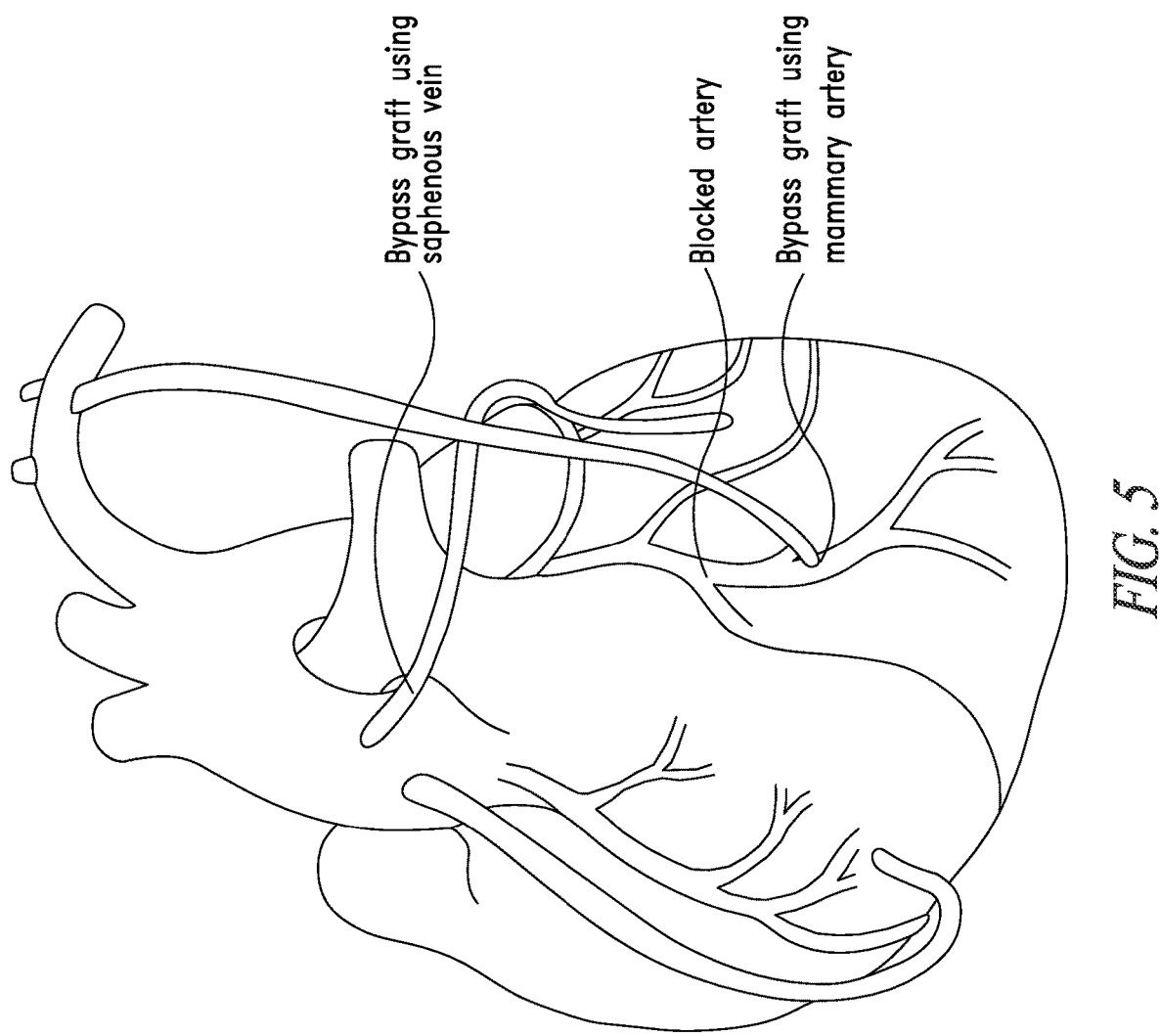
FIG. 5 illustrates one embodiment wherein sensors can be placed on bypass grafts, including for example venous bypass (e.g., utilizing a saphenous vein), and arterial bypass (e.g., using a mammary artery).

Within one embodiment of the invention, a variety of sensors are placed on a graft made from natural materials. For example, during Coronary Artery Bypass Grafting (or "CABG" procedures), arteries or veins from elsewhere in the body can be grafted onto the coronary arteries to bypass atherosclerotic narrowings and improve blood supply to the myocardium (see for example FIG. 5, wherein saphenous veins are utilized for coronary artery bypass, and a mammary artery is used for a coronary artery bypass). Such procedures can be performed "on-pump" (i.e., with a heart-lung bypass machine), or "off-pump" (with a beating heart). Typically, the surgeon will bypass the obstruction by sewing one end of the graft beyond the blockage, and other to the aorta. Various complications however can arise in such procedures, including for example, occlusion and failure of the graft, infection, arrhythmia, hypotension, hypoxia, myocardial infarction, and renal failure.

Figure 6B:
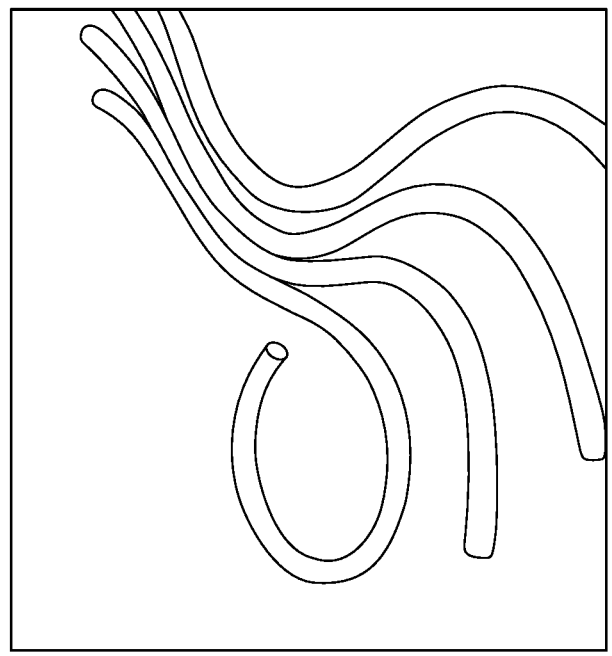
FIG. 6 illustrates one embodiment wherein vascular bypass (FIG. 6A) is accomplished utilizing a synthetic graft (FIG. 6B).
Figure 6A:
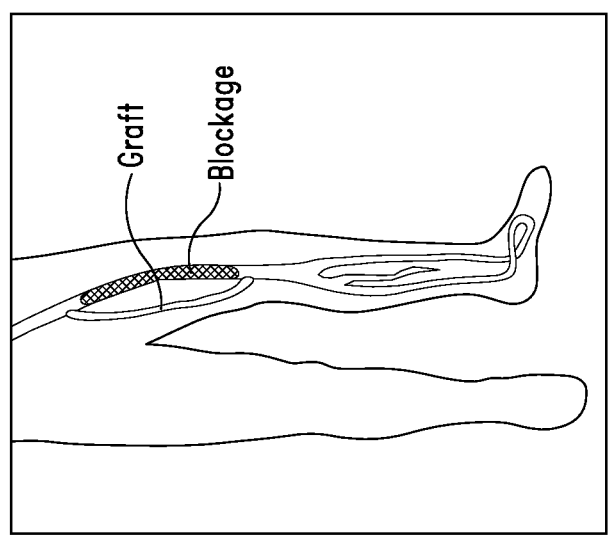

Within other embodiments of the invention synthetic grafts can be utilized to bypass an obstruction, for example, as shown in FIG. 6 synthetic vascular bypass grafts (see, e.g., FIG. 6B) are utilized to bypass an obstruction in the lower limb (FIG. 6A).

Figure 7:
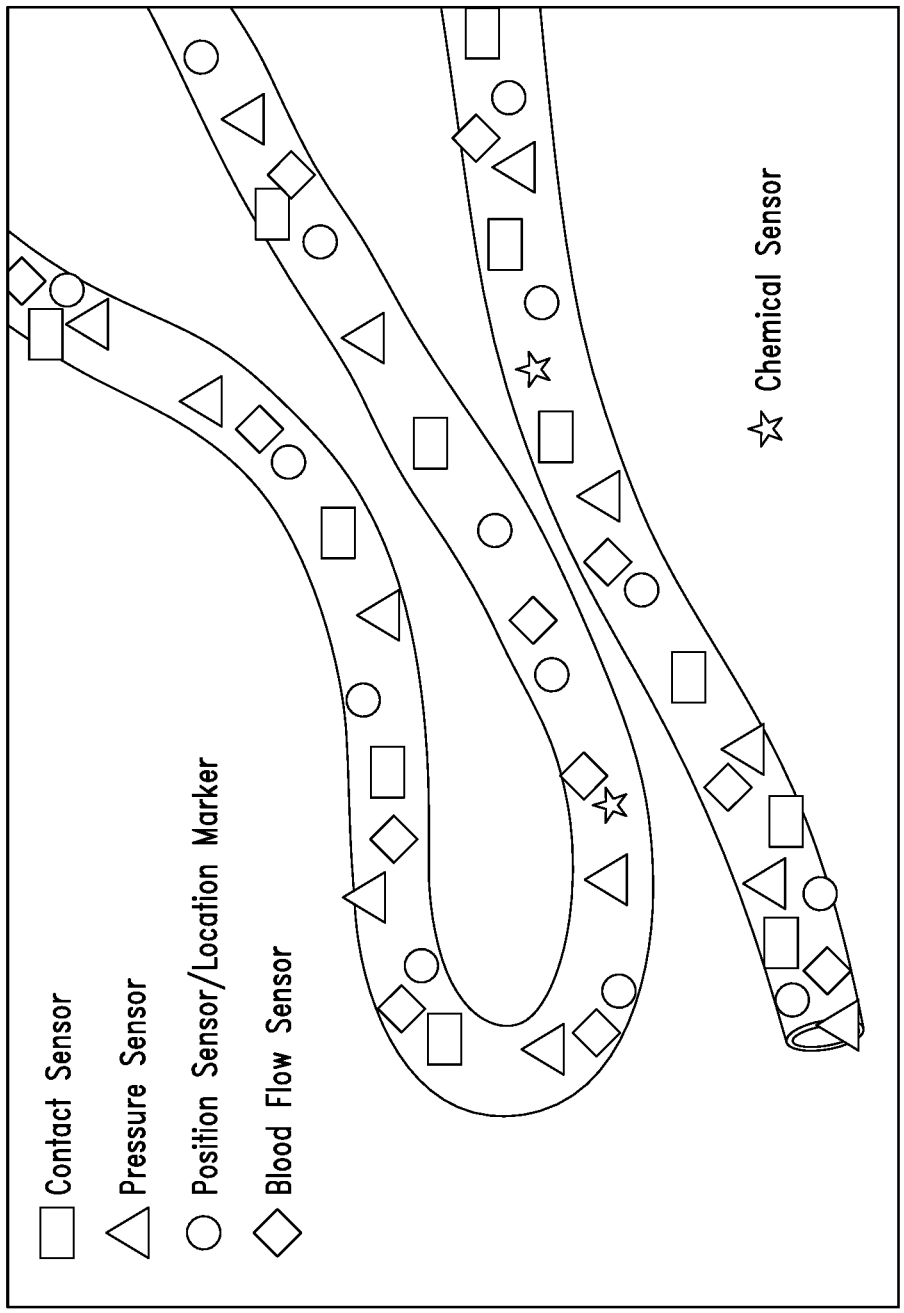
FIG. 7 illustrates one embodiment of a vascular bypass graft with a variety of sensors.
Figure 8:
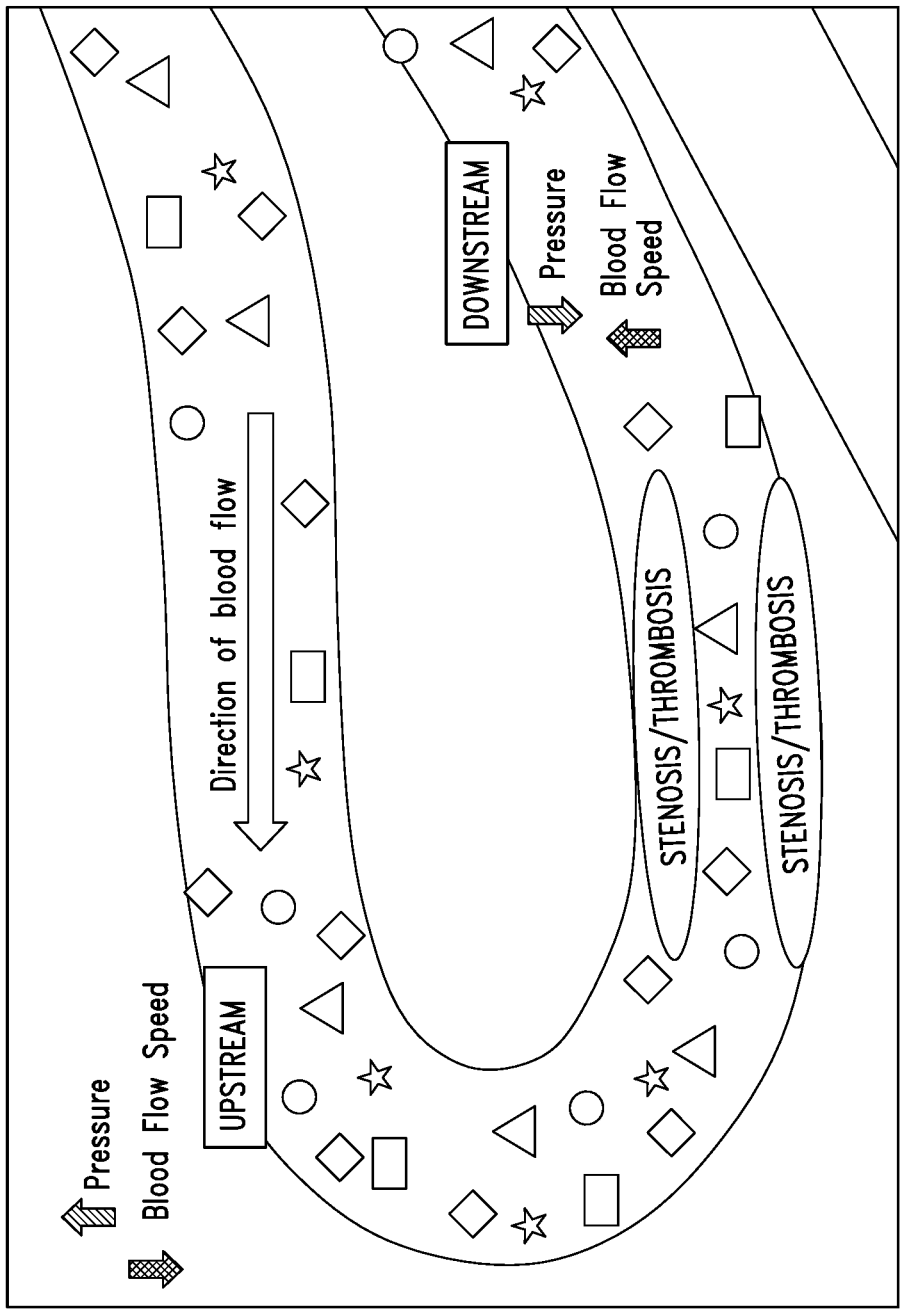
FIG. 8 illustrates one embodiment wherein a vascular graft with sensors can be utilized to detect stenosis or thrombosis by changes in pressure and blood flow speed prior to, and subsequent to the obstruction.

Hence, grafts of the present invention can be utilized which have one or more of the sensors described herein (see e.g., FIG. 7). For example, within one embodiment, grafts of the present invention can have one or more blood flow sensors. Such sensors can, within various embodiments be located on the inner (luminal) surfaces of the graft, on the outer (adluminal) surfaces of the graft, throughout the graft, and/or concentrated at the ends of the graft (i.e. the vascular anastomoses). They can be utilized to measure blood flow through the graft. As shown in FIG. 8, by comparing the readings of sensors throughout the graft, a determination of partial narrowing (and the extent of narrowing) can be determined (e.g., there would be an decreased blood flow prior to a narrowing or stenosis, and increased blood flow following a narrowing). If the vascular graft was completely obstructed, there would be no flow through the graft (before or after the obstruction). The ability to monitor flow rates would be valuable in normal operation and during/after procedural attempts to "reopen" obstructed catheters.

Within other embodiments, pressure sensors can be incorporated into a graft [e.g., on the outer (adluminal) walls, the inner (luminal) walls and/or within the body of the graft itself]. Such sensors are able to measure pressure in or against the vessel wall. As shown in FIG. 8, increased pressures can be suggestive of stenosis, thrombosis or kinking upstream from an obstructing event, whereas decreased pressures would be seen downstream from a narrowing and (little or) no pressure would be seen downstream from an obstruction. Having the ability to measure pressure throughout the vascular allows for functional monitoring of the graft (in normal operation and during/after attempts to "reopen" obstructed grafts), and the capability of detecting events prior to a complication developing.

Within yet other embodiments contact sensors can be placed on and throughout the graft in order to measure contact (integrity of the seal) between the bypass graft and the vessel to which it is attached (the anastomosis) in order to identify leaks or anastomotic failure (during and after surgical placement). Contact sensors on the luminal surface of the graft could detect the presence of restenosis tissue or biofilm and alert the clinician to potential problems.

Figure 9:
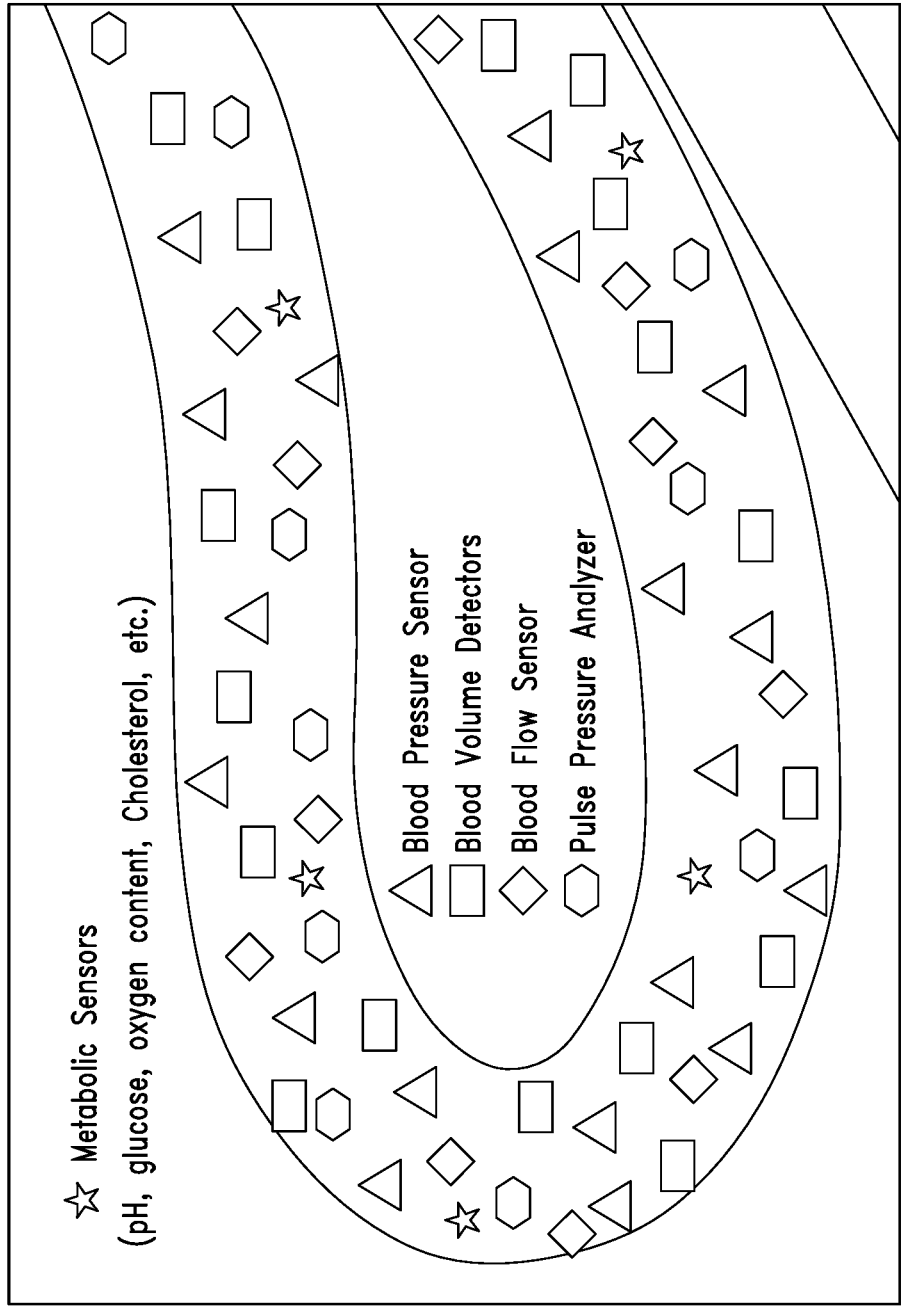
FIG. 9 illustrates one embodiment wherein a vascular graft has a variety of sensors which can be utilized to detect and monitor cardiac output and circulatory performance.

Within further embodiments chemical sensors (see e.g., FIG. 9) can also be placed on and throughout the graft in order to measure a wide variety of important metabolic parameters, including for example: Blood Oxygen content; Blood $CO_2$ content; Blood pH; Blood cholesterol; Blood lipids (HDL, LDL); Blood Glucose; Cardiac enzymes; Hepatic Enzymes; and Kidney Function (BUN, Creatinine, etc.).

Figure 10:
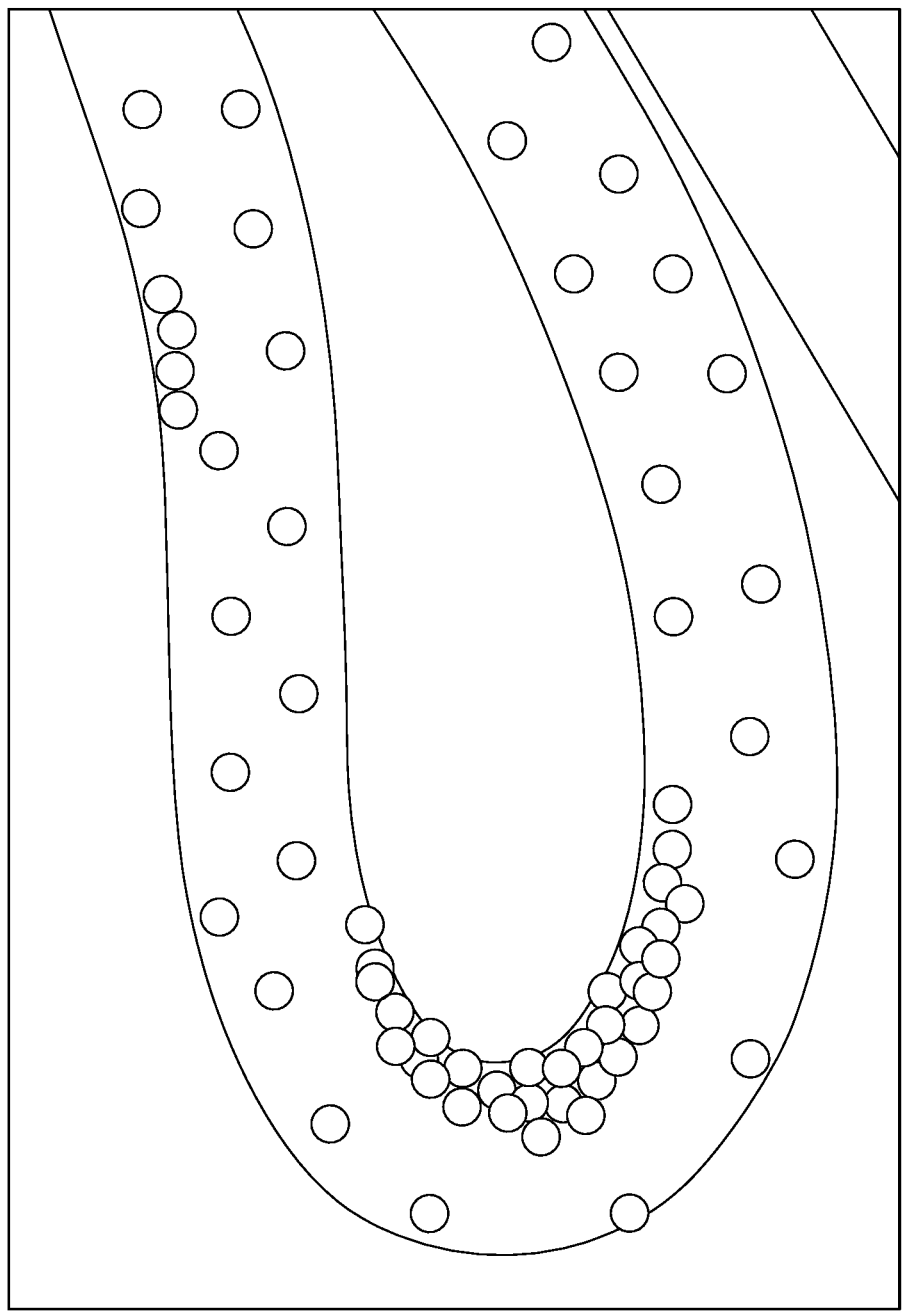
FIG. 10 illustrates one embodiment wherein sensors in a vascular graft can be utilized to image the graft, as well as, for example, vascular anatomy, stenosis, and kinking of the graft.

Within other embodiments position sensors can be placed throughout the graft (e.g., on both the luminal and adluminal surfaces, and within the graft material itself) in order to allow imaging of the graft, and detection of changes (such as bending or kinking) and/or movement over time (see, e.g., FIG. 10).

Taken collectively, a wide variety of sensors as described herein can be utilized to detect, measure and assess a number of factors relevant to cardiac function. For example, blood flow rate detectors, blood pressure detectors, and blood volume detectors (e.g., to measure blood volume over a unit of time) can be placed within (on the luminal side), and on other parts of the graft in order to measure systolic and diastolic pressure, cardiac output, ejection fraction, cardiac index and systemic vascular resistance.

Figure 11:
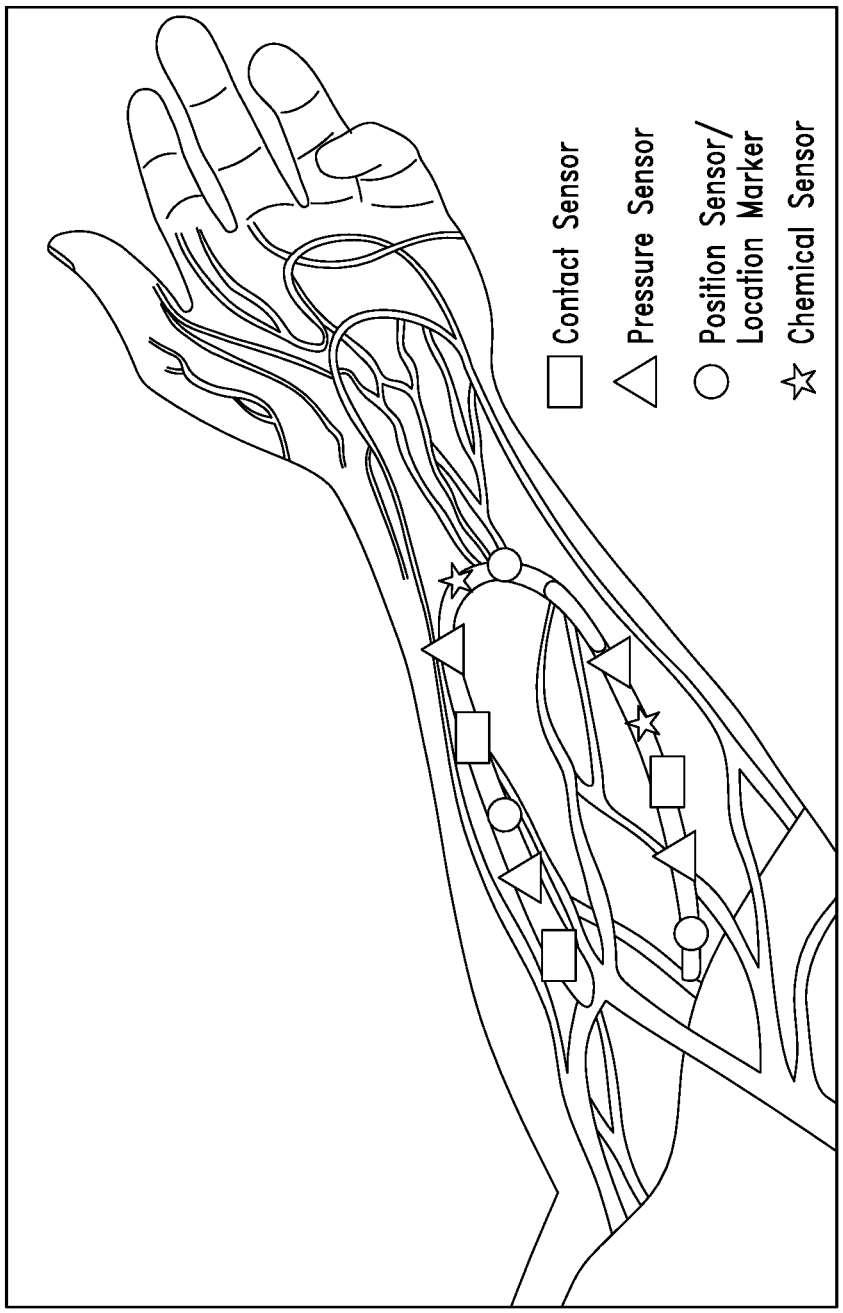
FIG. 11 illustrates one embodiment wherein sensors are placed in/on a vascular access (hemodialysis) graft.
Figure 12:
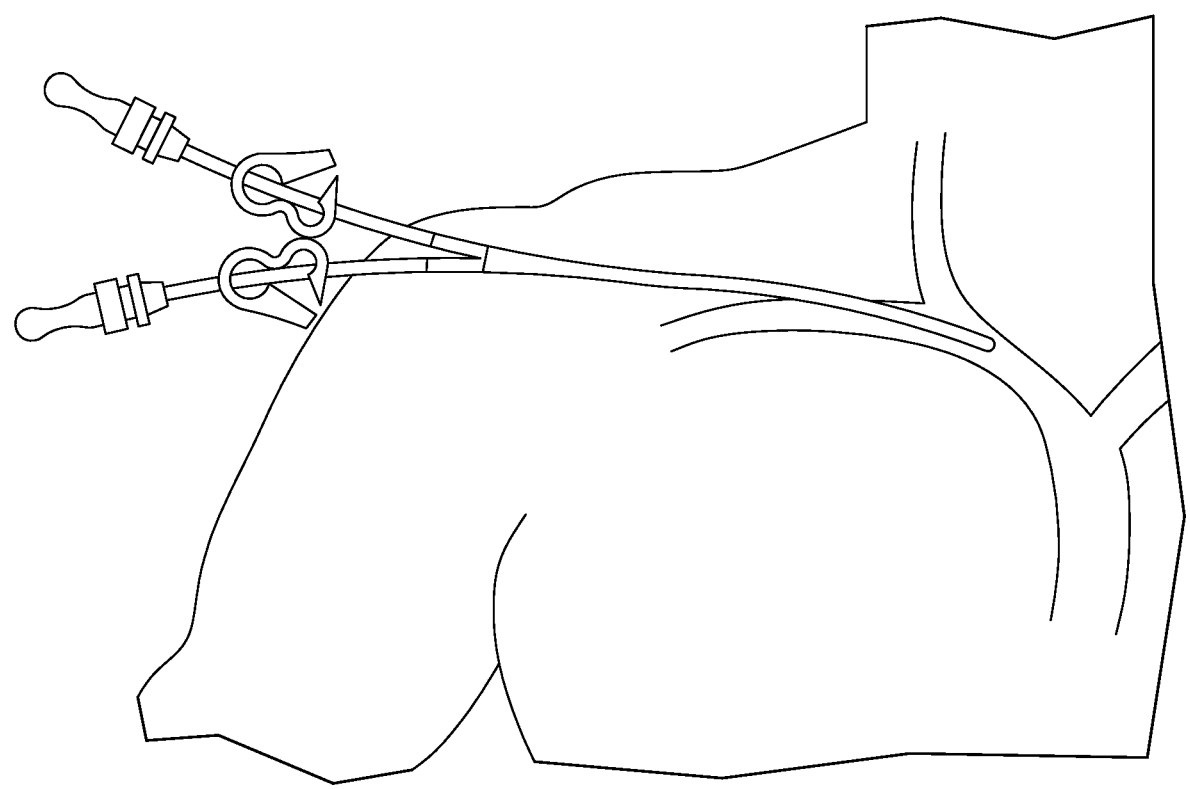
FIG. 12 illustrates one embodiment wherein sensors are placed in/on a vascular access (hemodialysis) graft.

Within particularly preferred embodiments such sensors can also be utilized to detect cardiac output (which is a key clinical measurement to be monitored in cardiac compromised patients). For example, high-fidelity pressure transducers can be located on, in, or within a graft in order to measure the timing and pressure of pulsations. Such measurements can be utilized to assess stroke volume and systemic vascular resistance, and also provide continuous cardiac output monitoring and heart rate monitoring. Within other embodiments of the invention, vascular grafts (synthetic grafts and native grafts such as arterio-venous fistulas) can be utilized in a hemodialysis procedure (see, e.g., FIG. 11 and FIG. 12). Briefly, a hemodialysis access graft is a vascular graft that is implanted by a vascular surgeon as an artificial, high-flow, interposition graft (or direct anastomosis) between an artery and a vein (typically in the forearm or the thigh) to provide permanent access for hemodialysis (native arteries and veins tend to collapse and close after being repeatedly instrumented numerous times). Once mature and suitable for use, the hemodialysis access graft (or AV fistula) is used as a permanent site into which to insert another catheter that is used for exchanging blood to and from a hemodialysis machine. Typically, that catheter has two lumens, one for venous flow and the other for arterial flow (as described in a previous section above). The arterial lumen of the catheter withdraws blood from the hemodialysis access graft of the patient and carries it to the hemodialysis machine (where it is "cleaned" and processed), and the venous lumen of the catheter then returns the treated blood to hemodialysis access graft of the patient to be returned to the circulation. Common complications of hemodialysis access grafts include clotting, stenosis (narrowing of the graft most often occurring at graft-venous anastomosis, but also occasionally at the arterial-graft anastomosis), infection and kinking. Hence, hemodialysis access grafts of the present invention can be utilized which have one or more of the sensors described herein (see e.g., FIGS. 11 and 12). For example, within one embodiment hemodialysis access grafts of the present invention can have one or more blood flow sensors. Such sensors can, within various embodiments be located on the inner (luminal) surfaces of the access graft, throughout (i.e., within) the walls of the access graft, and/or concentrated at the various locations (e.g., the ends—the anastomoses—of the access graft). They can be utilized to measure blood flow through the access graft. By comparing the readings of sensors throughout the hemodialysis access graft, a determination of partial narrowing (and the extent of narrowing) can be determined (e.g., there would be an decreased blood flow prior to a narrowing or stenosis, and increased blood flow following a narrowing). If the access graft was completely obstructed, there would be no flow through the graft (before or after the obstruction). The ability to monitor flow rates would be valuable in normal operation and during/after procedural attempts to "reopen" obstructed catheters. Within other embodiments, pressure sensors can be incorporated into a dialysis access graft [e.g., on the outer (adluminal) walls, on the inner (luminal) walls, or within the body of the access graft itself]. Such sensors are able to measure pressure in or against the access graft wall. Increased pressures can be suggestive of stenosis (typically at the graft-vein anastomsis, but occasionally at the artery-graft anastomosis), thrombosis or kinking upstream from an obstructing event, whereas decreased pressures would be seen downstream from a narrowing and (little or) no pressure would be seen downstream from an obstruction. Having the ability to measure pressure throughout the vascular allows for functional monitoring of the graft (in normal operation and during/after attempts to "reopen" obstructed grafts), as well as the capability of detecting events prior to a clinical complication developing. Within yet other embodiments contact sensors can be placed on and throughout the hemodialysis access graft in order to measure contact (integrity of the seal) between the access graft and the vessel to which it is attached (i.e. the vascular anastomosis) in order to identify leaks or anastomotic failure (during and after surgical placement). Contact sensors on the luminal surface of the graft could detect the presence of restenosis tissue or biofilm and alert the clinician to potential problems.

In yet another example, chemical sensors can also be placed on and throughout the access graft in order to measure a wide variety of metabolic parameters, including for example: Blood Oxygen content; Blood $CO_2$ content; Blood pH; Blood cholesterol; Blood lipids (HDL, LDL); Blood Glucose; Cardiac enzymes; Hepatic Enzymes; and Kidney Function (BUN, Creatinine, etc.); parameters which are very important in the clinical management of a patient with late-stage renal disease. Within other embodiments position sensors can be placed throughout the hemodialysis access graft (e.g., on both the luminal and adluminal surfaces, and within the access graft material itself) in order to allow imaging of the access graft, and detection of changes (bending, kinking) and/or movement over time. Taken collectively, a wide variety of sensors as described herein can also be utilized to detect, measure and assess a number of factors relevant to cardiac function. For example, blood flow rate detectors, blood pressure detectors, and blood volume detectors (e.g., to measure blood volume over a unit of time) can be placed within (on the luminal side), and on other parts of the access graft in order to measure systolic and diastolic pressure, and estimate systemic vascular resistance. Within particularly preferred embodiments blood flow rate detectors, blood pressure detectors, and blood volume detectors can also be utilized to calculate cardiac output, ejection fraction and cardiac index (which are key clinical measurements that are valuable in monitoring cardiac-compromised patients, which many renal patients are). For example, high-fidelity pressure transducers can be located on, in, or within a hemodialysis access graft in order to measure the timing and pressure of pulsations. Such measurements can be utilized to assess stroke volume and systemic vascular resistance, and also provide continuous cardiac output monitoring and heart rate monitoring. Within yet other embodiments chemical and temperature sensors can be utilized to monitor changes in temperature, and/or the presence of an infection or a developing infection. With repeated instrumentation of the access graft, the incidence of infection is quite high and monitoring for its presence prior to the onset of clinical symptoms is of great value to the management of the patient. In summary, a wide variety of sensors may be placed on and/or within hemodialysis access grafts described herein, in order to provide "real time" information and feedback to a health care provider (or a surgeon during a surgical procedure to implant a hemodialysis access graft, or an interventionalist performing a procedure to open up an obstructed hemodialysis access graft), to detect proper placement, anatomy, alignment, forces exerted on surrounding tissues, and to detect the strain encountered in an surgical procedure. For example, the hemodialysis access grafts provided herein can have one or more contact sensors, strain gauge sensors, pressure sensors, fluid pressure sensors, position sensors, accelerometers, shock sensors, rotation sensors, vibration sensors, tilt sensors, pressure sensors, tissue chemistry sensors, tissue metabolic sensors, mechanical stress sensors and temperature sensors. Sensors can be placed at a density of greater than 1, 2, 3, 4, 5, 6, 7, 8, 9, 10 or greater than 10 sensors per square centimeter or at a density of greater than 1, 2, 3, 4, 5, 6, 7, 8, 9, 10 or greater than 10 sensors per cubic centimeter. Within either of these embodiments there can be less than 50, 75, 100, or 100 sensors per square centimeter, or per cubic centimeter.

The above sensors may be continuously monitored in order to provide a 'real-world' activity, healing, and changes in function over time, to evaluate patient activity, and to better understand the conditions which hemodialysis access grafts are exposed to in the real world.

A3. Other Medical Tubes and their Use

Within other embodiments a wide variety of tubes are provided which may have one or more sensors. Representative examples of medical tubes include tympanostomy tubes, endotracheal tubes, tracheostomy tubes, nasogastric tubes, gastric tubes, feeding tubes, colostomy tubes, rectal tubes, and chest tubes.

Figure 14A:
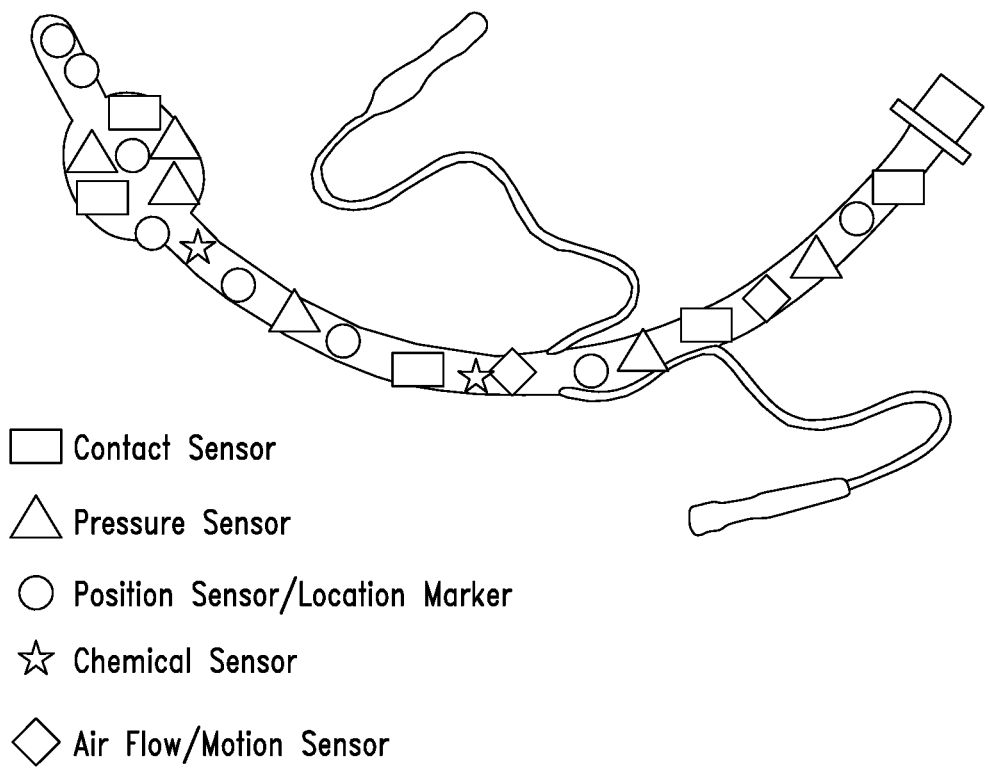
FIG. 14A illustrates one embodiment wherein a variety of sensors are placed onto (or within) an endotracheal tube.

For example within one embodiment one or sensors can be placed on an endotracheal tube (see FIG. 14A). Briefly, an endotracheal tube is a type of catheter that is inserted into the trachea for the primary purpose of establishing and maintaining a patent airway. The tube may be orotracheal (inserted into the mouth—see e.g., FIG. 14B), nasotracheal (inserted into the nose), or via a tracheostomy (e.g., inserted via a hole or incision in the trachea).

Figure 15A:
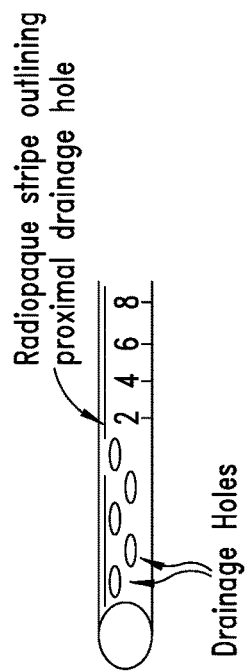
FIG. 15A illustrates a chest tube, along with the placement of a chest tube in a subject.
Figure 15A:
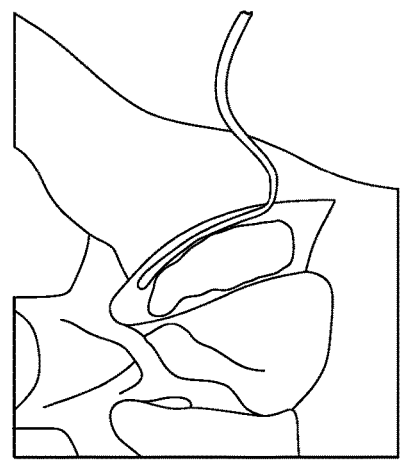
Figure 15B:
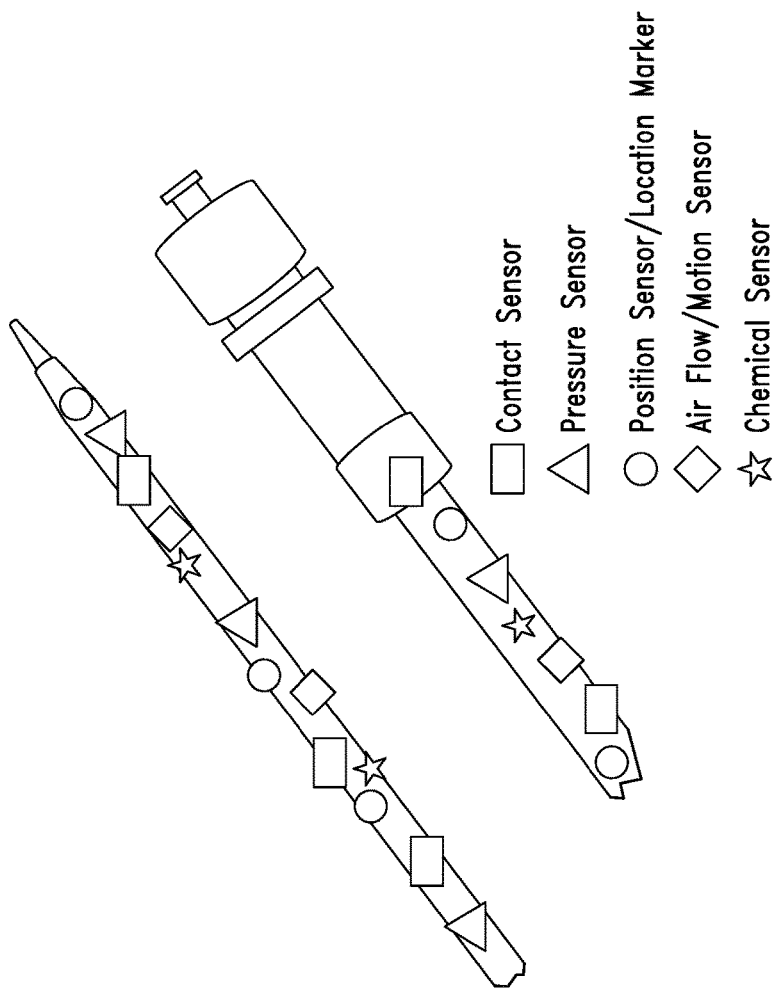
FIG. 15B illustrates one embodiment wherein a variety of sensors are placed on (or within) a chest tube.

Within other embodiments the tube having one or more sensors can be a drainage tube such as a chest tube (see, e.g., FIG. 15B). Briefly, chest tubes (also referred to as 'chest drains', thoracic catheters, tube thoracostomy and intercostal drains) are flexible tubes that can be inserted through the chest wall and into the pleural space or mediastinum (see, e.g. FIG. 15A). Such tubes can be utilized to remove air (e.g., pneumothorax), fluid (e.g., pleural effusion, blood, chyle), and infectious material (e.g., empyema, pus)

Chest tubes come in a range of sizes (e.g., 6 Fr to 40 Fr), can have multiple drainage fenestrations, and optionally, be marked for distance (or length) of the tube, as well as contain radiopaque markers (see, e.g. FIG. 15A). They are available in a wide variety of configurations (e.g., right angle, trocar, flared, and tapered), and may be coated in an effort to prevent thrombus formation or clogging. Such tubes can be made from a wide variety of materials, including polyvinyl chloride ("PVC"), silicone, latex, and polyurethane.

Tubes (e.g., tympanostomy tubes, endotracheal tubes, tracheostomy tubes, nasogastric tubes, gastric tubes, feeding tubes, colostomy tubes, rectal tubes, and chest tubes) can suffer from a variety of complications, such as improper placement, damage to (or penetration into) surrounding tissues, narrowing, obstruction, movement/migration and infection, For example, endotracheal tubes have been found to cause a number problems, including aspiration, improper placement, airway obstruction, perforation of the esophagus or trachea, development of a sore throat, pneumonia, narrowing, as well as arrhythmia, hypertension, increased intracranial pressure, increased intraocular pressure, bronchospasms, laryngospasms, vocal cord damage, retropharyngeal abcesses, nerve injury, and fistulas.

Figure 14B:
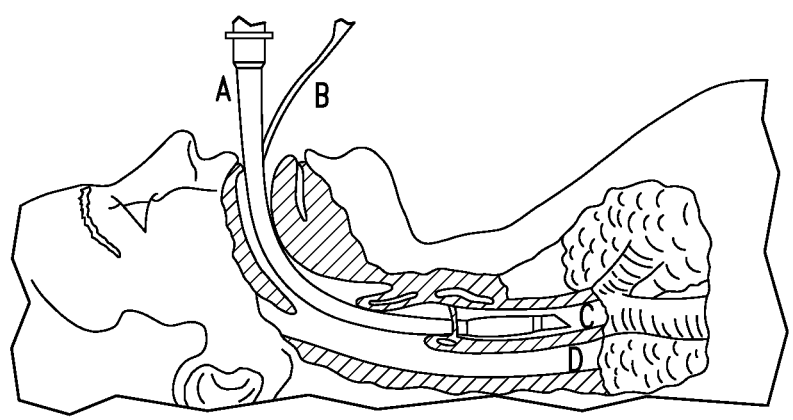
FIG. 14B illustrates the placement of an endotracheal tube in a subject.

Hence, tubes of the present invention can be utilized which have one or more of the sensors described herein (see e.g., FIGS. 14B and 15B). For example, within one embodiment chest tubes (see, e.g. FIG. 15B) and endotracheal tubes (see, e.g. FIG. 14B) of the present invention can have one or more flow sensors. Such sensors can, within various embodiments be located on the inner (luminal) surfaces of the tube, the outer (adluminal) surface of the tube, throughout the tube, and/or concentrated at the ends of the tube. They can be utilized to measure fluid flow through the tube, such as air flow (endotracheal tubes, chest tubes in pneumothorax); other tubes as described above may have other body fluids passing through them. By comparing the readings of sensors throughout the tube, a determination of partial narrowing (and the extent of narrowing) can be determined (e.g., there would be decreased air flow prior to a narrowing or stenosis, and increased air flow following a narrowing). If the tube was completely obstructed, there would be no flow through the tube lumen (before or after the obstruction). The ability to monitor flow rates would be valuable in normal operation and during/after procedural attempts to "reopen" obstructed tubes.

Within other embodiments, pressure sensors can be incorporated into a tube [e.g., on the outer (adluminal) walls, the inner (luminal) walls and/or within the body of the tube itself]. Such sensors are able to measure pressure in or against the tube wall. Increased pressures (e.g. ventilation pressures in endotracheal tubes) can be suggestive of stenosis (narrowing), obstruction or kinking upstream from an obstructing event, whereas decreased pressures would be seen downstream from a narrowing and (little or) no pressure would be seen downstream from an obstruction. Monitoring pressure in the inflation cuff of an endotracheal tube can ensure that proper inflation is present; not too much pressure so as to lead to mucosal damage to the surrounding trachea, but not too little so as to allow fluids to pass by the cuff and aspiration to occur. Having the ability to measure pressure throughout the tube allows for functional monitoring of the tube (in normal operation and during/after attempts to "reopen" obstructed tubes), as well as the capability of detecting events prior to a clinical complication developing.

Within yet other embodiments contact sensors can be placed on and throughout the tube in order to measure contact (integrity of the seal) between the tube and the tissue in which it is placed in order to identify leaks, cracks, or migration of the tube (during and after surgical placement). Contact sensors on the luminal surface of the tube could detect the presence of fibrous/inflammatory tissue or biofilm formation and alert the clinician to potential problems. Monitoring contact on the surface of the inflation cuff of an endotracheal tube can ensure that proper inflation is present; creating a sufficient seal between the cuff and the tracheal mucosa such that fluids are unable to pass by the cuff and allow aspiration to occur.

Within other embodiments, chemical sensors can be utilized to measure a wide variety of physiological parameters, including for example: 1) tissue chemistry (e.g., measurement of nitrate, sodium, potassium, calcium and phosphate); 2) the presence of cells (e.g., white cells which may suggest an infection, and/or red cells which may indicate trauma, erosions/ulcers, penetration of the device into a blood vessel); 3) protein, serous fluid); 4) glucose ketones, bilirubin, urobilinogen, hemoglobin, osmolality, pH, presence of bacteria, tumor markers.

Within other embodiments position sensors can be placed throughout the tube (e.g., on both the luminal and adluminal surfaces, and within the tube material itself) in order to allow imaging of the tube, and detection of changes and/or movement over time. For example, improper placement of endotracheal tubes (usually placement in the esophagus) is a very dangerous complication; 50% of misplacements in the Emergency Room result in death. Position sensors able to better define the anatomical position and placement of the endotracheal tube (in "real time") would be of great utility. Many other tubes (e.g. proper chest tube placement in the area of pleura requiring decompression/drainage and not in adjacent tissues—lung, heart, pericardium) would similarly benefit. Post-insertion, many tubes can move from their initial site of placement (e.g. tympanostomy tubes often fall out, endotracheal tubes can migrate into one of the bronchi to produce uneven ventilation, chest tubes can move from the required drainage area) and would benefit from the ability to monitor their movement and current location.

Taken collectively, a wide variety of sensors as described herein can be utilized to detect, measure and assess a number of factors relevant to the function numerous implanted tubes.

Within yet other embodiments chemical and temperature sensors can be utilized to monitor changes in temperature, and/or the presence of an infection or a developing infection.

A4. Manufacturing of Medical Tubes

Within various embodiments of the invention, methods are also provided for manufacturing a tube having one of the sensors provided herein. For example, within one embodiment of the invention a tube which is utilized to: 1) bypass an obstruction (e.g., in the case of Coronary Artery Bypass Grafts, or "CABG" and peripheral bypass grafts) or open up an obstruction (balloon dilation catheters, angioplasty balloons); 2) to relieve pressure (e.g., shunts, drainage tubes and drainage catheters, urinary catheters); 3) to restore or support anatomical structures (e.g., endotracheal tubes, tracheostomy tubes, and feeding tubes); and 4) for access (e.g., CVC catheters, peritoneal and hemodialysis catheters). Representative examples of tubes include catheters (as discussed in more detail below), auditory or Eustachian tubes, drainage tubes, tracheotomy tubes (e.g., Durham's tube), endobronchial tubes, endotracheal tubes, esophageal tubes, feeding tubes (e.g., nasogastric or NG tubes), stomach tubes, rectal tubes, colostomy tubes, and a wide variety of grafts (e.g., bypass grafts) is constructed such that one or more sensors provided herein are placed directly into, onto or within the tube at the time of manufacture, and subsequently sterilized in a manner suitable for use in subjects.

For example, within one embodiment of the invention a tube (e.g., mechanical or biological) is constructed such that one or more sensors provided herein are placed directly on, within, or into the tube at the time of manufacture, and subsequently sterilized in a manner suitable for use in subjects.

In one embodiment, a biological tube may be prepared (see e.g., WO 2012/134024, which is incorporated by reference in its entirety). Sensors provided herein may be directly implanted into the tissue of an artificial tube, and subsequently implanted into a patient.

Within further embodiments, scaffolds can be prepared for a tube (see, e.g., U.S. Pat. No. 8,562,671, and WO 2013/142879 which are incorporated by reference in their entirety). Briefly, scaffolds composed of one or more compounds (e.g., polymers) can be prepared in order to mimic the shape of a tube (or portion thereof). Sensors can be placed into the structure before, during, or subsequent to manufacture of the valve (e.g., in the case or electrospinning or molding of polymer fibers, or in the case of 3D printing as described in more detail below). Within certain preferred embodiments the scaffold can be seed with stem cells suitable for growth of tissue on the artificial tube (see, e.g., WO 1999/003973 and U.S. Pat. No. 8,852,571, which are incorporated by reference in their entirety).

Within further embodiments, the present disclosure provides a method of making a tube by 3D printing, additive manufacturing, or a similar process whereby the tube is formed from powder or filament that is converted to a fluid form that subsequently solidifies as the desired shape. For convenience, such processes will be referred to herein as printing processes or 3D printing processes. The present disclosure provide a method of making a tube by a printing process, where that tube includes a sensor, circuit or other feature as disclosed herein (collectively sensor or sensors). The sensor may be separately produced and then incorporated into the tube during the printing process. For example, a sensor may be placed into a desired position and the printing process is carried out around the sensor so that the sensor becomes embedded in the printed tube. Alternatively, the printing process may be started and then at appropriate times, the process is paused to allow a sensor to be placed adjacent to the partially completed tube. The printing process is then re-started and construction of the tube is completed. The software that directs the printing process may be programmed to pause at appropriate predetermined times to allow a sensor to be added to the partially printed tube.

In addition, or alternatively, the sensor itself, or a portion thereof may be printed by the 3D printing process. Likewise, electronic connectively to, or from, or between, sensors may be printed by the 3D printing process. For example, conductive silver inks may be deposited during the printing process to thereby allow conductivity to, or from, or between sensors of a tube. See, e.g., PCT publication nos. WO 2014/085170; WO 2013/096664; WO 2011/126706; and WO 2010/0040034 and US publication nos. US 2011/0059234; and US 2010/0037731. Thus, in various embodiments, the present disclosure provides tubes wherein the sensor is printed onto a substrate, or a substrate is printed and a sensor is embedded or otherwise incorporated into or onto the substrate, or both the substrate and the sensor are printed by a 3D printing technique.

3D printing may be performed using various printing materials, typically delivered to the 3D printer in the form of a filament. Two common printing materials are polylactic acid (PLA) and acrylonitrile-butadiene-styrene (ABS), each being an example of a thermoplastic polymer. When strength and/or temperature resistance is particularly desirable, then polycarbonate (PC) may be used as the printing material. Other polymers may also be used. See, e.g., PCT publication nos. WO 2014/081594 for a disclosure of polyamide printing material. When metal parts are desired, a filament may be prepared from metal or metal alloy, along with a carrier material which ultimately will be washed or burned or otherwise removed from the part after the metal or metal alloy has been delivered.

When the tube is of a particularly intricate shape, it may be printed with two materials. The first material is cured (using, e.g., actinic radiation) as it is deposited, while the second material is uncured and can be washed away after the tubes has been finally printed. In this way, significant hollow spaces may be incorporated into the tube.

Additive manufacturing is a term sometimes used to encompass printing techniques wherein metal or metal allow is the material from which the desired part is made. Such additive manufacturing processes utilizes lasers and build an object by adding ultrathin layers of materials one by one. For example, a computer-controlled laser may be used to direct pinpoint beams of energy onto a bed of cobalt-chromium alloy powder, thereby melting the alloy in the desired area and creating a 10-30-micron thick layer. Adjacent layers are sequentially and repetitively produced to create the desired sized item. As needed, a sensor may be embedded into the alloy powder bed, and the laser melts the powder around the sensor so as to incorporate the sensor into the final product. Other alloys, including titanium, aluminum, and nickel-chromium alloys, may also be used in the additive manufacturing process. See, e.g., PCT publication nos. WO 2014/083277; WO 2014/074947; WO 2014/071968; and WO 2014/071135; as well as US publication nos. US 2014/077421; and US 2014/053956.

Accordingly, in one embodiment the present disclosure provides a method of fabricating sensor-containing tubes, the method comprising forming at least one of a sensor and a support for the sensor using a 3D printing technique. Optionally, the 3D printing technique may be an additive manufacturing technique. In a related embodiment, the present disclosure provides a tube that is produced by a process comprising a 3D printing process, such as an additive manufacturing process, where the tubes includes a sensor.

Within yet further embodiments of the invention, the tubes provided herein can be sterilized suitable for use in a subject.

Disclosure of 3D printing processes and/or additive manufacturing is found in, for example PCT publication nos. WO 2014/020085; WO 2014/018100; WO 2013/179017; WO 2013/163585; WO 2013/155500; WO 2013/152805; WO 2013/152751; WO 2013/140147 and US publication nos. 2014/048970; 2014/034626; US 2013/337256; 2013/329258; US 2013/270750.

In summary, a wide variety of sensors may be placed on and/or within the tubes described herein, in order to provide "real time" information and feedback to a health care provider (or a physician during an insertion or follow-up procedure), to detect proper placement, anatomy, alignment, forces exerted on surrounding tissues (and entry into, damage to, non-target tissues), integrity, flow, surface conditions, patency and movement/migration of the implanted tube and to detect and monitor the properties of the fluids flowing through them. For example, the tubes (e.g., tympanostomy tubes, endotracheal tubes, tracheostomy tubes, nasogastric tubes, gastric tubes, feeding tubes, colostomy tubes, rectal tubes, and chest tubes) provided herein can have one or more contact sensors, strain gauge sensors, pressure sensors, fluid pressure sensors, position sensors, accelerometers, shock sensors, rotation sensors, vibration sensors, tilt sensors, pressure sensors, chemistry sensors, metabolic sensors, mechanical stress sensors and temperature sensors. Sensors can be placed at a density of greater than 1, 2, 3, 4, 5, 6, 7, 8, 9, 10 or greater than 10 sensors per square centimeter or at a density of greater than 1, 2, 3, 4, 5, 6, 7, 8, 9, 10 or greater than 10 sensors per cubic centimeter. Within either of these embodiments there can be less than 50, 75, 100, or 100 sensors per square centimeter, or per cubic centimeter.

The above sensors may be continuously monitored in order to provide a 'real-world' function, healing, and changes in function over time, to evaluate patient responses, and to better understand the conditions which tubes are exposed to in the real world.

B. Use of Medical Tubes to Deliver Therapeutic Agent(s)

As noted above, the present invention also provides drug-eluting tubes (e.g., balloon catheters, CVCs, endotracheal or chest tubes, drainage tubes, Foley catheters, hemodialysis access grafts and bypass grafts) which comprise one or more sensors, and which can be utilized to release a therapeutic agent (e.g., a drug) to a desired location within the body (e.g., a body lumen). For example, anti-restenotic drugs (e.g., paclitaxel, sirolimus, or an analog or derivative of these), can be administered to an atherosclerotic lesion utilizing a drug-eluting tube (e.g., a balloon catheter or a drug-coated balloon catheter as described in U.S. Pat. No. 7,491,188, U.S. Patent Application Nos. 2006/0079836, US 2009/0254063, US 2010/0023108, and US 2010/0042121). Within preferred embodiments one or more sensors (e.g., pressure sensors, contact sensors, and/or position sensors) can be utilized to determine appropriate placement of the desired drug, as well as the quantity of drug that is released at the desired site.

Within other embodiments of the invention a wide variety of additional therapeutic agents may be delivered (e.g., to prevent or treat an infection or to treat another disease state), including for example: Anthracyclines (e.g., gentamycin, tobramycin, doxorubicin and mitoxantrone); Fluoropyrimidines (e.g., 5-FU); Folic acid antagonists (e.g., methotrexate); Podophylotoxins (e.g., etoposide); Camptothecins; Hydroxyureas, and Platinum complexes (e.g., cisplatin) (see e.g., U.S. Pat. No. 8,372,420 which is incorporated by reference in its entirety. Other therapeutic agents include beta-lactam antibiotics (e.g., the penicillins, cephalosporins, carbacephems and carbapenems); aminoglycosides (e.g., sulfonamides, quinolones and the oxazolidinones); glycopeptides (e.g., vancomycin); lincosamides (e.g., clindamycin); lipopeptides; macrolides (e.g., azithromycin); monobactams; nitrofurans; polypeptides (e.g, bacitracin); and tetracyclines.

C. Use of Medical Tubes Having Sensors to Measure Flow, and Flow Obstruction

As noted above, within various aspects of the present invention tubes can be utilized to remove fluid from a patient (e.g., utilizing a drainage catheter); to provide fluid to a patient (e.g., a central venous catheter).

Hence, within one embodiment of the invention drainage catheters are provided with one or more sensors that can measure pressure change, and/or fluid flow. They can be utilized to determine whether fluid is draining from the patient, and in certain embodiments to advise a health care provider of impending blockage of the catheter.

Within other embodiments, catheters of the present invention can be utilized to determine whether fluid is flowing into a patient (e.g., in the case of a central venous line), and to determine the proper rate of fluid flow.

D. Methods for Monitoring Infection in Medical Tubes

Within other embodiments tubes (e.g., balloon catheters, CVCs, endotracheal or chest tubes, drainage tubes, Foley catheters, hemodialysis access grafts and bypass grafts) are provided comprising one or more temperature sensors. Such catheters can be utilized to measure the temperature of the catheter, and in the local tissue adjacent to the catheter. Methods are also provided for monitoring changes in temperature over time, in order to determine and/or provide notice (e.g., to a patient or a healthcare provider) that an infection may be imminent.

In certain embodiments of the present invention, metabolic and physical sensors can also be placed on or within the various components of a catheter in order to monitor for rare, but potentially life-threatening complications of catheters and medical tubes. In some patients, the catheter and surrounding tissues can become infected; typically from bacteria colonizing the patient's own skin that contaminate the surgical field or the device (often *Staphylococcus aureus* or *Staphylococcus epidermidis*). Sensors such as temperature sensors (detecting temperature increases), pH sensors (detecting pH decreases), and other metabolic sensors can be used to suggest the presence of infection on or around the catheter or medical tube. For example, temperature sensors may be included within one or more components of a catheter in order to allow early detection of infection could allow preemptive treatment with antibiotics or surgical drainage and eliminate the need to surgically remove the catheter.

Hence, within one embodiment of the invention methods are provided for determining an infection associated with a tube (e.g., a catheter), comprising the steps of a) providing to a body passageway of a subject a tube (e.g., catheter) as described herein, wherein the catheter comprises at least one temperature sensor and/or metabolic sensor, and b) detecting a change in said temperature sensor and/or metabolic sensor, and thus determining the presence of an infection. Within various embodiments of the invention the step of detecting may be a series of detections over time, and a change in the sensor is utilized to assess the presence or development of an infection. Within further embodiments a change of 0.5%, 1.0%, or 1.5% elevation of temperature or a metabolic factor over time (e.g., 0.5, 1.0, 1.5, 2.0, 2.5, 3.0, 3.5, 4 hours, 12 hours, 1 day, or 2 days) can be indicative of the presence of an infection (or a developing infection).

Within various embodiments of the invention an antibiotic may be delivered in order to prevent, inhibit or treat an infection subsequent to its detection. Representative examples of suitable antibiotics are well known, and are described above under Section B (the "Therapeutic Agents").

E. Further Uses of Sensor-Containing Medical Tubes (e.g., Catheters, Endotracheal or Chest Tubes and Bypass Grafts) in Healthcare Sensors on tubes (e.g., balloon catheters, CVCs, endotracheal or chest tubes, drainage tubes, Foley catheters, hemodialysis access grafts and bypass grafts), and any associated medical device has a variety of benefits in the healthcare setting, and in non-healthcare settings (e.g., at home or work). For example, postoperative progress can be monitored (readings compared from day-to-day, week-to-week, etc.) and the information compiled and relayed to both the patient and the attending physician allowing rehabilitation to be followed sequentially and compared to expected (typical population) norms. Within certain embodiments, a wearable device interrogates the sensors on a selected or randomized basis, and captures and/or stores the collected sensor data. This data may then be downloaded to another system or device (as described in further detail below).

Integrating the data collected by the sensors described herein (e.g., contact sensors, flow sensors, pressure sensors, position sensors, strain gauges and/or accelerometers) with simple, widely available, commercial analytical technologies such as pedometers and global positioning satellite (GPS) capability, allows further clinically important data to be collected such as, but not restricted to: extent of patient ambulation (time, distance, steps, speed, cadence), patient activity levels (frequency of activity, duration, intensity), exercise tolerance (work, calories, power, training effect), amount of catheter drainage (or fluid administration), catheter flow and patency, and catheter performance under various "real world" conditions. It is difficult to overstate the value of this information in enabling better management of the patient's recovery. An attending physician (or physiotherapist, rehabilitation specialist) only observes the patient episodically during scheduled visits; the degree of patient function at the exact moment of examination can be impacted by a multitude of disparate factors such as: the presence or absence of pain, the presence or absence of inflammation, time of day, compliance and timing of medication use (pain medications, anti-inflammatories), recent activity, patient strength, mental status, language barriers, the nature of their doctor-patient relationship, or even the patient's ability to accurately articulate their symptoms—to name just a few. Continuous monitoring and data collection can allow the patient and the physician to monitor progress objectively by supplying objective information about patient function under numerous conditions and circumstances, to evaluate how performance has been affected by various interventions (pain control, anti-inflammatory medication, rest, catheter repositioning, etc.), and to compare patient progress versus previous function and future expected function. Better therapeutic decisions and better patient compliance can be expected when both the doctor and the patient have the benefit of observing the impact of various treatment modalities on patient rehabilitation, activity, function and overall performance.

F. Generation of Power

Within certain aspects of the invention, a small electrical generation unit can be positioned along an outer, or alternatively an inner, surface of the catheter, or associated medical device. Briefly, a variety of techniques have been described for scavenging power from small mechanical movements or mechanical vibration. See, for example, the article entitled "Piezoelectric Power Scavenging of Mechanical Vibration Energy," by U. K. Singh et al., as published in the Australian Mining Technology Conference, Oct. 2-4, 2007, pp. 111-118, and the article entitled "Next Generation Micro-power Systems by Chandrakasan et al., as published in the 2008 Symposium on VLSI Circuits Digest of Technical Papers, pp. 1-5. See also U.S. Pat. No. 8,283, 793 entitled "Device for Energy Harvesting within a Vessel," and U.S. Pat. No. 8,311,632 entitled "Devices, Methods and Systems for Harvesting Energy in the Body," all of the above of which are incorporated by reference in their entirety. These references provide examples of different types of power scavengers which can produce electricity from very small motion and store the electricity for later use. The above references also describes embodiments in which pressure is applied and released from the particular structure in order to produce electricity without the need for motion, but rather as a result of the application of high pressure. In addition, these references describe embodiments wherein electricity can be produced from pulsatile forces, such as those found within a variety of structures within the body (e.g., within arterial or venous systems).

After the electricity is generated by one or more generators, the electricity is transmitted to any one of the variety of sensors which is described herein. For example, it can be transmitted to the sensors 22 shown in FIG. 17, FIG. 18 or FIG. 19 (including for example, contact sensors 22B, position sensors 24, pressure sensors 42 and/or temperature sensors 46). It may also be transmitted to the other sensors described herein. The transmission of the power can be carried out by any acceptable technique. For example, if the sensor is physically coupled to the implant, electric wires may run from the generator to the particular sensor. Alternatively, the electricity can be transmitted wirelessly in the same way that wireless smartcards receive power from closely adjacent power sources using the appropriate send and receive antennas. Such send and receive techniques of electric power are also described in the publication and the patent applications and issued U.S. patent previously described, all of which are incorporated herein by reference.

G. Medical Imaging and Self-Diagnosis of Assemblies Comprising Medical Tubes (e.g., Catheters, Endotracheal or Chest Tubes and Bypass Grafts); Predictive Analysis and Predictive Maintenance Within other aspects of the invention methods are provided for imaging a catheter and/or an associated medical device (e.g., a stent, guidewire and/or associated medical instrument) as provided herein, comprising the steps of (a) detecting the location of one or more sensors in a catheter, and/or associated medical device; and (b) visually displaying the location of said one or more sensors, such that an image of the catheter is created. Within various embodiments, the step of detecting may be done over time, and the visual display may thus show positional movement over time. Within certain preferred embodiments the image which is displayed is a three-dimensional image. Within other embodiment, the imaging techniques may be utilized post-insertion in order to examine the catheter, and/or to compare operation and/or movement of the device over time.

The present invention provides tubes (e.g., balloon catheters, CVCs, endotracheal or chest tubes, drainage tubes, Foley catheters, hemodialysis access grafts and bypass grafts) and associated medical devices which are capable of imaging through the use of sensors over a wide variety of conditions. For example, within various aspects of the invention methods are provided for imaging a catheter [or portion thereof (e.g., a medical device or kit as described herein)] or an assembly comprising a catheter, medical device or kit (as described herein) with sensors, comprising the steps of detecting the changes in sensors in, on, and/or within a catheter, medical device or kit over time, and wherein the catheter, medical device or kit comprises sensors at a density of greater than 1, 2, 3, 4, 5, 6, 7, 8, 9, 10 or greater than 10 sensors per square centimeter. Within other aspects the catheter, medical device or kit comprises sensors at a density of greater than 1, 2, 3, 4, 5, 6, 7, 8, 9, 10 or greater than 10 sensors per cubic centimeter. Within either of these embodiments there can be less than 50, 75, 100, or 100 sensors per square centimeter, or per cubic centimeter. Within various embodiments the at least one or more of the sensors may be placed randomly, or at one or more specific locations within the catheter, medical device, or kit as described herein. As noted above, a wide variety of sensors can be utilized therein, including for example, contact sensors, strain gauge sensors, pressure sensors, fluid pressure sensors, position sensors, pulse pressure sensors, liquid (e.g., blood) volume sensors, liquid (e.g., blood) flow sensors, liquid (e.g., blood, urine) chemistry sensors, liquid (e.g., blood, urine) metabolic sensors, mechanical stress sensors, and temperature sensors.

For example, a catheter, medical device, or kit comprising sensors as described herein can be utilized to image anatomy through sensors which can detect positional movement. The sensors used can also include accelerometers and motion sensors to detect movement of the catheter due to a variety of physical changes. Changes in the position of the accelerometers and/or motion sensors over time can be used as a measurement of changes in the position of the catheter over time. Such positional changes can be used as a surrogate marker of catheter anatomy—i.e. they can form an "image" of the catheter to provide information on the size, shape and location of changes to the catheter, and/or catheter movement/migration.

Certain exemplary embodiments will now be explained in more detail. One particular benefit is the live and in-situ monitoring of the patient's recovery and the implanted catheter 10. The sensors as described herein are collecting data on a constant basis, during normal daily activities and even during the night if desired. For example, the contact sensors can obtain and report data once every 10 seconds, once a minute, or once a day. Other sensors will collect data more frequently, such as several times a second. For example, it would be expected that the flow, pressure, temperature, contact, and/or position data would be collected and stored several times a second. Other types of data might only need to be collected by the minute or by the hour. Still other sensors may collect data only when signaled by the patient to do so (via an external signaling/triggering device) as part of "event recording"—i.e. when the patient experiences a particular event (e.g. pain, injury, increased/decreased drainage, etc.)—and signals the device to obtain a reading at that time in order to allow the comparison of subjective/symptomatic data to objective/sensor data in an effort to better understand the underlying cause or triggers of the patient's symptoms.

In certain instances the tube (e.g. catheter) is of sufficient size and has more than sufficient space in order to house one or more processor circuits, CPUs, memory chips and other electrical circuits as well as antennas for sending and receiving the data. Within other embodiments, the associated medical device may be able to house the one or more processor circuits, CPUs, memory chips and other electrical circuits as well as antennas for sending and receiving the data. Processors can be programmed to collect data from the various sensors on any desired schedule as set by the medical professional. All activity can be continuously monitored post operation or post-procedure and the data collected and stored in the memory located inside the implant.

A patient will generally have regular medical checkups. When the patient goes to the doctor's office for a medical checkup, the doctor will bring a reading device closely adjacent to the catheter 10, in this example a catheter, in order to transfer the data from the internal circuit inside the implant to the database in the physician's office. The use of wireless transmission using smartcards or other techniques is very well known in the art and need not be described in detail. Examples of such wireless transmission of data are provided in the published patent applications and patents which have been described herein. The data which has been collected (e.g., over a short period of time, over several weeks or even several months) is transferred in a few moments from the memory which is positioned in the implant to the doctor's computer or wireless device. The computer therefore analyzes the data for anomalies, unexpected changes over time, positive or negative trends, and other signs which may be indicative of the health of the patient and the operability of the catheter. For example, if the patient has decided to go skiing or jogging, the doctor will be able to monitor the effect of such activity on the catheter 10, including the accelerations and strains during the event itself. The doctor can then look at the health of the catheter in the hours and days after the event and compare it to data prior to the event to determine if any particular event caused long term damage, or if the activities subjected the catheter to forces beyond the manufacturer's performance specifications for that particular catheter. Data can be collected and compared with respect to the ongoing and long term performance of the catheter from the flow sensors, pressure sensors, strain gauges, the contact sensors, the surface wear sensors, or other sensors which may be present.

In one alternative, the patient may also have such a reading device in their home which collates the data from the catheter on a periodic basis, such as once per day or once per week. As described above, the patient may also be able to "trigger" a device reading (via an external signaling/triggering device) as part of "event recording." Empowering the patient to follow their own rehabilitation—and enabling them to see the positive (and negative) effects of various lifestyle choices on their health and rehabilitation—can be expected to improve compliance and improve patient outcomes (for example changes in the metabolic readings in a dialysis patient). Furthermore, their experience can be shared via the web with other patients to compare their progress versus expected "norms" for function and rehabilitation and alert them to signs and symptoms that should be brought to their doctor's attention. The performance of different catheters can be compared in different patients (different sexes, weights, activity levels, etc.) to help manufacturers design better devices and assist surgeons and other healthcare providers in the selection of the right catheter for specific patient types. Payers, patients, manufacturers and physicians could all benefit from the collection of this comparative information. Lastly, data accumulated at home can be collected and transmitted via the Internet to the physician's office for analysis—potentially eliminating unnecessary visits in some cases and encouraging immediate medical follow-up in others.

H. Methods of Monitoring Assemblies Comprising Tubes (e.g., Catheters, Endotracheal or Chest Tubes and Bypass Grafts)

Figure 17:
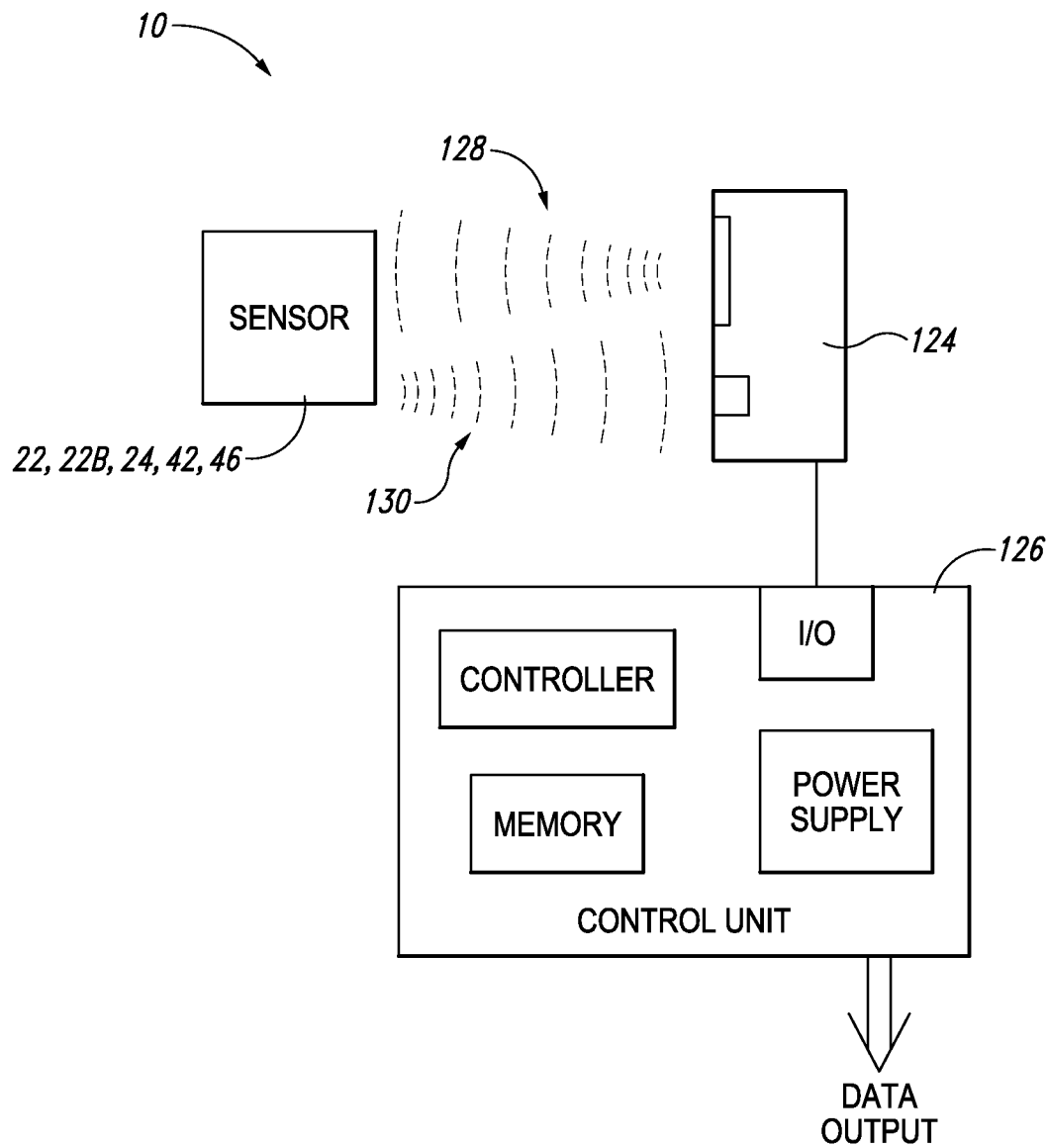
FIG. 17 illustrates an information and communication technology system embodiment arranged to process sensor data.

As noted above, the present invention also provides methods for monitoring one or more of the catheter assemblies provided herein. For example, FIG. 17 illustrates a monitoring system usable with the catheter 10 as of the type shown in any one of the Figures described above. The monitoring system includes one or more sensors 22 (including for example, contact sensors 22B, position sensors 24, pressure sensors 42, and/or temperature sensors 46) an interrogation module 124, and a control unit 126. The sensor (e.g., 22, 26, 27 and/or 28) can be passive, wireless type which can operate on power received from a wireless source. Such sensors of this type are well known in the art and widely available. A pressure sensor of this type might be a MEMS pressure sensor, for example, Part No. LPS331AP, sold on the open market by STMicroelectronics. MEMS pressure sensors are well known to operate on very low power and suitable to remain unpowered and idle for long periods of time. They can be provided power wirelessly on an RF signal and, based on the power received wirelessly on the RF signal, perform the pressure sensing and then output the sensed data.

In one embodiment, an electrical generation system (as described above) is provided that can be utilized to power the sensors described herein. During operation, as shown in FIG. 17, an interrogation module 124 outputs a signal 128. The signal 128 is a wireless signal, usually in the RF band, that contains power for the sensors 22 as well as an interrogation request that the sensors perform a sensing. Upon being interrogated with the signal 128, the sensors 22 powers up and stores power in onboard capacitors sufficient to maintain operation during the sensing and data reporting. Such power receiving circuits and storing on onboard capacitors are well known in the art and therefore need not be shown in detail. The appropriate sensing is carried out by the sensors 22 and then the data is output from the sensor back to the interrogation module 124 on a signal 130, where it is received at an input port of the integration module.

According to one embodiment, sufficient signal strength is provided in the initial signal 128 to provide power for the sensor and to carry out the sensing operation and output the signal back to the interrogation module 124. In other embodiments, two or more signals 128 are sent, each signal providing additional power to the sensor to permit it to complete the sensing operation and then provide sufficient power to transfer the data via the signal path 130 back to the interrogation module 124. For example, the signal 128 can be sent continuously, with a sensing request component at the first part of the signal and then continued providing, either as a steady signal or pulses to provide power to operate the sensor. When the sensor is ready to output the data, it sends a signal alerting the interrogation module 124 that data is coming and the signal 128 can be turned off to avoid interference. Alternatively, the integration signal 128 can be at a first frequency and the output signal 130 at a second frequency separated sufficiently that they do not interfere with each other. In a preferred embodiment, they are both the same frequency so that the same antenna on the sensor can receive the signal 128 and send signal 130.

The interrogation signal 128 may contain data to select specific sensors on the catheter. For example, the signal 128 may power up all sensors on the catheter at the same time and then send requests for data from each at different selected times so that with one interrogation signal 128 provided for a set time, such as 1-2 seconds, results in each of the sensors on the catheter collecting data during this time period and then, at the end of the period, reporting the data out on respective signals 130 at different times over the next 0.5 to 2 seconds so that with one interrogation signal 128, the data from all sensors 22 is collected.

The interrogation module 124 is operating under control of the control unit 126 which has a microprocessor for the controller, a memory, an I/O circuit to interface with the interrogation module and a power supply. The control unit may output data to a computer or other device for display and use by the physician to treat the subject.

Figure 18:
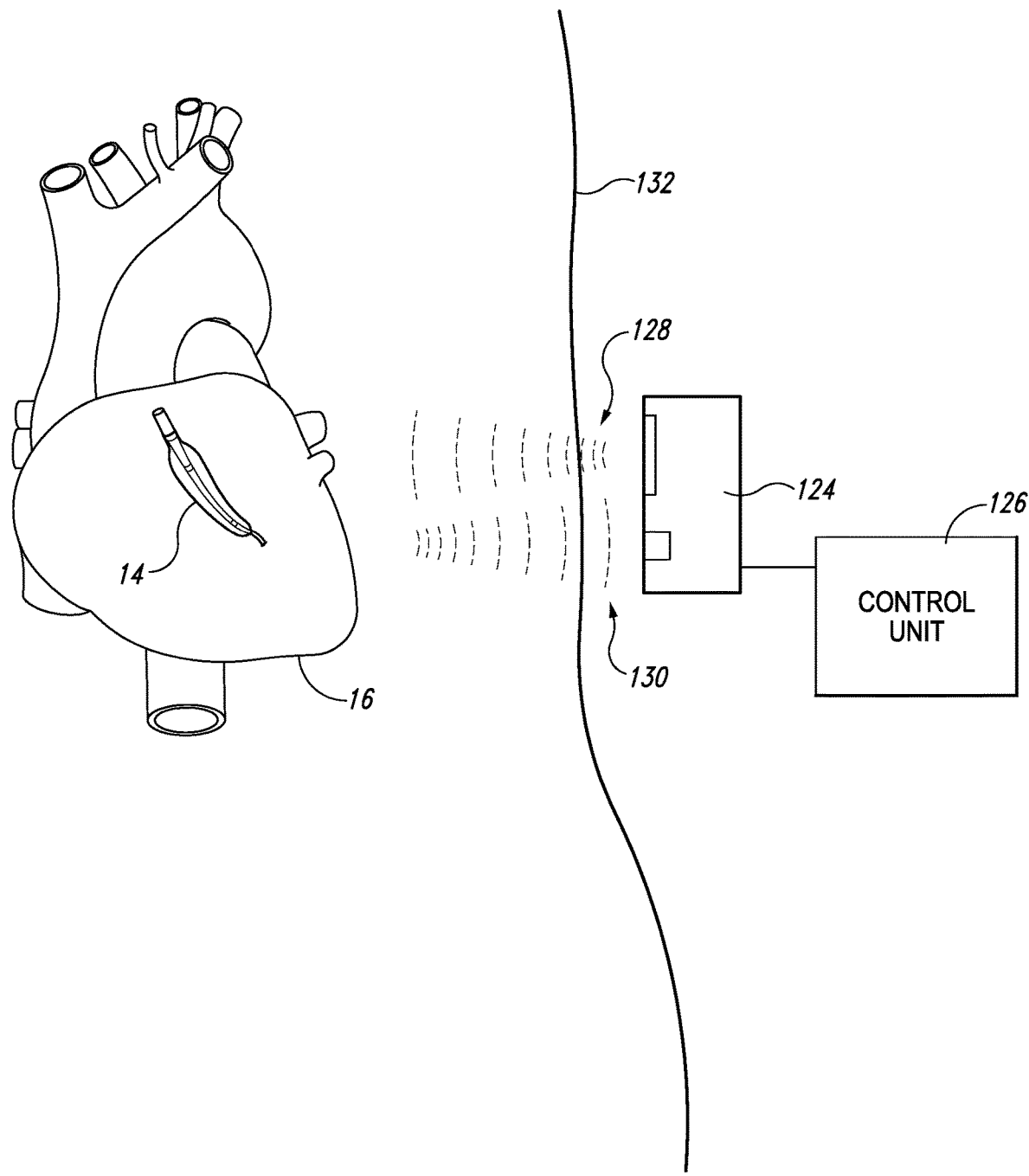
FIG. 18 is a block diagram of a sensor, interrogation module, and a control unit according to one embodiment of the invention.

FIG. 18 illustrates the operation according to a preferred embodiment within a subject. The subject has an outer skin 132. As illustrated in FIG. 13, the interrogation module 124 and control unit 126 are positioned outside the skin 132 of the subject. The interrogation signal 128 passes through the skin of the subject with a wireless RF signal, and the data is received on a wireless RF signal 130 from the sensors within the balloon catheter 14, which is positioned within the heart 16, back to the interrogation module 124. While the wireless signal can be in any frequency range, an RF range is preferred. A frequency in the VLF to LF ranges of between 3-1300 kHz is preferred to permit the signal to be carried to sufficient depth inside the body with low power, but frequencies below 3 kHz and above 1300 kHz can also be used. The sensing does not require a transfer of large amounts of data and low power is preferred; therefore, a low frequency RF signal is acceptable. This also avoids competition from and inadvertent activation by other wireless signal generators, such as blue tooth, cell phones and the like.

I. Collection, Transmission, Analysis, and Distribution of Data from Assemblies Comprising Tubes (e.g., Catheters, Endotracheal or Chest Tubes and Bypass Grafts)

Figure 19:
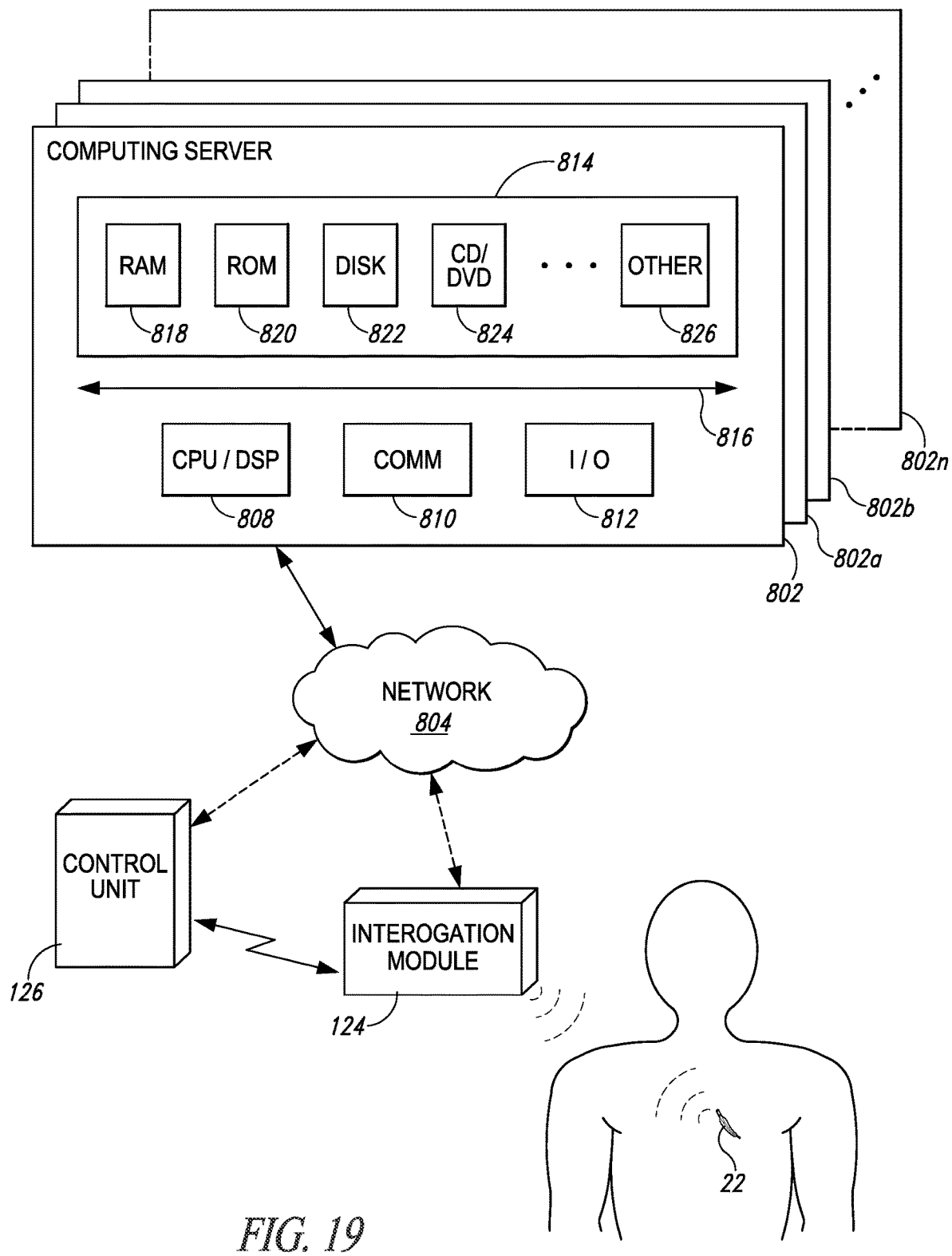
FIG. 19 is a schematic illustration of one or more sensors positioned on a catheter within a subject which is being probed for data and outputting data, according to one embodiment of the invention.

FIG. 19 illustrates one embodiment of an information and communication technology (ICT) system 800 arranged to process sensor data (e.g., data from the sensors 22). In FIG. 19, the ICT system 800 is illustrated to include computing devices that communicate via a network 804, however in other embodiments, the computing devices can communicate directly with each other or through other intervening devices, and in some cases, the computing devices do not communicate at all. The computing devices of FIG. 19 include computing servers 802, control units 126, interrogation units 124, and other devices that are not shown for simplicity.

In FIG. 19, one or more sensors 22 communicate with an interrogation module 124. The interrogation module 124 of FIG. 19 is directed by a control unit 126, but in other cases, interrogation modules 124 operates autonomously and passes information to and from sensors 22. One or both of the interrogation module 124 and control unit 126 can communicate with the computing server 802.

Within certain embodiments, the interrogation module and/or the control unit may be a wearable device on the subject. The wearable device (e.g., a watch-like device, a wrist-band, glasses, or other device that may be carried or worn by the subject) can interrogate the sensors over a set (or random) period of time, collect the data, and forward the data on to one or more networks (804). Furthermore, the wearable device may collect data of its own accord which can also be transmitted to the network. Representative examples of data that may be collected include location (e.g., a GPS), body or skin temperature, and other physiologic data (e.g., pulse). Within yet other embodiments, the wearable device may notify the subject directly of any of a number of prescribed conditions, including but not limited to possible or actual failure of the device.

The information that is communicated between an interrogation module 124 and the sensors 22, may be useful for many purposes as described herein. In some cases, for example, sensor data information is collected and analyzed expressly for the health of an individual subject. In other cases, sensor data is collected and transmitted to another computing device to be aggregated with other data (for example, the sensor data from 22 may be collected and aggregated with other data collected from a wearable device (e.g., a device that may, in certain embodiments, include GPS data and the like).

FIG. 19 illustrates aspects of a computing server 802 as a cooperative bank of servers further including computing servers 802a, 802b, and one or more other servers 802n. It is understood that computing server 802 may include any number of computing servers that operate individually or collectively to the benefit of users of the computing servers.

In some embodiments, the computing servers 802 are arranged as cloud computing devices created in one or more geographic locations, such as the United States and Canada. The cloud computing devices may be created as MICROSOFT AZURE cloud computing devices or as some other virtually accessible remote computing service.

An interrogation module 124 and a control unit 126 are optionally illustrated as communicating with a computing server 802. Via the interrogation module 124 or control unit 126, sensor data is transferred to (and in addition or alternatively from) a computing server 802 through network 804.

The network 804 includes some or all of cellular communication networks, conventional cable networks, satellite networks, fiber-optic networks, and the like configured as one or more local area networks, wide area networks, personal area networks, and any other type of computing network. In a preferred embodiment, the network 804 includes any communication hardware and software that cooperatively works to permit users of computing devices to view and interact with other computing devices.

Computing server 802 includes a central processing unit (CPU) digital signal processing unit (DSP) 808, communication modules 810, Input/Output (I/O) modules 812, and storage module 814. The components of computing server 802 are cooperatively coupled by one or more buses 816 that facilitate transmission and control of information in and through computing server 802. Communication modules 810 are configurable to pass information between the computer server 802 and other computing devices (e.g., computing servers 802a, 802b, 802n, control unit 126, interrogation unit 124, and the like). I/O modules 812 are configurable to accept input from devices such as keyboards, computer mice, trackballs, and the like. I/O modules 812 are configurable to provide output to devices such as displays, recorders, LEDs, audio devices, and the like.

Storage module 814 may include one or more types of storage media. For example, storage module 814 of FIG. 19 includes random access memory (RAM) 818, read only memory (ROM) 810, disk based memory 822, optical based memory 8124, and other types of memory storage media 8126. In some embodiments one or more memory devices of the storage module 814 has configured thereon one or more database structures. The database structures may be used to store data collected from sensors 22.

In some embodiments, the storage module 814 may further include one or more portions of memory organized a non-transitory computer-readable media (CRM). The CRM is configured to store computing instructions executable by a CPU 808. The computing instructions may be stored as one or more files, and each file may include one or more computer programs. A computer program can be standalone program or part of a larger computer program. Alternatively or in addition, each file may include data or other computational support material for an application that directs the collection, analysis, processing, and/or distribution of data from sensors (e.g., catheter sensors). The sensor data application typically executes a set of instructions stored on computer-readable media.

It will be appreciated that the computing servers shown in the figures and described herein are merely illustrative and are not intended to limit the scope of the present invention. Computing server 802 may be connected to other devices that are not illustrated, including through one or more networks such as the Internet or via the Web that are incorporated into network 804. More generally, a computing system or device (e.g., a "client" or "server") or any part thereof may comprise any combination of hardware that can interact and perform the described types of functionality, optionally when programmed or otherwise configured with software, including without limitation desktop or other computers, database servers, network storage devices and other network devices, PDAs, cell phones, glasses, wrist bands, wireless phones, pagers, electronic organizers, Internet appliances, television-based systems (e.g., using set-top boxes and/or personal/digital video recorders), and various other products that include appropriate inter-communication capabilities. In addition, the functionality provided by the illustrated system modules may in some embodiments be combined in fewer modules or distributed in additional modules. Similarly, in some embodiments the functionality of some of the illustrated modules may not be provided and/or other additional functionality may be available.

In addition, while various items are illustrated as being stored in memory or on storage while being used, these items or portions of them can be transferred between memory and other storage devices for purposes of memory management and/or data integrity. In at least some embodiments, the illustrated modules and/or systems are software modules/systems that include software instructions which, when executed by the CPU/DSP 808 or other processor, will program the processor to automatically perform the described operations for a module/system. Alternatively, in other embodiments, some or all of the software modules and/or systems may execute in memory on another device and communicate with the illustrated computing system/device via inter-computer communication.

Furthermore, in some embodiments, some or all of the modules and/or systems may be implemented or provided in other manners, such as at least partially in firmware and/or hardware means, including, but not limited to, one or more application-specific integrated circuits (ASICs), standard integrated circuits, controllers (e.g., by executing appropriate instructions, and including microcontrollers and/or embedded controllers), field-programmable gate arrays (FP-GAs), complex programmable logic devices (CPLDs), and the like. Some or all of the systems, modules, or data structures may also be stored (e.g., as software instructions or structured data) on a transitory or non-transitory computer-readable storage medium 814, such as a hard disk 822 or flash drive or other non-volatile storage device 8126, volatile 818 or non-volatile memory 810, a network storage device, or a portable media article (e.g., a DVD disk, a CD disk, an optical disk, a flash memory device, etc.) to be read by an appropriate input or output system or via an appropriate connection. The systems, modules, and data structures may also in some embodiments be transmitted as generated data signals (e.g., as part of a carrier wave or other analog or digital propagated signal) on a variety of computer readable transmission mediums, including wireless-based and wired/cable-based mediums. The data signals can take a variety of forms such as part of a single or multiplexed analog signal, as multiple discrete digital packets or frames, as a discrete or streaming set of digital bits, or in some other form. Such computer program products may also take other forms in other embodiments. Accordingly, the present invention may be practiced with other computer system configurations.

In FIG. 19, sensor data from, e.g., sensors 22 is provided to computing server 802. Generally speaking, the sensor data, represents data retrieved from a known subject and from a known sensor. The sensor data may possess include or be further associated with additional information such as the USI, UDI, a time stamp, a location (e.g., GPS) stamp, a date stamp, and other information. The differences between various sensors is that some may include more or fewer data bits that associate the data with a particular source, collection device, transmission characteristic, or the like.

In some embodiments, the sensor data may comprise sensitive information such as private health information associated with a specific subject. Sensitive information, for example sensor data from sensors e.g., 22, may include any information that an associated party desires to keep from wide or easy dissemination. Sensitive information can stand alone or be combined with other non-sensitive information. For example, a subject's medical information is typically sensitive information. In some cases, the storage and transmission of a subject's medical information is protected by a government directive (e.g., law, regulation, etc.) such as the U.S. Health Insurance Portability and Accountability Act (HIPPA).

As discussed herein, a reference to "sensitive" information includes information that is entirely sensitive and information that is some combination of sensitive and non-sensitive information. The sensitive information may be represented in a data file or in some other format. As used herein, a data file that includes a subject's medical information may be referred to as "sensitive information." Other information, such as employment information, financial information, identity information, and many other types of information may also be considered sensitive information.

A computing system can represent sensitive information with an encoding algorithm (e.g., ASCII), a well-recognized file format (e.g., PDF), or by some other format. In a computing system, sensitive information can be protected from wide or easy dissemination with an encryption algorithm.

Generally speaking, sensitive information can be stored by a computing system as a discrete set of data bits. The set of data bits may be called "plaintext." Furthermore, a computing system can use an encryption process to transform plaintext using an encryption algorithm (i.e., a cipher) into a set of data bits having a highly unreadable state (i.e., cipher text). A computing system having knowledge of the encryption key used to create the cipher text can restore the information to a plaintext readable state. Accordingly, in some cases, sensitive data (e.g., sensor data 806*a*, 806*b*) is optionally encrypted before being communicated to a computing device.

In one embodiment, the operation of the information and communication technology (ICT) system 800 of FIG. 19 includes one or more sensor data computer programs stored on a computer-readable medium. The computer program may optionally direct and/or receive data from one or more catheter sensors implanted in one or more subjects. A sensor data computer program may be executed in a computing server 802. Alternatively, or in addition, a sensor data computer program may be executed in a control unit 126, an interrogation unit 124.

In one embodiment, a computer program to direct the collection and use of catheter sensor data is stored on a non-transitory computer-readable medium in storage module 814. The computer program is configured to identify a subject who has a wireless catheter inserted in his or her body. The wireless catheter may include one or more wireless sensors.

In some cases, the computer program identifies one subject, and in other cases, two or more subjects are identified. The subjects may each have one or more wireless tubes (e.g., catheters, endotracheal or chest tubes and bypass grafts), and each wireless catheter may have one or more wireless sensors of the type described herein.

The computer program is arranged to direct the collection of sensor data from the wireless catheter devices. The sensor data is generally collected with a wireless interrogation unit 124. In some cases, the program communicates with the wireless interrogation unit 124. In other cases, the program communicates with a control unit 126, which in turn directs a wireless interrogation unit 124. In still other cases, some other mechanism is used direct the collection of the sensor data.

Once the sensor data is collected, the data may be further processed. For example, in some cases, the sensor data includes sensitive subject data, which can be removed or disassociated with the data. The sensor data can be individually stored (e.g., by unique sensor identification number, device number, etc.) or aggregated together with other sensor data by sensor type, time stamp, location stamp, date stamp, subject type, other subject characteristics, or by some other means.

The following pseudo-code description is used to generally illustrate one exemplary algorithm executed by a computing server 802 and generally described herein with respect to FIG. 19:

```
Start
   Open a secure socket layer (SSL)
   Identify a subject
   Communicate with a predetermined control unit
   Request sensor data from the subject via the control unit
   Receive sensor data
   If the sensor data is encrypted
      THEN decrypt the sensor data
   Store encrypted data in the selected storage locations
   Aggregate the sensor data with other sensor data
   Store encrypted data in the selected storage locations
   Maintain a record of the storage transaction
   Perform post storage actions
End
```

Those skilled in the art will recognize that it is common within the art to implement devices and/or processes and/or systems, and thereafter use engineering and/or other practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Qwest, Southwestern Bell, etc.), or (g) a wired/wireless services entity (e.g., AT&T, T-Mobile, Verizon), etc.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory. Further, implementation of at least part of a system for performing a method in one territory does not preclude use of the system in another territory.

In conclusion, tubes (e.g., balloon catheters, CVCs, endotracheal or chest tubes, drainage tubes, Foley catheters, hemodialysis access grafts and bypass grafts) utilizing a variety of sensors can be utilized to serve a variety of critical clinical functions, such as safe, accurate and less traumatic placement and deployment of the catheter, procedural and post-operative "real time" imaging of catheter and the surrounding anatomy, the development of catheter complications, and the patient's overall health status. Currently, post-operative (both in hospital and out-patient) evaluation of catheter patients is through patient history, physical examination and medical monitoring that is supplemented with diagnostic imaging studies as required. However, most of the patient's recuperative period occurs between hospital and office visits and the majority of data on daily function goes uncaptured; furthermore, monitoring patient progress through the use of some diagnostic imaging technology can be expensive, invasive and carry its own health risks (the use of nuclear isotopes or certain dyes). It can, therefore, be very difficult to accurately measure and follow the development or worsening of symptoms and evaluate "real life" catheter performance, particularly as they relate to patient activity levels, flow rate, drainage, and the effectiveness of rehabilitation efforts and medications.

At present, neither the physician nor the patient has access to the type of "real time," continuous, objective, catheter performance measurements that they might otherwise like to have. Being able to monitor in situ catheter function, flow rates, integrity, anatomy and physiology can provide the physician with valuable objective information during office visits; furthermore, the patient can take additional readings at home at various times (e.g. when experiencing pain, during exercise, after taking medications, etc.) to provide important complementary clinical information to the doctor (which can be sent to the healthcare provider electronically even from remote locations). From the perspective of the patient, being able to monitor many of these same parameters at home allows them to take a more proactive role in their care and recovery and provide him or her with either an early warning indicator to seek medical assistance or with reassurance.

In one alternative, the patient may have a reading device in their home which collates the data from the catheter on a periodic basis, such as once per day or once per week. In addition to empowering the patient to follow their own rehabilitation—and enabling them to see the positive (and negative) effects of various lifestyle choices on their health and rehabilitation—such information access can be expected to improve compliance and improve patient outcomes. For example, within certain embodiments the devices and systems provided herein can instruct and/or notify the patient, or a permitted third-party as to deviations (e.g., greater than 10%, 20%, 25%, 50%, 70%, and or 100%) from normal, and/or, set parameters. Furthermore, their recovery experience can be shared via the web with other patients to compare their progress versus expected "norms" for function and rehabilitation and alert them to signs and symptoms that should be brought to their doctor's attention. From a public health perspective, the performance of different tubes (e.g., balloon catheters, CVCs, endotracheal or chest tubes, drainage tubes, Foley catheters, hemodialysis access grafts and bypass grafts) can be compared in different patients (different sexes, disease severity, activity levels, concurrent diseases such as hypertension, heart disease, kidney disease and diabetes, smoking status, obesity, etc.) to help manufacturers design better tubes (e.g., balloon catheters, CVCs, endotracheal or chest tubes, drainage tubes, Foley catheters, hemodialysis access grafts and bypass grafts) and assist physicians in the selection of the right catheter for a specific patient types. Payers, patients, manufacturers and physicians could all benefit from the collection of this comparative information. Poor and dangerous products could be identified and removed from the market and objective long-term effectiveness data collected and analyzed. Lastly, data accumulated at home can be collected and transmitted via the Internet to the physician's office for analysis—potentially eliminating unnecessary visits in some cases and encouraging immediate medical follow-up in others.

Conventions

In general, and unless otherwise specified, all technical and scientific terms used herein shall have the same meaning as those commonly understood by one of ordinary skill in the art to which the embodiment pertains. For convenience, the meanings of selected terms are provided below, where these meanings are provided in order to aid in describing embodiments identified herein. Unless stated otherwise, or unless implicit from the context in which the term is used, the meanings provided below are the meanings intended for the referenced term.

Embodiment examples or feature examples specifically provided are intended to be exemplary only, that is, those examples are non-limiting on an embodiment. The term "e.g." (latin, exempli gratia) is used herein to refer to a non-limiting example, and effectively means "for example".

Singular terms shall include pluralities and plural terms shall include the singular, unless otherwise specified or required by context. For example, the singular terms "a", "an" and "the" include plural referents unless the context clearly indicates otherwise. Similarly, the term "or" is intended to include "and" unless the context clearly indicates otherwise.

Except in specific examples provided herein, or where otherwise indicated, all numbers expressing quantities of a component should be understood as modified in all instances by the term "about", where "about" means ±5% of the stated value, e.g., 100 refers to any value within the range of 95-105.

The terms comprise, comprising and comprises are used to identify essential features of an embodiment, where the embodiment may be, for example, a composition, device, method or kit. The embodiment may optionally contain one or more additional unspecified features, and so the term comprises may be understood to mean includes.

The following are some specific numbered embodiments of the systems and processes disclosed herein. These embodiments are exemplary only. It will be understood that the invention is not limited to the embodiments set forth herein for illustration, but embraces all such forms thereof as come within the scope of the above disclosure.

1) A medical tube comprising:
a medical tube and one or more sensors positioned within or upon said medical tube.

2) The medical tube of embodiment 1 wherein said one or more sensors includes a sensor within the matrix of the medical tube.

3) The medical tube of embodiment 1 wherein said one or more sensors includes a sensor within or upon said medical tube.

4) The medical tube according to any one of embodiments 1 to 4 wherein said sensor is selected from the group consisting of fluid pressure sensors, contact sensors, position sensors, pulse pressure sensors, liquid volume sensors, liquid flow sensors, chemistry sensors, metabolic sensors, accelerometers, mechanical stress sensors and temperature sensors.

5) The medical tube according to embodiment 1 wherein said medical tube is a catheter.

6) The medical tube according to embodiment 5 wherein said catheter is a balloon catheter.

7) The medical tube according to embodiment 1 wherein said medical tube is a graft or drainage tube 8) A medical device, comprising a balloon catheter according to embodiment 6, and a stent comprising one or more sensors.

9) The medical device according to embodiment 8 wherein said sensor on said stent is selected from the group consisting of accelerometers, pressure sensors, contact sensors, position sensors, chemical microsensors, tissue metabolic sensors, mechanical stress sensors and temperature sensors.

10) The medical device according to embodiment 9 wherein said accelerometer detects acceleration, tilt, vibration, shock and or rotation.

11) The medical tube according to any one of embodiments 1 to 7 or medical device according to any one of embodiments 9 or 10 further comprising:
an electronic processor positioned upon and/or inside the catheter or medical device that is electrically coupled to sensors.

12) The catheter or medical device according to embodiment 11 wherein the electric coupling is a wireless coupling.

13) The tube or medical device according to embodiment 11 further including:
a memory coupled to the electronic processor and positioned upon and/or inside the tube or medical device.

14) A kit comprising the tube according to any one of embodiments 1 to 15, further comprising a guidewire.

15) The kit according to embodiment 14 wherein said guidewire further comprises one or more sensors position on or within said guidewire.

16) The tube, medical device or kit according to any one of embodiments 1 to 15 wherein said sensor is a plurality of sensors which are positioned on or within said tube, medical device and/or kit at a density of greater than 1, 2, 3, 4, 5, 6, 7, 8, 9, 10 or 20 sensors per square centimeter.

17) The tube, medical device or kit according to any one of embodiments 1 to 15 wherein said sensor is a plurality of sensors which are positioned on or within said tube, medical device and/or kit at a density of greater than 1, 2, 3, 4, 5, 6, 7, 8, 9, 10 or 20 sensors per cubic centimeter.

18) The tube, medical device, or kit according to any one of embodiments 1 to 17 wherein said sensors are placed randomly within the tube, medical device or kit.

19) The tube, medical device, or kit according to any one of embodiments 1 to 18 wherein the one or more of the sensors are placed at specific locations within the tube, medical device or kit.

20) A method comprising:
obtaining data from a sensor positioned at a plurality of locations between on and/or within a tube, medical device or kit according to any one of embodiments 1 to 19 of a subject;
storing the data in a memory device located on or within the tube, medical device or kit; and
transferring the data from the memory to a location outside the tube or medical device.

21) A method according to embodiment 20, further comprising the step of analyzing said data.

22) A method for detecting and/or recording an event in a subject with a tube, medical device or kit as provided in any one of embodiments 1 to 19, comprising the step of interrogating at a desired point in time the activity of one or more sensors within the tube, medical device or kit, and recording said activity.

23) The method according to embodiment 22 wherein the step of interrogating is performed by a subject which has an implanted tube, and the step of recording is performed on a wearable device.

24) The method according to any one of embodiments 22, or 23, wherein said recording is provided to a health care provider.

25) A method for imaging a tube, medical device or kit, comprising the steps of
   (a) detecting the location of one or more sensors of a tube, medical device or kit according to any one of embodiments 1 to 19; and
   (b) visually displaying the location of said one or more sensors, such that an image of the tube, medical device or kit is created.

26) The method according to embodiment 25 wherein the step of detecting occurs over time.

27) The method according to embodiment 25 or 26, wherein said visual display shows changes in the positions of said sensors over time, and/or changes in temperature of the sensors or surrounding tissue over time.

28) The method according to any one of embodiments 25 to 27 wherein said visual display is a three-dimensional image of said tube.

29) A method for inserting a tube, medical device or kit into a subject, comprising the steps of
   (a) inserting a tube, medical device or kit according to any one of embodiments 1 to 19 into a subject; and
   (b) imaging the placement of said tube, medical device or kit according to the method of any one of embodiments 25 to 28.

30) A method for examining a tube, medical device or kit according to any one of embodiments 1 to 19 which has been previously inserted into a patient, comprising the step of imaging the tube according to the method of any one of embodiments 25 to 28.

31) A method of monitoring a tube, medical device, or kit within a subject, comprising:
   transmitting a wireless electrical signal from a location outside the body to a location inside the subject's body;
   receiving the signal at a sensor positioned on a tube, medical device, or kit according to any one of embodiments 1 to 19 located inside the body;
   powering the sensor using the received signal;
   sensing data at the sensor; and
   outputting the sensed data from the sensor to a receiving unit located outside of the body.

32) The method according to embodiment 31 wherein said receiving unit is a watch, wrist band, cell phone or glasses.

33) The method according to embodiments 31 or 32 wherein said receiving unit is located within a subject's residence or office.

34) The method according to embodiments any one of embodiments 31 to 33 wherein said sensed data is provided to a health care provider.

35) The method according to any one of embodiments 31 to 34 wherein said sensed data is posted to one or more websites.

36) A non-transitory computer-readable storage medium whose stored contents configure a computing system to perform a method, the method comprising:
   identifying a subject, the identified subject having at least one wireless tube, medical device, or kit according to any one of embodiments 1 to 19, each wireless tube, medical device, or kit having one or more wireless sensors;
   directing a wireless interrogation unit to collect sensor data from at least one of the respective one or more wireless sensors; and
   receiving the collected sensor data.

37) The non-transitory computer-readable storage medium of embodiment 36 whose stored contents configure a computing system to perform a method, the method further comprising:
   identifying a plurality of subjects, each identified subject having at least one wireless tube, medical device, or kit, each wireless tube, medical device, or kit having one or more wireless sensors;
   directing a wireless interrogation unit associated with each identified subject to collect sensor data from at least one of the respective one or more wireless sensors;
   receiving the collected sensor data; and
   aggregating the collected sensor data.

38) The non-transitory computer-readable storage medium of embodiment 36 whose stored contents configure a computing system to perform a method, the method further comprising:
   removing sensitive subject data from the collected sensor data; and
   parsing the aggregated data according to a type of sensor.

39) The non-transitory computer-readable storage medium of embodiment 36 whose stored contents configure a computing system to perform a method, wherein directing the wireless interrogation unit includes directing a control unit associated with the wireless interrogation unit.

40) The non-transitory computer readable storage medium according to any one of embodiments 36 to 39, wherein said tube, medical device, or kit is an assembly according to any one of embodiments 1 to 19.

41) The storage medium according to any one of embodiments 36 to 40 wherein said collected sensor data is received on a watch, wrist band, cell phone or glasses.

42) The storage medium according to any one of embodiments 36 to 41 wherein said collected sensor data is received within a subject's residence or office.

43) The storage medium according to any one of embodiments 36 to 42 wherein said collected sensed data is provided to a health care provider.

44) The storage medium according to any one of embodiments 36 to 43 wherein said sensed data is posted to one or more websites.

45) The method according to any one of embodiments 31 to 35, or storage medium according to any one of embodiments 36 to 44, wherein said data is analyzed.

46) The method or storage medium according to embodiment 45 wherein said data is plotted to enable visualization of change over time.

47) The method or storage medium according to embodiments 45 or 46 wherein said data is plotted to provide a three-dimensional image.

48) A method for determining degradation of a tube, comprising the steps of a) providing to a body passageway of a subject a tube according to any one of embodiments 1 to 7 or 16 to 19, and b) detecting a change in a sensor, and thus determining degradation of the tube.

49) The method according to embodiment 48 wherein said sensor is capable of detecting one or more physiological and/or locational parameters.

50) The method according to embodiment 48 or 49 wherein said sensor detects contact, fluid flow, pressure and/or temperature.

51) The method according to any one of embodiments 48 to 50 wherein said sensor detects a location within the subject.

52) The method according to any one of embodiments 48 to 50 wherein said sensor moves and/or is eliminated by the body upon degradation of the tube.

53) The method according to any one of embodiments 48 to 52 wherein the step of detecting is a series of detections over time.

54) A method for determining an infection associated with a tube, comprising the steps of a) providing to a body passageway of a subject a tube according to any one of embodiments 1 to 7 or 16 to 19, wherein said tube comprises at least one temperature sensor and/or metabolic sensor, and b) detecting a change in said temperature sensor and/or metabolic sensor, and thus determining the presence of an infection.

55) The method according to embodiment 54 wherein the step of detecting is a series of detections over time.

56) The method according to embodiments 54 or 55 wherein said change is greater than a 1% change over the period of one hour.

57) The method according to embodiments 54 to 56 wherein said change is a continually increasing temperature and/or metabolic activity over the course of 4 hours.

The various embodiments described above can be combined to provide further embodiments. All of the U.S. patents, U.S. patent application publications, U.S. patent applications, foreign patents, foreign patent applications and non-patent publications referred to in this specification are incorporated herein by reference, in their entirety. Aspects of the embodiments can be modified, if necessary to employ concepts of the various patents, applications and publications to provide yet further embodiments.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method of monitoring for abnormal leakage of a liquid out of a medical tube that is implanted within a patient, the method comprising:
    a. monitoring a first surface environment of the medical tube that is implanted within the patient, where the monitoring of the first surface environment is performed at a first time by a liquid flow sensor located on an adluminal surface of the medical tube, to thereby provide a first measurement of liquid flow;
    b. monitoring the first surface environment of the medical tube that is implanted within the patient at a second time by the one or more liquid flow sensors located on the adluminal surface of the medical tube, to thereby provide a second measurement of liquid flow, where the second time is later than the first time; and
    c. comparing the first and second liquid flow measurements; where an increase in liquid flow at the second time compared to the liquid flow at the first time indicates abnormal leakage of liquid out of the medical tube.

2. The method of claim 1 wherein the medical tube is a catheter.

3. The method of claim 1 wherein the medical tube is a Foley catheter.

4. The method of claim 1 wherein the medical tube is a central venous catheter.

5. The method of claim 1 wherein the medical tube is a drainage tube.

6. A method of monitoring for abnormal leakage of a liquid out of a medical tube that is implanted within a patient, the method comprising:
    a. monitoring a first surface environment of the medical tube that is implanted within the patient, where the monitoring of the first surface environment is performed at a first time by a liquid flow sensor located on a luminal surface of the medical tube, to thereby provide a first measurement of liquid flow;
    b. monitoring the first surface environment of the medical tube that is implanted within the patient at a second time by the one or more liquid flow sensors located on the luminal surface of the medical tube, to thereby provide a second measurement of liquid flow, where the second time is later than the first time; and
    c. comparing the first and second liquid flow measurements; where an increase in liquid flow at the second time compared to the liquid flow at the first time indicates abnormal leakage of liquid out of the medical tube.

7. The method of claim 6 wherein the medical tube is a catheter.

8. The method of claim 6 wherein the medical tube is a Foley catheter.

9. The method of claim 6 wherein the medical tube is a central venous catheter.

10. The method of claim 6 wherein the medical tube is a drainage tube.

\* \* \* \* \*